United States Patent
Wichmann et al.

(10) Patent No.: US 7,514,443 B2
(45) Date of Patent: Apr. 7, 2009

(54) SUBSTITUTED PYRAZOLO[1,5-A]PYRIMIDINES AS INHIBITORS OF METABOTROPIC GLUTAMATE RECEPTORS

(75) Inventors: Juergen Wichmann, Steinen (DE); Thomas Johannes Woltering, Weil am Rhein (DE)

(73) Assignee: Hoffmann-La Roche Inc., Nutley, NJ (US)

(*) Notice: Subject to any disclaimer, the term of this patent is extended or adjusted under 35 U.S.C. 154(b) by 85 days.

(21) Appl. No.: 11/707,480

(22) Filed: Feb. 16, 2007

(65) Prior Publication Data

US 2008/0051421 A1 Feb. 28, 2008

Related U.S. Application Data

(62) Division of application No. 10/948,970, filed on Sep. 24, 2004, now Pat. No. 7,329,662.

(30) Foreign Application Priority Data

Oct. 3, 2003 (EP) .................... 03078075

(51) Int. Cl.
*C07D 487/04* (2006.01)
*A61K 31/519* (2006.01)
*A61P 25/16* (2006.01)
*A61P 25/28* (2006.01)
*A61P 25/24* (2006.01)
*A61P 25/22* (2006.01)
*A61P 25/30* (2006.01)
*A61P 25/06* (2006.01)

(52) U.S. Cl. .................... 514/259.3; 544/281
(58) Field of Classification Search ............. 544/281; 514/259.3
See application file for complete search history.

(56) References Cited

U.S. PATENT DOCUMENTS

2003/0139426 A1  7/2003  Wilde et al.

FOREIGN PATENT DOCUMENTS

| EP | 0 891 978 A2 | 1/1999 |
|---|---|---|
| WO | WO 97/29109 A1 | 8/1997 |
| WO | WO 02/083652 | 10/2002 |
| WO | WO 03/048132 A2 | 6/2003 |

OTHER PUBLICATIONS

Shaw, P. *Curr. Opin. in Neurology & Neurosurgery*, (1993) 6:414-422.
Thomas, R.J., *JAGS*, (1995) 43:11, 1279-1289.
Hoelscher et al, *Neurosci and Biobehavioral Reviews*, 23, (1999) 399-410.
Rouse, S. et al, *Pharmacology and Therapeutics*, (2000) 88, 427-435.
Taylor et al, *Jour. of Neurochem*, (2002) 82, 1179-1191.
Sabbatini F. et al, *Expert. Opin. Ther. Patents*, (2004) 14(11):1593-1604.
Chojnacka-Wojcik, E. et al, *European Jour. of Pharmacology*, (1997) 319, 153-156.
Hyoung-Gon Lee et al, *Acta Neurobiol Exp*, (2004) 64:89-98.
Knoepfel, T. et al, *DDT*, 1:3 (1996) 103-108.
Conn, P. J. et al, *Annu, Rev. Pharmacol, Toxicol* (197) 37:205-37, 1997.
Wohlfarth S et al, *Amino Acids*, (2000) 19:95-101.
Knoepfel, T. et al, *Jour. of Medicinal Chem.*, 38:9, 1417-1425, 1996.
Riedel, G. *TINS*, 13:6, 1996219-224, 1995.
Moghaddam, B. et al, *Science*, 281: (1998) 1349-1352.
Chapman et al, *Euro. Jour. of Pharmacology*, 368 (1999) 17-24.
Schoepp et al, *Neuropharmacology*, 38 (1999) 1431-1476.
Braeuner-Osborne et al, *Amer. Chem. Soc.*, 43:14 (2000) 2609-2645.
Costantino et al, *Expert Opin, Ther. Targets*, (2001) 5(6): 669-683.
Nicoletti, F. et al, *Trends Neurosci*, (1996) 19, 267-271.
Fraley et al., *Bioorg. Med. Chem. Lett.*, 12, pp. 3537-3541 (2002).
Database Chemcats Online, Chemical Abstract Service, Columbus, Ohio, US, XP002316354, downloaded Apr. 2, 2005.

*Primary Examiner*—Brenda L Coleman
*Assistant Examiner*—Susanna Moore
(74) *Attorney, Agent, or Firm*—George W. Johnston; Patricia S. Rocha-Tramaloni; Kimberly J. Prior

(57) ABSTRACT

The present invention relates to novel pyrazolo- and imidazopyrimidine derivatives of formula I

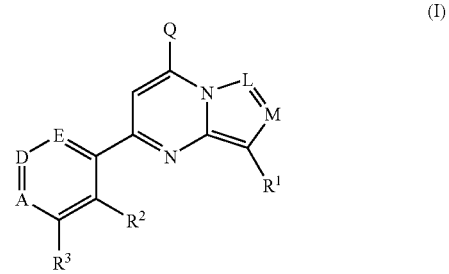

wherein A, D, E, L, M, Q, $R^1$, $R^2$ and $R^3$ are as defined hereinabove. The present invention also relates to a process for their preparation, a pharmaceutical composition containing said derivatives and a method of treating or preventing acute or chronic neurological disorder comprising administering to a patient in need of such treatment a pharmaceutical composition comprising a therapeutically effective amount of at least one such derivatives. These disorders include acute and chronic disorders.

16 Claims, No Drawings

SUBSTITUTED PYRAZOLO[1,5-A]PYRIMIDINES AS INHIBITORS OF METABOTROPIC GLUTAMATE RECEPTORS

PRIORITY TO RELATED APPLICATIONS

This application is a division of U.S. application Ser. No. 10/948,970, filed Sep. 24, 2004, now pending; which claims the benefit of European Application No. 03078075.3, filed Oct. 3, 2003.

FIELD OF THE INVENTION

The present invention relates to a compound of formula I

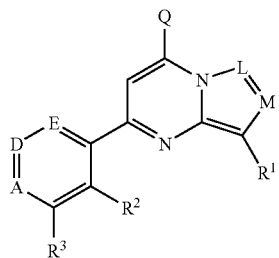

wherein A, D, E, L, M, Q, $R^1$, $R^2$ and $R^3$ are described hereinbelow, or a pharmaceutically acceptable salt thereof. This invention also relates to a pharmaceutical composition comprising the pyrazolo- and imidazo-pyrimidine derivatives of formula I, a process for preparing the compound of formula I and a method of treating or preventing acute or chronic neurological disorders comprising administering to a patient in need of such treatment a therapeutically effective amount of said pharmaceutical composition. These disorders include acute and chronic disorders

BACKGROUND OF THE INVENTION

In the central nervous system (CNS), the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by pharmaceutical preparations, i.e., medicaments, as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR2 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain, drug dependency, smoking cessation und ethanol dependence (*Expert Opin. Ther. Patents* (2002), 12, (12), 3537-3541).

Selective mGluR2 antagonists are especially useful for the treatment of anxiety and pain.

SUMMARY OF THE INVENTION

This invention relates to a compound of formula 1

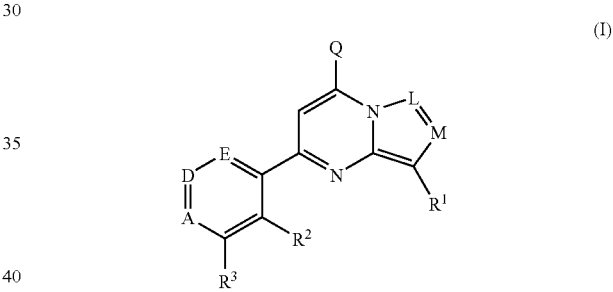

wherein
A is $=C(R^4)-$,
D is $=C(R^5)-$,
E is $=C(R^6)-$,
or one of A, D and E is $=N-$,
L is $=N-$ or $=C(H)-$,
M is $=C(R^7)-$, when L is $=N-$, or M is $=N-$, when L is $=C(H)-$,
Q is $CF_3$ of $CHF_2$,
$R^1$ is selected from $-CN$, unsubstituted pyridinyl, pyridinyl substituted by $(C_1-C_4)$-alkyl, pyridinyl substituted by $(C_1-C_4)$-alkanol, and corresponding pyridine-N-oxide of unsubstituted pyridinyl, pyridinyl substituted by $(C_1-C_4)$-alkyl, pyridinyl substituted by $(C_1-C_4)$-alkanol,
$R^2$ is selected from hydrogen, halogen, $(C_1-C_4)$-alkyl and $(C_3-C_6)$-cycloalkyl,
$R^3$ is selected from hydrogen, halogen, $(C_1-C_4)$-alkyl and $(C_3-C_6)$-cycloalkyl,
$R^4$ is selected from hydrogen, halogen, unsubstituted $(C_1-C_4)$-alkyl, $(C_1-C_4)$-alkyl substituted by fluorine, unsubstituted $(C_1-C_4)$-alkoxy, $(C_1-C_4)$-alkoxy substituted by fluorine, unsubstituted $(C_3-C_6)$-cycloalkyl and $(C_3-C_6)$-cycloalkyl substituted by fluorine, $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine, $R^6$ is hydrogen or halogen, and $R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by CN, with the proviso that when A is =$C(R^4)$—, D is =C(H)—, E is =C(H)—, L is =N—, $R^1$ is —CN, $R^2$ is hydrogen, $R^3$ is hydrogen, and (a) M is =C(H)—, $R^4$ is not selected from hydrogen, chloro or methoxy; or (b) M is =$C(CH_3)$—, $R^4$ is not hydrogen, or a pharmaceutically acceptable salt thereof.

Another embodiment of this invention is related to a process for preparing a compound of formula I. Another embodiment of this invention is related to a pharmaceutical composition containing a compound of formula I and a pharmaceutically acceptable excipient. Yet another embodiment of this invention is related to a method of treatment or prevention of mGluR2 receptor mediated disorders.

DETAILED DESCRIPTION OF THE INVENTION

The following description of general terms used in the present description apply irrespective of whether the term in question appear alone or in combination.

Examples for alkyl include straight chain and branched saturated carbon chains containing from one to 4 carbon atoms, e.g. methyl, ethyl, and the isomers of propyl and butyl, e.g. isopropyl and tert-butyl. Examples for substituted alkyl include $CF_3$ and $CH_2CN$. An example for alkoxy is ethoxy. An example for substituted ethoxy is $OCH_2CF_3$. Examples for cycloalkyl include cyclopropyl, cyclobutyl, cyclopentyl and cyclohexyl.

Examples for pyridinyl are pyridin-2-yl, pyridin-3-yl and pyridin-4-yl. Examples for substituted pyridinyl are methylpyridinyl, dimethylpyridinyl, hydroxymethylpyridinyl and methyloxypyridinyl, e.g. 2-methylpyridinyl, 2,6-dimethylpyridinyl, 2-hydroxymethylpyridinyl and 2-methyl-1-oxypyridinyl, e.g. 2-methylpyridin-4-yl, 2,6-dimethylpyridin-4-yl, 2-hydroxymethylpyridin-4-yl and 2-methyl-1-oxypyridin-4-yl.

Examples for halogen are chlorine and fluorine.

Unless otherwise specified, the term "alkanol" as defined therein denotes an alkyl radical having 1 to 10 carbon atoms, preferably 1 to 6 and still more preferably 1 to 4 carbon atoms as defined above, which is substituted by one, two or three, preferably one, hydroxyl group(s). Examples of alkanols include methanol, ethanol, n-propan-2-ol, n-propan-3-ol, isopropanol, i-butanol and those specifically exemplified in the instant application among the examples.

The term "pharmaceutically acceptable salt" refers to any salt derived from an inorganic or organic acid or base. Examples include the hydrochloride, sulfate, fumarate, mesylate, phosphate, maleate and tartrate salts. Such salts may be prepared according to common and general methods known by the person skilled in the art.

The term "pharmaceutically acceptable excipient" refers to a pharmaceutically acceptable carrier, vehicle, diluent, adjustment or similar mechanism for delivering a pharmaceutical composition.

The term therapeutically effective amount" refers to an amount of at least one compound of formula I, or a pharmaceutically acceptable salt thereof, that modulates metabotropic glutamate receptors, including mGluR2.

In one embodiment, this invention relates to a compound of formula I, wherein:

A is =$C(R^4)$—,

D is =$C(R^5)$—,

E is =$C(R^6)$—, or one of A, D and E is =N—,

L is =N— or =C(H)—,

M is =$C(R^7)$—, when L is =N—, or M is =N—, when L is =C(H)—,

Q is $CF_3$, $R^1$ is selected from —CN, unsubstituted pyridinyl, pyridinyl substituted by ($C_1$-$C_4$)-alkyl and corresponding pyridine-N-oxide of pyridinyl substituted by ($C_1$-$C_4$)-alkyl, $R^2$ is selected from hydrogen, halogen, ($C_1$-$C_4$)-alkyl and ($C_3$-$C_6$)-cycloalkyl, $R^3$ is selected from hydrogen, halogen, ($C_1$-$C_4$)-alkyl and ($C_3$-$C_6$)-cycloalkyl, $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine, $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine, $R^6$ is hydrogen or halogen, and $R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by CN, with the proviso that when A is =$C(R^4)$—, D is =C(H)—, E is =C(H)—, L is =N—, $R^1$ is —CN, $R^2$ is hydrogen, $R^3$ is hydrogen, and (a) M is =C(H)—, $R^4$ is not selected from hydrogen, chloro and methoxy; or (b) M is =$C(CH_3)$—, $R^4$ is not hydrogen, and their pharmaceutically acceptable addition salts.

In another embodiment, the present invention provides a compound of formula I wherein A is =$C(R^4)$—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine. In another embodiment, the invention provides a compound of formula I wherein A is =$C(R^4)$—, wherein $R^4$ is selected from hydrogen, Cl, F, $CH_3$, $CF_3$, $OCH_3$, $OCH_2CH_3$ and $OCH_2CF_3$. In still another embodiment, the invention provides a compound of formula I wherein A is =$C(R^4)$—, wherein $R^4$ is $CF_3$.

In another embodiment, the present invention provides a compound of formula I wherein D is =$C(R^5)$—, wherein $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine. In another embodiment, the invention provides a compound of formula I wherein D is =$C(R^5)$—, wherein $R^5$ is selected from hydrogen, Cl, F, $CH_3$ and $CF_3$. In still another embodiment, the invention provides a compound of formula I wherein D is =$C(R^5)$—, wherein $R^5$ is selected from hydrogen, F and $CH_3$.

In another embodiment, the present invention provides a compound of formula I wherein E is =$C(R^6)$—, wherein $R^6$ is hydrogen or halogen. In another embodiment, the invention provides a compound of formula I wherein E is =$C(R^6)$—, wherein $R^6$ is hydrogen. In one embodiment, the present invention provides a compound of formula I wherein L is =N—. In another embodiment, the invention provides a compound of formula I wherein L is =C(H)—.

In another embodiment, the present invention provides a compound of formula I wherein M is =C($R^7$)—, wherein $R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by CN. In another embodiment, the invention provides a compound of formula I wherein M is =C($R^7$)—, wherein $R^7$ is hydrogen. In still another embodiment, the invention provides a compound of formula I wherein M is =C($R^7$)—, wherein $R^7$ is unsubstituted ($C_1$-$C_4$)-alkyl or ($C_1$-$C_4$)-alkyl substituted by CN. In still another embodiment, the present invention provides a compound of formula I wherein M is =C($R^7$)—, wherein $R^7$ is $CH_3$ or $CH_2CN$. In another embodiment, the present invention provides a compound of formula I wherein M is =N—.

In another embodiment, the present invention provides a compound of formula I wherein $R^1$ is —CN. In another embodiment, the invention provides a compound of formula I wherein $R^1$ is selected from unsubstituted pyridinyl, pyridinyl substituted by ($C_1$-$C_4$)-alkyl and the corresponding pyridine-N-oxide of pyridinyl substituted by ($C_1$-$C_4$)-alkyl. In still another embodiment, the invention provides a compound of formula I wherein $R^1$ is selected from pyridin-2-yl, pyridin-3-yl, pyridin-4-yl, methylpyridin-4-yl, dimethylpyridin-4-yl, hydroxymethylpyridin-4-yl and methyloxypyridin-4-yl. In still another embodiment, the invention provides a compound of formula I wherein $R^1$ is selected from pyridin-3-yl, pyridin-4-yl, 2-methylpyridin-4-yl, 2,6-dimethylpyridin-4-yl, 2-hydroxymethylpyridin-4-yl and 2-methyl-1-oxy-pyridin-4-yl. In still another embodiment, the invention provides a compound of formula I wherein $R^1$ is selected from pyridin-4-yl, 2-methylpyridin-4-yl and 2,6-dimethylpyridin-4-yl.

In one embodiment, the present invention provides a compound of formula I wherein $R^2$ is hydrogen.

In one embodiment, the present invention provides a compound of formula I wherein $R^3$ is hydrogen.

In another embodiment, the present invention provides a compound of formula I wherein
A is =C($R^4$)—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine,
D is =C($R^5$)—, wherein $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine,
E is =C($R^6$)—, wherein $R^6$ is hydrogen or halogen,
L is =N— or =C(H)—,
M is =C($R^7$)—, wherein $R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl, and ($C_3$-$C_6$)-cycloalkyl substituted by CN, when L is =N—; or M is =N—, when L is =C(H)—,
$R^1$ is selected from —CN, unsubstituted pyridinyl, pyridinyl substituted by ($C_1$-$C_4$)-alkyl, and the corresponding pyridine-N-oxide of pyridinyl substituted by ($C_1$-$C_4$)-alkyl,
$R^2$ is selected from hydrogen, halogen, ($C_1$-$C_4$)-alkyl and ($C_3$-$C_6$)-cycloalkyl,
$R^3$ is selected from hydrogen, halogen, ($C_1$-$C_4$)-alkyl and ($C_3$-$C_6$)-cycloalkyl,
with the proviso that when A is =C($R^4$)—, D is =C(H)—, E is =C(H)—, L is =N—, $R^1$ is —CN, $R^2$ is hydrogen, $R^3$ is hydrogen, and (a) M is =C(H)—, $R^4$ is not selected from hydrogen, chloro and methoxy; or (b) M is =C($CH_3$)—, $R^4$ is not hydrogen.

In another embodiment, the present invention provides a compound of formula I wherein
A is =C($R^4$)—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine,
D is =C($R^5$)—, wherein $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine,
E is =C($R^6$)—, wherein $R^6$ is hydrogen or halogen,
L is =N—,
M is =C($R^7$)—, wherein $R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by CN,
$R^1$ is selected from —CN, unsubstituted pyridinyl, pyridinyl substituted ($C_1$-$C_4$)-alkyl, and the corresponding pyridine-N-oxide of pyridinyl substituted ($C_1$-$C_4$)-alkyl,
$R^2$ is selected from hydrogen, halogen and ($C_1$-$C_4$)-alkyl,
$R^3$ is selected from hydrogen, halogen and ($C_1$-$C_4$)-alkyl,
with the proviso that when A is =C($R^4$)—, D is =C(H)—, E is =C(H)—, L is =N—, $R^1$ is —CN, $R^2$ is hydrogen, $R^3$ is hydrogen, and (a) M is =C(H)—, $R^4$ is not selected from hydrogen, chloro and methoxy; or (b) M is =C($CH_3$)—, $R^4$ is not hydrogen.

In still another embodiment, the present invention provides a compound of formula I wherein
A is =C($R^4$)—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine,
D is =C($R^5$)—, wherein $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine,
E is =C($R^6$)—, wherein $R^6$ is hydrogen or halogen,
L is =N—,
M is =C($R^7$)—, wherein $R^7$ is selected form hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by fluorine,
$R^1$ is —CN,
$R^2$ is selected from hydrogen, halogen and ($C_1$-$C_4$)-alkyl,
$R^3$ is selected from hydrogen, halogen and ($C_1$-$C_4$)-alkyl,
with the proviso that when A is =C($R^4$)—, D is =C(H)—, E is =C(H)—, L is =N—, $R^1$ is —CN, $R^2$ is hydrogen, $R^3$ is hydrogen, and (a) M is =C(H)—, $R^4$ is not selected from hydrogen, chloro and methoxy; or (b) M is =C($CH_3$)—, $R^4$ is not hydrogen.

In still another embodiment, the present invention provides a compound of formula I wherein
A is =C($R^4$)—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy and ($C_1$-$C_4$)-alkoxy substituted by fluorine,
D is =C($R^5$)—, wherein $R^5$ is selected from hydrogen, halogen, unsubstituted ($C_1$-$C_4$)-alkyl and ($C_1$-$C_4$)-alkyl substituted by fluorine,
E is =C($R^6$)—, wherein $R^6$ is hydrogen or halogen,
L is =N—, M is =C(R$^7$)—, wherein R$^7$ is selected from hydrogen, unsubstituted (C$_1$-C$_4$)-alkyl and (C$_1$-C$_4$)-alkyl substituted by CN,
R$^1$ is —CN, and
R$^2$ and R$^3$ are hydrogen,
with the proviso that when A is =C(R$^4$)—, D is =C(H)—, E is =C(H)—, L is =N—, R$^1$ is —CN, R$^2$ is hydrogen, R$^3$ is hydrogen, and M is =C(H)—, R$^4$ is not selected from hydrogen, chloro and methoxy.

In still another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =N—,
M is =C(R$^7$)—, wherein R$^7$ is hydrogen,
R$^1$ is —CN, and
R$^2$ and R$^3$ are hydrogen,
with the proviso that when A is =C(R$^4$)—, D is =C(H)—, E is =C(H)—, L is =N—, R$^1$ is —CN, R$^2$ is hydrogen, R$^3$ is hydrogen, and M is =C(H)—, R$^4$ is not selected from hydrogen, chloro and methoxy.

In still another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen,
L is =N—,
M is =C(R$^7$)—, wherein R$^7$ is hydrogen,
R$^1$ is —CN, and
R$^2$ and R$^3$ are hydrogen,
with the proviso that when A is =C(R$^4$)—, D is =C(H)—, E is =C(H)—, L is =N—, R$^1$ is —CN, R$^2$ is hydrogen, R$^3$ is hydrogen, and M is =C(H)—, R$^4$ is not selected from hydrogen, chloro and methoxy.

In still another embodiment, the present invention provides a compound of formula I wherein
A is =C(R$^4$)—, wherein R$^4$ is selected from hydrogen, Cl, F, methyl, trifluoromethyl and 2-trifluoroethoxy,
D is =C(R$^5$)—, wherein R$^5$ is selected from hydrogen, Cl, F, methyl and trifluoromethyl,
E is =C(R$^6$)—, wherein R$^6$ is hydrogen,
L is =N—,
M is =C(R$^7$)—, wherein R$^7$ is hydrogen,
R$^1$ is —CN, and
R$^2$ and R$^3$ are hydrogen,
with the proviso that when A is =C(R$^4$)—, D is =C(H)—, E is =C(H)—, L is =N—, R$^1$ is —CN, R$^2$ is hydrogen, R$^3$ is hydrogen, and M is =C(H)—, R$^4$ is selected from not hydrogen, chloro and methoxy.

In still another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine
E is =C(R$^6$)—, wherein R$^6$ is hydrogen or halogen
L is =N—,
M is =C(R$^7$)—, wherein R$^7$ is unsubstituted (C$_1$-C$_4$)-alkyl or (C$_1$-C$_4$)-alkyl substituted by CN,
R$^1$ is —CN, and
R$^2$ and R$^3$ are hydrogen,
with the proviso that when A is =C(R$^4$)—, D is =C(H)—, E is =C(H)—, L is =N—, R$^1$ is —CN, R$^2$ is hydrogen, R$^3$ is hydrogen, and M is =C(CH$_3$)—, R$^4$ is not hydrogen.

In still another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =N—,
M is =C(R$^7$)—, wherein R$^7$ is selected from hydrogen, unsubstituted (C$_1$-C$_4$)-alkyl and (C$_1$-C$_4$)-alkyl substituted by CN
R$^1$ is selected from unsubstituted pyridinyl, pyridinyl substituted by (C$_1$-C$_4$)-alkyl, and the corresponding pyridine-N-oxide of pyridinyl substituted by (C$_1$-C$_4$)-alkyl,
R$^2$ is selected from hydrogen, halogen and (C$_1$-C$_4$)-alkyl, and
R$^3$ is selected from hydrogen, halogen and (C$_1$-C$_4$)-alkyl.

In still another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =N—,
M is =C(R$^7$)—, wherein R$^7$ is hydrogen,
R$^1$ is selected from unsubstituted pyridinyl, pyridinyl substituted by (C$_1$-C$_4$)-alkyl, and the corresponding pyridine-N-oxide of pyridinyl substituted by (C$_1$-C$_4$)-alkyl, and
R$^2$ and R$^3$ are hydrogen.

In still another embodiment, the present invention provides a compound of formula I wherein
A is =C(R$^4$)—, wherein R$^4$ is selected from hydrogen, halogen, (C$_1$-C$_4$)-alkyl substituted by fluorine, and unsubstituted (C$_1$-C$_4$)-alkoxy,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =N—,
M is =C(R$^7$)—, wherein R$^7$ is hydrogen,
R$^1$ is unsubstituted pyridin-4-yl or pyridin-4-yl substituted by (C$_1$-C$_4$)-alkyl, and
R$^2$ and R$^3$ are hydrogen.

In still another embodiment, the present invention provides a compound of formula I wherein
A is =C(R$^4$)—, wherein R$^4$ is (C$_1$-C$_4$)-alkyl substituted by fluorine, D is =C(R$^5$)—, wherein R$^5$ is selected from hydrogen, halogen, unsubstituted (C$_1$-C$_4$)—, alkyl and (C$_1$-C$_4$)-alkyl substituted by fluorine,
E is =C(R$^6$)—, wherein R$^6$ is hydrogen,
L is =N—,
M is =C(R$^7$)—, wherein R$^7$ is hydrogen,
R$^1$ is unsubstituted pyridin-4-yl or pyridin-4-yl substituted by (C$_1$-C$_4$)-alkyl, and
R$^2$ and R$^3$ are hydrogen.

In another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =C(H)—,
M is =N—,
R$^1$ is selected from —CN, unsubstituted pyridinyl, pyridinyl substituted by (C$_1$-C$_4$)-alkyl, and the corresponding pyridine-N-oxide of pyridinyl substituted by (C$_1$-C$_4$)-alkyl,
R$^2$ is selected from hydrogen, halogen and (C$_1$-C$_4$)-alkyl, and
R$^3$ is selected from hydrogen, halogen and (C$_1$-C$_4$)-alkyl.

In another embodiment, the present invention provides a compound of formula I wherein
A is =C(R$^4$)—, wherein R$^4$ is selected from hydrogen, halogen, unsubstituted (C$_1$-C$_4$)-alkyl, (C$_1$-C$_4$)-alkyl substituted by fluorine, unsubstituted (C$_1$-C$_4$)-alkoxy and (C$_1$-C$_4$)-alkoxy substituted by fluorine,
D is =C(R$^5$)—, wherein R$^5$ is selected from hydrogen, halogen, unsubstituted (C$_1$-C$_4$)-alkyl and (C$_1$-C$_4$)-alkyl substituted by fluorine,
E is =C(R$^6$)—, wherein R$^6$ is hydrogen or halogen,
L is =C(H)—,
M is =N—,
R$^1$ is —CN,
R$^2$ is selected from hydrogen, halogen and (C$_1$-C$_4$)-alkyl, and
R$^3$ is selected from hydrogen, halogen and (C$_1$-C$_4$)-alkyl.

In another embodiment, the present invention provides a compound of formula I wherein
A is =C(R$^4$)—, wherein R$^4$ is hydrogen or halogen,
D is =C(R$^5$)—, wherein R$^5$ is hydrogen,
E is =C(R$^6$)—, wherein R$^6$ is hydrogen or halogen,
L is =C(H)—,
M is =N—,
R$^1$ is —CN, and
R$^2$ and R$^3$ are hydrogen.

In one embodiment, the present invention provides a compound of formula I selected from
2-phenyl-4-trifluoromethyl-imidazo[1,5-a]pyrimidine-8-carbonitrile,
2-(3-chloro-phenyl)-4-trifluoromethyl-imidazo[1,5-a]pyrimidine-8-carbonitrile,
2-(4-trifluoromethyl-phenyl)-4-trifluoromethyl-imidazo[1,5-a]pyrimidine-8-carbonitrile,
5-(4-trifluoromethyl-phenyl)-7-trifluoromethyl-pyrazolo[1,5-a]pyrimidine-3-carbonitrile,
5-(4-fluoro-3-trifluoromethyl-phenyl)-7-trifluoromethyl-pyrazolo[1,5-a]pyrimidine-3-carbonitrile,
5-(3-chloro-4-fluoro-phenyl)-7-trifluoromethyl-pyrazolo[1,5-a]pyrimidine-3-carbonitrile,
5-(4-chloro-3-methyl-phenyl)-7-trifluoromethyl-pyrazolo[1,5-a]pyrimidine-3-carbonitrile,
5-(3,4-dichloro-phenyl)-7-trifluoromethyl-pyrazolo[1,5-a]pyrimidine-3-carbonitrile,
5-(4-chloro-3-methyl-phenyl)-7-trifluoromethyl-imidazo[1,5-a]pyrimidine-8-carbonitrile, and
5-(3,4-dichloro-phenyl)-7-trifluoromethyl-imidazo[1,5-a]pyrimidine-8-carbonitrile.

In another embodiment, the present invention provides a compound of formula I selected from
5-(4-chloro-phenyl)-3-pyridin-3-yl-7-trifluoromethyl-pyrazolo[1,5-a]pyrimidine,
5-(4-chloro-phenyl)-3-pyridin-4-yl-7-trifluoromethyl-pyrazolo[1,5-a]pyrimidine,
5-(4-chloro-3-methyl-phenyl)-3-pyridin-4-yl-7-trifluoromethyl-pyrazolo[1,5-a]pyrimidine,
5-(3-chloro-4-fluoro-phenyl)-3-pyridin-3-yl-7-trifluoromethyl-pyrazolo[1,5-a]pyrimidine,
5-(3-chloro-4-fluoro-phenyl)-3-pyridin-4-yl-7-trifluoromethyl-pyrazolo[1,5-a]pyrimidine,
5-(3,4-dichloro-phenyl)-3-pyridin-3-yl-7-trifluoromethyl-pyrazolo[1,5-a]pyrimidine,
5-(3,4-dichloro-phenyl)-3-pyridin-4-yl-7-trifluoromethyl-pyrazolo[1,5-a]pyrimidine,
5-(3-fluoro-4-trifluoromethyl-phenyl)-7-trifluoromethyl-imidazo[1,5-a]pyrimidine-8-carbonitrile,
5-(4-trifluoromethyl-phenyl)-3-pyridin-4-yl-7-trifluoromethyl-pyrazolo[1,5-a]pyrimidine, and
5-(3-trifluoromethyl-phenyl)-3-pyridin-4-yl-7-trifluoromethyl-pyrazolo[1,5-a]pyrimidine.

In one embodiment, the present invention provides a compound of formula I selected from
5-(3-fluoro-4-trifluoromethyl-phenyl)-3-pyridin-4-yl-7-trifluoromethyl-pyrazolo[1,5-a]pyrimidine,
5-(4-chloro-phenyl)-3-(2,6-dimethyl-pyridin-4-yl)-7-trifluoromethyl-pyrazolo[1,5-a]pyrimidine,
5-(4-chloro-3-methyl-phenyl)-3-(2,6-dimethyl-pyridin-4-yl)-7-trifluoromethyl-pyrazolo[1,5-a]pyrimidine,
5-(3-chloro-4-fluoro-phenyl)-3-(2,6-dimethyl-pyridin-4-yl)-7-trifluoromethyl-pyrazolo[1,5-a]pyrimidine,
5-(3,4-dichloro-phenyl)-3-(2,6-dimethyl-pyridin-4-yl)-7-trifluoromethyl-pyrazolo[1,5-a]pyrimidine,
5-(4-trifluoromethyl-phenyl)-3-(2,6-dimethyl-pyridin-4-yl)-7-trifluoromethyl-pyrazolo[1,5-a]pyrimidine,
5-(3-trifluoromethyl-phenyl)-3-(2,6-dimethyl-pyridin-4-yl)-7-trifluoromethyl-pyrazolo[1,5-a]pyrimidine,
5-(3-fluoro-4-trifluoromethyl-phenyl)-3-(2,6-dimethyl-pyridin-4-yl)-7-trifluoromethyl-pyrazolo[1,5-a]pyrimidine,
5-(4-methyl-3-trifluoromethyl-phenyl)-3-(2,6-dimethyl-pyridin-4-yl)-7-trifluoromethyl-pyrazolo[1,5-a]pyrimidine, and
5-(4-chloro-phenyl)-3-(2-methyl-pyridin-4-yl)-7-trifluoromethyl-pyrazolo[1,5-a]pyrimidine.

In another embodiment, the present invention provides a compound of formula I selected from
5-(4-chloro-3-methyl-phenyl)-3-(2-methyl-pyridin-4-yl)-7-trifluoromethyl-pyrazolo[1,5-a]pyrimidine,
5-(3-chloro-4-fluoro-phenyl)-3-(2-methyl-pyridin-4-yl)-7-trifluoromethyl-pyrazolo[1,5-a]pyrimidine,
5-(3,4-dichloro-phenyl)-3-(2-methyl-pyridin-4-yl)-7-trifluoromethyl-pyrazolo[1,5-a]pyrimidine,
5-(4-trifluoromethyl-phenyl)-3-(2-methyl-pyridin-4-yl)-7-trifluoromethyl-pyrazolo[1,5-a]pyrimidine,
5-(3-trifluoromethyl-phenyl)-3-(2-methyl-pyridin-4-yl)-7-trifluoromethyl-pyrazolo[1,5-a]pyrimidine,
5-(3-fluoro-4-trifluoromethyl-phenyl)-3-(2-methyl-pyridin-4-yl)-7-trifluoromethyl-pyrazolo[1,5-a]pyrimidine,
2-(4-methyl-3-trifluoromethyl-phenyl)-4-trifluoromethyl-imidazo[1,5-a]pyrimidine-8-carbonitrile, 5-(3-methyl-4-trifluoromethyl-phenyl)-3-pyridin-4-yl-7-trifluoromethyl-pyrazolo[1,5-a]pyrimidine,
5-(3-methyl-4-trifluoromethyl-phenyl)-3-(2,6-dimethyl-pyridin-4-yl)-7-trifluoromethyl-pyrazolo[1,5-a]pyrimidine, and
5-(3-methyl-4-trifluoromethyl-phenyl)-3-(2-methyl-pyridin-4-yl)-7-trifluoromethyl-pyrazolo[1,5-a]pyrimidine.

In another embodiment, the present invention provides a compound of formula I selected from
2-(3-methyl-4-trifluoromethyl-phenyl)-4-trifluoromethyl-pyrazolo[1,5-a]pyrimidine-8-carbonitrile,
2-(3-methyl-4-trifluoromethyl-phenyl)-4-trifluoromethyl-imidazo[1,5-a]pyrimidine-8-carbonitrile,
2-(4-trifluoroethoxy-3-trifluoromethyl-phenyl)-4-trifluoromethyl-pyrazolo[1,5-a]pyrimidine-8-carbonitrile,
2-(4-trifluoroethoxy-3-trifluoromethyl-phenyl)-4-trifluoromethyl-imidazo[1,5-a]pyrimidine-8-carbonitrile,
5-(4-ethoxy-3-trifluoromethyl-phenyl)-3-pyridin-4-yl-7-trifluoromethyl-pyrazolo[1,5-a]pyrimidine,
5-(4-trifluorothoxy-3-trifluoromethyl-phenyl)-3-pyridin-4-yl-7-trifluoromethyl-pyrazolo[1,5-a]pyrimidine,
5-(4-ethoxy-3-trifluoromethyl-phenyl)-3-(2-methyl-pyridin-4-yl)-7-trifluoromethyl-pyrazolo[1,5-a]pyrimidine,
5-(4-trifluoroethoxy-3-trifluoromethyl-phenyl)-3-(2-methyl-pyridin-4-yl)-7-trifluoromethyl-pyrazolo[1,5-a]pyrimidine,
5-(3-methyl-4-trifluoromethyl-phenyl)-3-(2-hydroxymethyl-pyridin-4-yl)-7-trifluoromethyl-pyrazolo[1,5-a]pyrimidine, and
5-(4-chloro-3-methyl-phenyl)-3-(2-methyl-1-oxy-pyridin-4-yl)-7-trifluoromethyl-pyrazolo[1,5-a]pyrimidine.

In another embodiment, the present invention provides a compound of formula I selected from
2-(4-Chloro-3-methyl-phenyl)-8-pyridin-3-yl-4-trifluoromethyl-imidazo[1,5-a]pyrimidine,
2-(3-Chloro-4-fluoro-phenyl)-8-pyridin-3-yl-4-trifluoromethyl-imidazo[1,5-a]pyrimidine,
2-(4-Dichloro-phenyl)-8-pyridin-3-yl-4-trifluoromethyl-imidazo[1,5-a]pyrimidine,
8-Pyridin-3-yl-4-trifluoromethyl-2-(4-trifluoromethyl-phenyl)-imidazo[1,5-a]pyrimidine,
2-(3-Methyl-4-trifluoromethyl-phenyl)-8-pyridin-3-yl-4-trifluoromethyl-imidazo[1,5-a]pyrimidine,
2-(4-Chloro-3-methyl-phenyl)-8-pyridin-4-yl-4-trifluoromethyl-imidazo[1,5-a]pyrimidine,
2-(3-Chloro-4-fluoro-phenyl)-8-pyridin-4-yl-4-trifluoromethyl-imidazo[1,5-a]pyrimidine,
2-(4-Dichloro-phenyl)-8-pyridin-4-yl-4-trifluoromethyl-imidazo[1,5-a]pyrimidine,
8-Pyridin-4-yl-4-trifluoromethyl-2-(3-trifluoromethyl-phenyl)-imidazo[1,5-a]pyrimidine, and
8-Pyridin-4-yl-4-trifluoromethyl-2-(4-trifluoromethyl-phenyl)-imidazo[1,5-a]pyrimidine.

In another embodiment, the present invention provides a compound of formula I selected from
2-(4-Methyl-3-trifluoromethyl-phenyl)-8-pyridin-4-yl-4-trifluoromethyl-imidazo[1,5-a]pyrimidine,
2-(4-Ethoxy-3-trifluoromethyl-phenyl)-8-pyridin-4-yl-4-trifluoromethyl-imidazo[1,5-a]pyrimidine,
8-Pyridin-4-yl-2-[4-(2,2,2-trifluoro-ethoxy)-3-trifluoromethyl-phenyl]-4-trifluoromethyl-imidazo[1,5-a]pyrimidine,
2-(3-Methyl-4-trifluoromethyl-phenyl)-8-pyridin-4-yl-4-trifluoromethyl-imidazo[1,5-a]pyrimidine,
2-(4-Chloro-phenyl)-8-(2-methyl-pyridin-4-yl)-4-trifluoromethyl-imidazo[1,5-a]pyrimidine,
2-(3-Chloro-4-fluoro-phenyl)-8-(2-methyl-pyridin-4-yl)-4-trifluoromethyl-imidazo[1,5-a]pyrimidine,
2-(4-Dichloro-phenyl)-8-(2-methyl-pyridin-4-yl)-4-trifluoromethyl-imidazo[1,5-a]pyrimidine,
8-(2-Methyl-pyridin-4-yl)-4-trifluoromethyl-2-(4-trifluoromethyl-phenyl)-imidazo[1,5-a]pyrimidine,
2-(4-Ethoxy-3-trifluoromethyl-phenyl)-8-(2-methyl-pyridin-4-yl-4-trifluoromethyl-imidazo[1,5-a]pyrimidine, and
8-(2-Methyl-pyridin-4-yl-2-[4-(2,2,2-trifluoro-ethoxy)-3-trifluoromethyl-phenyl]-4-trifluoromethyl-imidazo[1,5-a]pyrimidine.

In another embodiment, the present invention provides a compound of formula I selected from
2-(3-Methyl-4-trifluoromethyl-phenyl)-8-(2-methyl-pyridin-4-yl)-4-trifluoromethyl-imidazo[1,5-a]pyrimidine,
{4-[5-(4-Chloro-3-methyl-phenyl)-7-trifluoromethyl-pyrazolo[1,5-a]pyrimidin-3-yl]-pyridin-2-yl}-methanol,
{4-[5-(3,4-Dichloro-phenyl)-7-trifluoromethyl-pyrazolo[1,5-a]pyrimidin-3-yl]-pyridin-2-yl}-methanol,
5-(3-Ethoxy-4-trifluoromethyl-phenyl)-3-pyridin-4-yl-7-trifluoromethyl-pyrazolo[1,5-a]pyrimidine,
5-(3-Ethoxy-4-trifluoromethyl-phenyl)-3-(2-methyl-pyridin-4-yl)-7-trifluoromethyl-pyrazolo[1,5-a]pyrimidine,
2-(3-Ethoxy-4-trifluoromethyl-phenyl)-8-pyridin-4-yl-4-trifluoromethyl-imidazo[1,5-a]pyrimidine,
3-Pyridin-4-yl-5-[3-(2,2,2-trifluoro-ethoxy)-4-trifluoromethyl-phenyl]-7-trifluoromethyl-pyrazolo[1,5-a]pyrimidine,
3-(2,6-Dimethyl-pyridin-4-yl)-5-[3-(2,2,2-trifluoro-ethoxy)-4-trifluoromethyl-phenyl]-7-trifluoromethyl-pyrazolo[1,5-a]pyrimidine,
3-(2-Methyl-pyridin-4-yl)-5-[3-(2,2,2-trifluoro-ethoxy)-4-trifluoromethyl-phenyl]-7-trifluoromethyl-pyrazolo[1,5-a]pyrimidine, and
8-Pyridin-4-yl-2-[3-(2,2,2-trifluoro-ethoxy)-4-trifluoromethyl-phenyl]-4-trifluoromethyl-imidazo[1,5-a]pyrimidine.

In another embodiment, the present invention provides a compound of formula I selected from
8-(2-Methyl-pyridin-4-yl)-2-[3-(2,2,2-trifluoro-ethoxy)-4-trifluoromethyl-phenyl]-4-trifluoromethyl-imidazo[1,5-a]pyrimidine,
5-(3,4-Bis-trifluoromethyl-phenyl)-3-pyridin-4-yl-7-trifluoromethyl-pyrazolo[1,5-a]pyrimidine,
5-(3,4-Bis-trifluoromethyl-phenyl)-3-(2-methyl-pyridin-4-yl)-7-trifluoromethyl-pyrazolo[1,5-a]pyrimidine,
2-(3,4-Bis-trifluoromethyl-phenyl)-8-(2-methyl-pyridin-4-yl)-4-trifluoromethyl-imidazo[1,5-a]pyrimidine,
2-(4-Bromo-phenyl)-8-(2-methyl-pyridin-4-yl)-4-trifluoromethyl-imidazo[1,5-a]pyrimidine,
5-(4-Bromo-phenyl)-3-pyridin-4-yl-7-trifluoromethyl-pyrazolo[1,5-a]pyrimidine,
5-(4-Bromo-phenyl)-3-(2-methyl-pyridin-4-yl)-7-trifluoromethyl-pyrazolo[1,5-a]pyrimidine,
7-Difluoromethyl-3-pyridin-4-yl-5-(4-trifluoromethyl-phenyl)-pyrazolo[1,5-a]pyrimidine,
7-Difluoromethyl-3-(2-methyl-pyridin-4-yl)-5-(4-trifluoromethyl-phenyl)-pyrazolo[1,5-a]pyrimidine, and
7-Difluoromethyl-3-(2-methyl-pyridin-4-yl)-5-(3-methyl-4-trifluoromethyl-phenyl)-pyrazolo[1,5-a]pyrimidine.

In another embodiment, the present invention provides a compound of formula I selected from
5-(4-chloro-3-methyl-phenyl)-7-trifluoromethyl-pyrazolo[1,5-a]pyrimidine-3-carbonitrile,
5-(4-chloro-phenyl)-3-pyridin-4-yl-7-trifluoromethyl-pyrazolo[1,5-a]pyrimidine, 5-(4-chloro-3-methyl-phenyl)-3-pyridin-4-yl-7-trifluoromethyl-pyrazolo[1,5-a]pyrimidine,
5-(3-chloro-4-fluoro-phenyl)-3-pyridin-4-yl-7-trifluoromethyl-pyrazolo[1,5-a]pyrimidine,
5-(4-trifluoromethyl-phenyl)-3-pyridin-4-yl-7-trifluoromethyl-pyrazolo[1,5-a]pyrimidine,
5-(3-trifluoromethyl-phenyl)-3-pyridin-4-yl-7-trifluoromethyl-pyrazolo[1,5-a]pyrimidine,
5-(3-fluoro-4-trifluoromethyl-phenyl)-3-pyridin-4-yl-7-trifluoromethyl-pyrazolo[1,5-a]pyrimidine,
5-(4-chloro-3-methyl-phenyl)-3-(2,6-dimethyl-pyridin-4-yl)-7-trifluoromethyl-pyrazolo[1,5-a]pyrimidine,
5-(3,4-dichloro-phenyl)-3-(2,6-dimethyl-pyridin-4-yl)-7-trifluoromethyl-pyrazolo[1,5-a]pyrimidine, and
5-(3-fluoro-4-trifluoromethyl-phenyl)-3-(2,6-dimethyl-pyridin-4-yl)-7-trifluoromethyl-pyrazolo[1,5-a]pyrimidine.

In another embodiment, the present invention provides a compound of formula I selected from
5-(4-chloro-phenyl)-3-(2-methyl-pyridin-4-yl)-7-trifluoromethyl-pyrazolo[1,5-a]pyrimidine,
5-(3,4-dichloro-phenyl)-3-(2-methyl-pyridin-4-yl)-7-trifluoromethyl-pyrazolo[1,5-a]pyrimidine,
5-(4-trifluoromethyl-phenyl)-3-(2-methyl-pyridin-4-yl)-7-trifluoromethyl-pyrazolo[1,5-a]pyrimidine,
5-(3-trifluoromethyl-phenyl)-3-(2-methyl-pyridin-4-yl)-7-trifluoromethyl-pyrazolo[1,5-a]pyrimidine,
5-(3-methyl-4-trifluoromethyl-phenyl)-3-pyridin-4-yl-7-trifluoromethyl-pyrazolo[1,5-a]pyrimidine,
5-(3-methyl-4-trifluoromethyl-phenyl)-3-(2,6-dimethyl-pyridin-4-yl)-7-trifluoromethyl-pyrazolo[1,5-a]pyrimidine,
5-(3-methyl-4-trifluoromethyl-phenyl)-3-(2-methyl-pyridin-4-yl)-7-trifluoromethyl-pyrazolo[1,5-a]pyrimidine, and
5-(4-ethoxy-3-trifluoromethyl-phenyl)-3-pyridin-4-yl-7-trifluoromethyl-pyrazolo[1,5-a]pyrimidine.

The present invention also provides a process for the preparation of a compound of formula I comprising reacting a compound of formula II

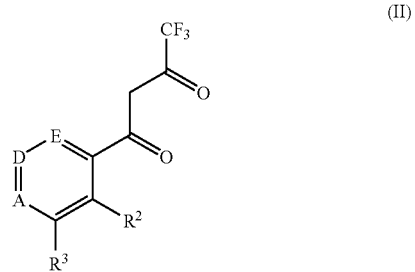

(II)

wherein
A is =$C(R^4)$—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine,
D is =$C(R^5)$—, wherein $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine,
E is =$C(R^6)$—, wherein $R^6$ is hydrogen or halogen, or one of A, D and E is =N—,
$R^2$ is selected from hydrogen, halogen, ($C_1$-$C_4$)-alkyl and ($C_3$-$C_6$)-cycloalkyl, and
$R^3$ is selected from hydrogen, halogen, ($C_1$-$C_4$)-alkyl and ($C_3$-$C_6$)-cycloalkyl,
with a compound of formula III

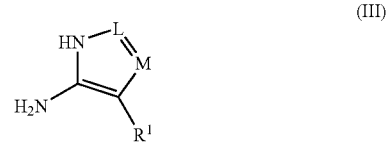

(III)

wherein
L is =N— or =C(H)—,
M is =$C(R^7)$—, when L is =N—, or M is =N—, when L is =C(H)—,
$R^1$ is selected from —CN, unsubstituted pyridinyl, pyridinyl substituted by ($C_1$-$C_4$)-alkyl and the corresponding pyridine-N-oxide of pyridinyl substituted by ($C_1$-$C_4$)-alkyl, and
$R^7$ is selected from hydrogen, unsubstituted ($C_1$-$C_4$)-alkyl, ($C_1$-$C_4$)-alkyl substituted by CN, unsubstituted ($C_3$-$C_6$)-cycloalkyl and ($C_3$-$C_6$)-cycloalkyl substituted by CN.

The starting compounds of formula II and III are known or may be prepared from corresponding known compounds.

The reaction may take place in the presence of a solvent, e.g. acetic acid, under, e.g., reflux conditions. The preparation of compounds of formula I is illustrated in the following examples.

EXAMPLE S1

Preparation of
1-phenyl-4,4,4-trifluoro-butane-1,3-diones (General Procedure A)

To a stirred solution of ethyl trifluoroacetate (1.1 eq.) in tert-butyl-methyl-ether was added dropwise a 5.4M solution of sodium methanolate in methanol followed by a solution of an acetophenone derivative (1.1 eq.) in tert-butyl-methyl-ether. The reaction mixture was stirred at room temperature for 20 h, poured into ice/water, acidified with 2N HCl and extracted with diethyl ether (two times). The combined organic layers were washed with brine (two times), dried (MgSO$_4$) and evaporated. The product was used without further purification.

| acetophenone derivative | resulting 1-phenyl-4,4,4-trifluoro-butane-1,3-dione | No. |
|---|---|---|
| 3-chloro-acetophenone | 1-(3-chloro-phenyl)-4,4,4-trifluoro-butane-1,3-dione | S1.1 |
| 4-methyl-acetophenone | 1-(4-methyl-phenyl)-4,4,4-trifluoro-butane-1,3-dione | S1.2 |

-continued

| acetophenone derivative | resulting 1-phenyl-4,4,4-trifluoro-butane-1,3-dione | No. |
|---|---|---|
| 2-chloro-acetophenone | 1-(2-chloro-phenyl)-4,4,4-trifluoro-butane-1,3-dione | S1.3 |
| 2,4-dichloro-acetophenone | 1-(2,4-dichloro-phenyl)-4,4,4-trifluoro-butane-1,3-dione | S1.4 |
| 3-methyl-acetophenone | 1-(3-methyl-phenyl)-4,4,4-trifluoro-butane-1,3-dione | S1.5 |
| 3-trifluoromethyl-acetophenone | 1-(3-trifluoromethyl-phenyl)-4,4,4-trifluoro-butane-1,3-dione | S1.6 |
| 4-trifluoromethyl-acetophenone | 1-(4-trifluoromethyl-phenyl)-4,4,4-trifluoro-butane-1,3-dione | S1.7 |
| 3-fluoro-acetophenone | 1-(3-fluoro-phenyl)-4,4,4-trifluoro-butane-1,3-dione | S1.8 |
| 4-fluoro-acetophenone | 1-(4-fluoro-phenyl)-4,4,4-trifluoro-butane-1,3-dione | S1.9 |
| 2,4-difluoro-acetophenone | 1-(2,4-difluoro-phenyl)-4,4,4-trifluoro-butane-1,3-dione | S1.10 |
| 2-fluoro-acetophenone | 1-(2-fluoro-phenyl)-4,4,4-trifluoro-butane-1,3-dione | S1.11 |
| 3,4-difluoro-acetophenone | 1-(3,4-difluoro-phenyl)-4,4,4-trifluoro-butane-1,3-dione | S1.12 |
| 4-fluoro-3-trifluoromethyl-acetophenone | 1-(4-fluoro-3-trifluoromethyl-phenyl)-4,4,4-trifluoro-butane-1,3-dione | S1.13 |
| 3-chloro-4-fluoro-acetophenone | 1-(3-chloro-4-fluoro-phenyl)-4,4,4-trifluoro-butane-1,3-dione | S1.14 |
| 4-chloro-3-methyl-acetophenone | 1-(4-chloro-3-methyl-phenyl)-4,4,4-trifluoro-butane-1,3-dione | S1.15 |
| 3,4-dichloro-acetophenone | 1-(3,4-dichloro-phenyl)-4,4,4-trifluoro-butane-1,3-dione | S1.16 |
| 4-chloro-acetophenone | 1-(4-chloro-phenyl)-4,4,4-trifluoro-butane-1,3-dione | S1.17 |
| 3-fluoro-4-trifluoromethyl-acetophenone | 1-(3-fluoro-4-trifluoromethyl-phenyl)-4,4,4-trifluoro-butane-1,3-dione | S1.18 |
| 3-methyl-4-trifluoromethyl-acetophenone | 1-(3-methyl-4-trifluoromethyl-phenyl)-4,4,4-trifluoro-butane-1,3-dione | S1.19 |
| 4-trifluoroethoxy-3-trifluoromethyl-acetophenone | 1-(4-trifluoroethoxy-3-trifluoromethyl-phenyl)-4,4,4-trifluoro-butane-1,3-dione | S1.20 |
| 4-methyl-3-trifluoromethyl-acetophenone | 1-(4-methyl-3-trifluoromethyl-phenyl)-4,4,4-trifluoro-butane-1,3-dione | S1.21 |
| 4-ethoxy-3-trifluoromethyl-acetophenone | 1-(4-ethoxy-3-trifluoromethyl-phenyl)-4,4,4-trifluoro-butane-1,3-dione | S1.22 |
| acetophenone | 1-phenyl-4,4,4-trifluoro-butane-1,3-dione | S1.23 |
| 4-methoxy-acetophenone | 1-(4-methoxy-phenyl)-4,4,4-trifluoro-butane-1,3-dione | S1.24 |
| 2-methyl-acetophenone | 1-(2-methyl-phenyl)-4,4,4-trifluoro-butane-1,3-dione | S1.25 |
| 3-ethoxy-4-trifluoromethyl-acetophenone | 1-(3-ethoxy-4-trifluoromethyl-phenyl)-4,4,4-trifluoro-butane-1,3-dione | S1.26 |
| 3-(2,2,2-trifluoroethoxy)-4-trifluoromethyl-acetophenone | 1-[3-(2,2,2-trifluoroethoxy)-4-trifluoromethyl-phenyl]-4,4,4-trifluoro-butane-1,3-dione | S1.27 |
| 3,4-bis-trifluoromethyl-acetophenone | 1-(3,4-bis-trifluoromethyl-phenyl)-4,4,4-trifluoro-butane-1,3-dione | S1.28 |
| 4-bromo-acetophenone | 1-(4-bromo-phenyl)-4,4,4-trifluoro-butane-1,3-dione | S1.29 |
| 4-methoxy-acetophenone | 4,4-difluoro-1-(4-methoxy-phenyl)-butane-1,3-dione | S1.30 |

No.: compound number of resulting 1-phenyl-4,4,4-trifluoro-butane-1,3-dione

EXAMPLE S2

Preparation of
1-pyridinyl-4,4,4-trifluoro-butane-1,3-diones (General Procedure A)

To a stirred solution of ethyl trifluoroacetate (1.1 eq.) in tert-butyl-methyl-ether was added dropwise a 5.4M solution of sodium methanolate in methanol followed by a solution of an acetylpyridine derivative (1.1 eq.) in tert-butyl-methyl-ether. The reaction mixture was stirred at room temperature for 20 h, poured into ice/water, acidified with 2N HCl and extracted with diethyl ether (two times). The combined organic layers were washed with water (20 ml), the combined water layers neutralized with sat. NaHCO$_3$ solution and evaporated to dryness. The obtained solid was stirred three times in warm dichloromethane/MeOH 9:1 and filtered. The combined organic layers were dried (MgSO$_4$) and evaporated. The crude product can be further purified by crystallization.

| acetylpyridine derivative | resulting 1-phenyl-4,4,4-trifluoro-butane-1,3-dione | No. |
| --- | --- | --- |
| 2-acetylpyridine | 1-pyridin-2-yl-4,4,4-trifluoro-butane-1,3-dione | S2.1 |
| 3-acetylpyridine | 1-pyridin-3-yl-4,4,4-trifluoro-butane-1,3-dione | S2.2 |
| 4-acetylpyridine | 1-pyridin-4-yl-4,4,4-trifluoro-butane-1,3-dione | S2.3 |

EXAMPLE S3

Preparation of 3-amino-pyridinyl-pyrazoles

Following a procedure as described in Bioorg. Med. Chem. Lett. 12 (2002) 3537-3541] the following 3-amino-pyridinyl-pyrazoles were prepared starting from the appropriate pyridine:

| pyridine | resulting 3-amino-pyridinyl-pyrazole [CAS No.] | No. |
| --- | --- | --- |
| 3-cyanomethyl-pyridine | 3-amino-4-(3-pyridinyl)-pyrazole [40545-68-2] | S3.1 |
| 4-cyanomethyl-pyridine | 3-amino-4-(4-pyridinyl)-pyrazole [216661-87-9] | S3.2 |
| 2-cyanomethyl-pyridine | 3-amino-4-(2-pyridinyl)-pyrazole [493038-87-2] | S3.3 |
| 4-cyanomethyl-2,6-dimethyl-pyridine [130138-46-4] | 3-amino-4-(2,6-dimethyl-4-pyridinyl)-pyrazole | S3.4 |
| 4-cyanomethyl-2-methyl-pyridine [130138-46-4] | 3-amino-4-(2-methyl-4-pyridinyl)-pyrazole | S3.5 |

No.: compound number of resulting 3-amino-pyridinyl-pyrazole

EXAMPLE S4

Preparation of 4-(2-Methyl-pyridin-4-yl)-2H-pyrazol-3-ylamine

To a stirred mixture of 4-hydroxymethyl-2-methyl-pyridine [CAS No. 105250-16-6] (3.37 g, 27.4 mmol), potassium cyanide (3.56 g, 54.7 mmol) and 18-crown-6 (0.72 g, 2.74 mmol) in acetonitrile (75 ml) was added dropwise at 15-20° C. a solution of tributylphosphine (7.16 g, 30.1 mmol) in acetonitrile (25 ml). The reaction mixture was stirred at room temperature for 25 h, poured into water (100 ml) and extracted with ethyl acetate (3×100 ml). The combined organic layers were washed with water (3×100 ml), brine (100 ml) dried (MgSO$_4$) and evaporated. The crude product was further purified by column chromatography on silica gel (ethyl acetate) to yield 4-cyanomethyl-2-methyl-pyridine (2.26 g, 62%) as a brown oil.

A stirred mixture of 4-cyanomethyl-2-methyl-pyridine (2.51 g, 19.0 mmol) and N,N-dimethylformamide-dimethylacetal (7.63 ml, 57.0 mmol) was heated under reflux conditions for 15 min, evaporated and the crude product purified by column chromatography on silica gel (dichloromethane/methanol/NH4OH 80:10:1) to give 2.08 g of a solid, which was crystallized from diethyl ether/hexane to yield 3-dimethylamino-2-(2-methyl-pyridin-4-yl)-acrylonitrile (1.94 g, 55%) as a brown solid; mp 126° C.

c) To stirred solution of 3-dimethylamino-2-(2-methyl-pyridin-4-yl)-acrylonitrile (1.8 g, 9.61 mmol) in ethanol (18 ml) was added at room temperature hydrazine monohydrate (1.03 ml, 21.1 mmol), the reaction mixture was heated under reflux conditions for 16 h and evaporated. Purification by column chromatography on silica gel (dichloromethane/methanol/NH4OH 80:10:1) and crystallization from diethyl ether yielded 4-(2-methyl-pyridin-4-yl)-2H-pyrazol-3-ylamine (0.6 g, 36%) as an orange solid.

MS (ISP) 175.1 [(M+H)$^+$]; mp 230° C.

EXAMPLE S5

Preparation of 4-(2,6-Dimethyl-pyridin-4-yl)-2H-pyrazol-3-ylamine

A stirred mixture of 4-cyanomethyl-2,6-dimethyl-pyridine [CAS No. 130138-46-4] (2.20 g, 15.1 mmol) and N,N-dimethylformamide-dimethylacetal (6.04 ml, 45.2 mmol) was heated under reflux conditions for 15 min, evaporated and the crude product purified by column chromatography on silica gel (dichloromethane/methanol/NH$_4$OH 80:10:1) to give 2.6 g of a solid, which was crystallized from diethyl ether/hexane to yield 3-dimethylamino-2-(2,6-dimethyl-pyridin-4-yl)-acrylonitrile (2.44 g, 81%) as a brown solid; mp 149° C.

b) To stirred solution of 3-dimethylamino-2-(2,6-dimethyl-pyridin-4-yl)-acrylonitrile (2.2 g, 10.9 mmol) in ethanol (22 ml) was added at room temperature hydrazine monohydrate (1.17 ml, 24.1 mmol), the reaction mixture was heated under reflux conditions for 23 h and evaporated. Purification by column chromatography on silica gel (dichloromethane/methanol/NH$_4$OH 80:10:1) and crystallization from diethyl ether yielded 4-(2,6-dimethyl-pyridin-4-yl)-2H-pyrazol-3-ylamine (0.8 g, 39%) as a light brown solid. MS (ISP) 189.3 [(M+H)$^+$]; mp 222° C.

EXAMPLE S6

2-Amino-3-(3-pyridinyl)-1H-imidazole dihydrochloride

To a stirred solution of sulfuric acid (14 ml, 95-97%) and HNO$_3$ (10 ml, fum.) was added at 0° C. 3-(3-pyridinyl)-1H-imidazole [CAS No. 51746-85-1, commercially available] (4.25 g, 29.3 mmol). The reaction mixture was stirred at room temperature for 45 min and at 50° C. for 6 h and poured into ice-water (100 ml). Solid NaHCO$_3$ was added to the stirred mixture until the pH reached 5-6, the precipitated product was collected by filtration and washed with water and hexane to yield 2-nitro-3-(3-pyridinyl)-1H-imidazole (5.53 g, 99%) as an off-white solid; mp 261° C.

b) A stirred solution of 2-nitro-3-(3-pyridinyl)-1H-imidazole (5.14 g, 27.0 mmol) in methanol (800 ml) was hydrogenated at room temperature on Raney Nickel (2.5 g) for 4 h. The catalyst was removed by filtration, 3N hydrochloric acid (30 ml) was added and the solution evaporated to 50 ml. While stirring diethyl ether was added and the precipitated product was collected by filtration to yield 2-amino-3-(3-pyridinyl)-1H-imidazole dihydrochloride (5.39 g, 86%) as a brown solid. MS (ISP) 161.2 [(M+H)$^+$]; mp 253° C.

EXAMPLE S7

2-Amino-3-(4-pyridinyl)-1H-imidazole

To a stirred solution of sulfuric acid (21 ml, 95-97%) and HNO$_3$ (15 ml, fum.) was added at 0° C. 3-(4-pyridinyl)-1H-imidazole [CAS No. 51746-87-3] (6.36 g, 43.8 mmol). The reaction mixture was stirred at room temperature for 45 min, at 55° C. for 23 h and at 100° C. for 2 h and poured into ice-water (200 ml). Sodium hydroxide solution (32%) was added to the stirred mixture until the pH reached 5-6, the precipitated product was collected by filtration and washed with water and hexane to yield 2-nitro-3-(4-pyridinyl)-1H-imidazole (7.95 g, 95%) as a light yellow solid; mp 234° C.

b) A stirred solution of 2-nitro-3-(4-pyridinyl)-1H-imidazole (1.19 g, 6.26 mmol) in 7N methanol/NH$_3$ (25 ml) and methanol (25 ml) was hydrogenated at room temperature on Raney Nickel (1 g) for 4 h. The catalyst was removed by filtration and the solution evaporated. The crude product was purified by column chromatography on silica gel (dichloromethane/methanol/NH$_4$OH 40:10:1) to yield 2-amino-3-(4-pyridinyl)-1H-imidazole (0.85 g, 85%) as a green solid. MS (ISP) 161.2 [(M+H)$^+$]; mp 190° C.

EXAMPLE S8

2-Amino-3-(2-methyl-4-pyridinyl)-1H-imidazole

To a stirred suspension of 4-acetyl-2-methyl-pyridine [CAS No. 2732-28-7] (9.7 g, 71.8 mmol) in water (115 ml) was added at room temperature hydroxylamine hydrochloride (8.48 g, 122 mmol) and the mixture was heated to 70° C. At this temperature methanol (145 ml) was added dropwise over a period of 15 min and afterwards a solution of sodium acetate trihydrate (25.4 g, 187 mmol) in water (115 ml) was added dropwise over a period of 15 min. The reaction mixture was stirred at 80° C. for 3.5 h, brine (150 ml) was added and the solution was extracted with ethyl acetate (2×250 ml). The combined organic layers were washed with brine (150 ml), dried (MgSO$_4$) and evaporated. The crude product was purified by crystallization from ethyl acetate/hexane to give 1-(2-methyl-pyridin-4-yl)-ethanone oxime (7.25 g, 67%) as an off-white solid; mp 154° C.

b) To a stirred solution of 1-(2-methyl-pyridin-4-yl)-ethanone oxime (7.14 g, 47.5 mmol) in pyridine (20 ml) was added at room temperature toluene-4-sulfonyl chloride (9.88 g, 51.8 mmol), the reaction mixture was stirred for 3 h, poured into ice-water (300 ml) and the precipitated solid collected by filtration. Hexane (100 ml) was added, the mixture was stirred at room temperature for 1 h and the product collected by filtration to give 1-(2-methyl-pyridin-4-yl)-(O-toluene-4-sulfonyl)-ethanone oxime (11.1 g, 77%) as a white solid; mp 91° C.

c) To a stirred suspension of 1-(2-methyl-pyridin-4-yl)-(O-toluene-4-sulfonyl)-ethanone oxime (11.0 g, 36.1 mmol) in ethanol (35 ml) was added a solution of potassium ethanolate (5.03 g, 56.7 mmol) in ethanol (35 ml) and the reaction mixture was stirred at room temperature for 17 h. The precipitated solid was collected by filtration and washed with diethyl ether (200 ml). The combined filtrates were washed with 2N HCl (2×80 ml, 1×40 ml) and the combined water layers evaporated to give crude 1-(2-methyl-pyridin-4-yl)-2-amino-ethanone dihydrochloride (8.51 g, 99%) as a light brown solid, which was used without further purification.

d) To a stirred solution of crude 1-(2-methyl-pyridin-4-yl)-2-amino-ethanone dihydrochloride (8.50 g, 35.8 mmol) in water (60 ml) was added at room temperature potassium thiocyanate (16.4 g, 168 mmol) and the reaction mixture was heated under reflux conditions for 3 h and at 0° C. for 2 h. The precipitated solid was collected by filtration, saturated sodium bicarbonate solution (100 ml) was added and the mixture was stirred at room temperature for 2 h. The product was collected by filtration to give 4-(2-methyl-pyridin-4-yl)-1,3-dihydro-imidazole-2-thione (5.44 g, 79%) as a light brown solid; MS (ISP) 192.2 [(M+H)$^+$].

e) To a stirred solution of HNO$_3$ (43.3 ml, 65%) and water (130 ml) was added at 80° C. in small portions 4-(2-methyl-pyridin-4-yl)-1,3-dihydro-imidazole-2-thione (5.20 g, 27.2 mmol) and the mixture was heated under reflux conditions for 2 h. The reaction mixture was cooled (ice) and solid NaHCO$_3$ was added to get a basic solution. Solid NaCl was added and the solution was extracted with THF (3×200 ml). The combined organic layers were dried (MgSO$_4$) and evaporated to give 3-(2-methyl-4-pyridinyl)-1H-imidazole (4.16 g, 96%) as a yellow solid; MS (ISP) 160.2 [(M+H)$^+$].

f) To a stirred solution of sulfuric acid (14 ml, 95-97%) and HNO$_3$ (10 ml, fum.) was added at 0° C. 3-(2-methyl-4-pyridinyl)-1H-imidazole (4.0 g, 25.1 mmol). The reaction mixture was stirred at room temperature for 50 min, at 100° C. for 2.5 h and at 110° C. for 10 h and poured into ice-water (70 ml). Solid NaHCO$_3$ was added to the stirred mixture until the pH reached 5. The solution was extracted with THF (4×200 ml), the combined organic layers were dried (MgSO4) and evaporated to give 2-nitro-3-(2-methyl-4-pyridinyl)-1H-imidazole (3.4 g, 66%) as a light yellow solid; MS (ISP) 205.2 [(M+H)$^+$].

g) A stirred solution of 2-nitro-3-(2-methyl-4-pyridinyl)-1H-imidazole (3.40 g, 16.6 mmol) in 7N methanol/NH$_3$ (70 ml) and methanol (70 ml) was hydrogenated at room temperature on Raney Nickel (2.9 g) for 2 h. The catalyst was removed by filtration and the solution evaporated. The crude product was purified by column chromatography on silica gel (dichloromethane/methanol/NH$_4$OH 40:10:1) to yield 2-amino-3-(2-methyl-4-pyridinyl)-1H-imidazole (1.71 g, 59%) as a green solid. MS (ISP) 175.1 [(M+H)$^+$]; mp 167° C.

EXAMPLE 1

Preparation of phenyl-7-trifluoromethyl-pyrazolo[1,5-a]pyrimidine-3-carbonitriles and pyridinyl-7-trifluoromethyl-pyrazolo[1,5-a]pyrimidine-3-carbonitriles (General Procedure B)

A stirred mixture of commercially available 3-amino-4-cyano-pyrazole (1 eq.) and a 1-phenyl-4,4,4-trifluoro-butane-1,3-dione or 1-pyridin-2-yl-4,4,4-trifluoro-butane-1,3-dione (1 eq.), prepared according to general procedure A, in acetic acid was heated under reflux conditions for 3.5 h. The reaction mixture was evaporated and the product was isolated by column chromatography (heptane/ethyl acetate) and further purified by crystallization. If the product precipitates during the reaction it can be isolated by filtration and further purified by crystallization.

EXAMPLE 1.1

5-(3-Chloro-phenyl)-7-trifluoromethyl-pyrazolo[1,5-a]pyrimidine-3-carbonitrile

Reaction of 1-(3-chloro-phenyl)-4,4,4-trifluoro-butane-1,3-dione (251 mg, 1.0 mmol), prepared from commercially available 3-chloro-acetophenone according to general procedure A, and 3-amino-4-cyano-pyrazole (108 mg, 1.0 mmol) according to general procedure B yielded the title compound as a yellow solid (150 mg, 46%). MS (ISP) 323.1 [(M+H)$^+$]; mp 204° C.

EXAMPLE 1.2

5-(4-Methyl-phenyl)-7-trifluoromethyl-pyrazolo[1,5-a]pyrimidine-3-carbonitrile

Reaction of 1-(4-methyl-phenyl)-4,4,4-trifluoro-butane-1,3-dione (230 mg, 1.0 mmol), prepared from commercially

| Ex. | dione | compound name | MS (ISP)/mp |
|---|---|---|---|
| 1.1 | S1.1 | 5-(3-chloro-phenyl)-7-trifluoromethyl-pyrazolo[1,5-a]pyrimidine-3-carbonitrile | 323.1 [(M + H)$^+$] mp 204° C. |
| 1.2 | S1.2 | 5-(4-methyl-phenyl)-7-trifluoromethyl-pyrazolo[1,5-a]pyrimidine-3-carbonitrile | 303.1 [(M + H)$^+$] mp 121° C. |
| 1.3 | S1.3 | 5-(2-chloro-phenyl)-7-trifluoromethyl-pyrazolo[1,5-a]pyrimidine-3-carbonitrile | 323.1 [(M + H)$^+$] mp 169° C. |
| 1.4 | S1.4 | 5-(2,4-dichloro-phenyl)-7-trifluoromethyl-pyrazolo[1,5-a]pyrimidine-3-carbonitrile | 357.1 [(M + H)$^+$] mp 180° C. |
| 1.5 | S1.5 | 5-(3-methyl-phenyl)-7-trifluoromethyl-pyrazolo[1,5-a]pyrimidine-3-carbonitrile | 303.2 [(M + H)$^+$] mp 202° C. |
| 1.6 | S1.6 | 5-(3-trifluoromethyl-phenyl)-7-trifluoromethyl-pyrazolo[1,5-a]pyrimidine-3-carbonitrile | 357.0 [(M + H)$^+$] mp 192° C. |
| 1.7 | S1.7 | 5-(4-trifluoromethyl-phenyl)-7-trifluoromethyl-pyrazolo[1,5-a]pyrimidine-3-carbonitrile | 357.0 [(M + H)$^+$] mp 176° C. |
| 1.8 | S1.8 | 5-(3-fluoro-phenyl)-7-trifluoromethyl-pyrazolo[1,5-a]pyrimidine-3-carbonitrile | 306.9 [(M + H)$^+$] mp 199° C. |
| 1.9 | S1.9 | 5-(4-fluoro-phenyl)-7-trifluoromethyl-pyrazolo[1,5-a]pyrimidine-3-carbonitrile | 306.9 [(M + H)$^+$] mp 198° C. |
| 1.10 | S1.10 | 5-(2,4-difluoro-phenyl)-7-trifluoromethyl-pyrazolo[1,5-a]pyrimidine-3-carbonitrile | 325.0 [(M + H)$^+$] mp 149° C. |
| 1.11 | S1.11 | 5-(2-fluoro-phenyl)-7-trifluoromethyl-pyrazolo[1,5-a]pyrimidine-3-carbonitrile | 307.1 [(M + H)$^+$] mp 165° C. |
| 1.12 | S1.12 | 5-(3,4-difluoro-phenyl)-7-trifluoromethyl-pyrazolo[1,5-a]pyrimidine-3-carbonitrile | 325.0 [(M + H)$^+$] mp 192° C. |
| 1.13 | S1.13 | 5-(4-fluoro-3-trifluoromethyl-phenyl)-7-trifluoromethyl-pyrazolo[1,5-a]pyrimidine-3-carbonitrile | 375.0 [(M + H)$^+$] mp 204° C. |
| 1.14 | S1.14 | 5-(3-chloro-4-fluoro-phenyl)-7-trifluoromethyl-pyrazolo[1,5-a]pyrimidine-3-carbonitrile | 341.0 [(M + H)$^+$] mp 190° C. |
| 1.15 | S1.15 | 5-(4-chloro-3-methyl-phenyl)-7-trifluoromethyl-pyrazolo[1,5-a]pyrimidine-3-carbonitrile | 337.1 [(M + H)$^+$] mp 216° C. |
| 1.16 | S1.16 | 5-(3,4-dichloro-phenyl)-7-trifluoromethyl-pyrazolo[1,5-a]pyrimidine-3-carbonitrile | 356.9 [(M + H)$^+$] mp 206° C. |
| 1.17 | S1.18 | 5-(3-fluoro-4-trifluoromethyl-phenyl)-7-trifluoromethyl-pyrazolo[1,5-a]pyrimidine-3-carbonitrile | 375.0 [(M + H)$^+$] mp 184° C. |
| 1.18 | S1.19 | 2-(3-methyl-4-trifluoromethyl-phenyl)-4-trifluoromethyl-pyrazolo[1,5-a]pyrimidine-8-carbonitrile | 371.1 [(M + H)$^+$] mp 209° C. |
| 1.19 | S1.20 | 2-(4-trifluoroethoxy-3-trifluoromethyl-phenyl)-4-trifluoromethyl-pyrazolo[1,5-a]pyrimidine-8-carbonitrile | 453.0 [M$^+$] mp 215° C. |
| 1.20 | S2.1 | 5-pyridin-2-yl-7-trifluoromethyl-pyrazolo[1,5-a]pyrimidine-3-carbonitrile | 289.9 [(M + H)$^+$] mp 208° C. |
| 1.21 | S2.2 | 5-pyridin-3-yl-7-trifluoromethyl-pyrazolo[1,5-a]pyrimidine-3-carbonitrile | 290.2 [(M + H)$^+$] mp 193° C. |
| 1.22 | S2.3 | 5-pyridin-4-yl-7-trifluoromethyl-pyrazolo[1,5-a]pyrimidine-3-carbonitrile | 289.8 [(M + H)$^+$] mp 233° C. | available 4-methyl-acetophenone according to general procedure A, and 3-amino-4-cyano-pyrazole (108 mg, 1.0 mmol) according to general procedure B yielded the title compound as a light yellow solid (151 mg, 50%). MS (ISP) 303.1 [(M+H)$^+$]; mp 121° C.

EXAMPLE 1.3

5-(2-Chloro-phenyl)-7-trifluoromethyl-pyrazolo[1,5-a]pyrimidine-3-carbonitrile

Reaction of 1-(2-chloro-phenyl)-4,4,4-trifluoro-butane-1,3-dione (251 mg, 1.0 mmol), prepared from commercially available 2-chloro-acetophenone according to general procedure A, and 3-amino-4-cyano-pyrazole (108 mg, 1.0 mmol) according to general procedure B yielded the title compound as an off-white solid (73 mg, 23%). MS (ISP) 323.1 [(M+H)$^+$]; mp 169° C.

EXAMPLE 1.4

5-(2,4-Dichloro-phenyl)-7-trifluoromethyl-pyrazolo[1,5-a]pyrimidine-3-carbonitrile Reaction of 1-(2,4-dichloro-phenyl)-4,4,4-trifluoro-butane-1,3-dione (285 mg, 1.0 mmol), prepared from commercially available 2,4-dichloro-acetophenone according to general procedure A, and 3-amino-4-cyano-pyrazole (108 mg, 1.0 mmol) according to general procedure B yielded the title compound as a light brown solid (63 mg, 18%). MS (ISP) 357.1 [(M+H)$^+$]; mp 180° C.

EXAMPLE 1.5

5-(3-Methyl-phenyl)-7-trifluoromethyl-pyrazolo[1,5-a]pyrimidine-3-carbonitrile

Reaction of 1-(3-methyl-phenyl)-4,4,4-trifluoro-butane-1,3-dione (230 mg, 1.0 mmol), prepared from commercially available 3-methyl-acetophenone according to general procedure A, and 3-amino-4-cyano-pyrazole (108 mg, 1.0 mmol) according to general procedure B yielded the title compound as a yellow solid (164 mg, 54%). MS (ISP) 303.2 [(M+H)$^+$]; mp 202° C.

EXAMPLE 1.6

5-(3-Trifluoromethyl-phenyl)-7-trifluoromethyl-pyrazolo[1,5-a]pyrimidine-3-carbonitrile Reaction of 1-(3-trifluoromethyl-phenyl)-4,4,4-trifluoro-butane-1,3-dione (284 mg, 1.0 mmol), prepared from commercially available 3-trifluoromethyl-acetophenone according to general procedure A, and 3-amino-4-cyano-pyrazole (108 mg, 1.0 mmol) according to general procedure B yielded the title compound as a white solid (151 mg, 42%). MS (ISP) 357.0 [(M+H)$^+$]; mp 192° C.

EXAMPLE 1.7

5-(4-Trifluoromethyl-phenyl)-7-trifluoromethyl-pyrazolo[1,5-a]pyrimidine-3-carbonitrile Reaction of 1-(4-trifluoromethyl-phenyl)-4,4,4-trifluoro-butane-1,3-dione (284 mg, 1.0 mmol), prepared from commercially available 4-trifluoromethyl-acetophenone according to general procedure A, and 3-amino-4-cyano-pyrazole (108 mg, 1.0 mmol) according to general procedure B yielded the title compound as an off-white solid (137 mg, 38%). MS (ISP) 357.0 [(M+H)$^+$]; mp 176° C.

EXAMPLE 1.8

5-(3-Fluoro-phenyl)-7-trifluoromethyl-pyrazolo[1,5-a]pyrimidine-3-carbonitrile

Reaction of 1-(3-fluoro-phenyl)-4,4,4-trifluoro-butane-1,3-dione (234 mg, 1.0 mmol), prepared from commercially available 3-fluoro-acetophenone according to general procedure A, and 3-amino-4-cyano-pyrazole (108 mg, 1.0 mmol) according to general procedure B yielded the title compound as a light yellow solid (141 mg, 46%). MS (ISP) 306.9 [(M+H)$^+$]; mp 199° C.

EXAMPLE 1.9

5-(4-Fluoro-phenyl)-7-trifluoromethyl-pyrazolo[1,5-a]pyrimidine-3-carbonitrile

Reaction of 1-(4-fluoro-phenyl)-4,4,4-trifluoro-butane-1,3-dione (234 mg, 1.0 mmol), prepared from commercially available 4-fluoro-acetophenone according to general procedure A, and 3-amino-4-cyano-pyrazole (108 mg, 1.0 mmol) according to general procedure B yielded the title compound as a yellow solid (118 mg, 39%). MS (ISP) 306.9 [(M+H)$^+$]; mp 198° C.

EXAMPLE 1.10

5-(2,4-Difluoro-phenyl)-7-trifluoromethyl-pyrazolo[1,5-a]pyrimidine-3-carbonitrile Reaction of 1-(2,4-difluoro-phenyl)-4,4,4-trifluoro-butane-1,3-dione (252 mg, 1.0 mmol), prepared from commercially available 2,4-difluoro-acetophenone according to general procedure A, and 3-amino-4-cyano-pyrazole (108 mg, 1.0 mmol) according to general procedure B yielded the title compound as a light yellow solid (72 mg, 22%). MS (ISP) 325.0 [(M+H)$^+$]; mp 149° C.

EXAMPLE 1.11

5-(2-Fluoro-phenyl)-7-trifluoromethyl-pyrazolo[1,5-a]pyrimidine-3-carbonitrile

Reaction of 1-(2-fluoro-phenyl)-4,4,4-trifluoro-butane-1,3-dione (234 mg, 1.0 mmol), prepared from commercially available 2-fluoro-acetophenone according to general procedure A, and 3-amino-4-cyano-pyrazole (108 mg, 1.0 mmol) according to general procedure B yielded the title compound as a light yellow solid (83 mg, 27%). MS (ISP) 307.1 [(M+H)$^+$]; mp 165° C.

EXAMPLE 1.12

5-(3,4-Difluoro-phenyl)-7-trifluoromethyl-pyrazolo[1,5-a]pyrimidine-3-carbonitrile Reaction of 1-(3,4-difluoro-phenyl)-4,4,4-trifluoro-butane-1,3-dione (252 mg, 1.0 mmol), prepared from commercially available 3,4-difluoro-acetophenone according to general procedure A, and 3-amino-4-cyano-pyrazole (108 mg, 1.0 mmol) according to general procedure B yielded the title compound as a light yellow solid (137 mg, 42%).

EXAMPLE 1.13

5-(4-Fluoro-3-trifluoromethyl-phenyl)-7-trifluoromethyl-pyrazolo[1,5-a]pyrimidine-3-carbonitrile Reaction of 1-(4-fluoro-3-trifluoromethyl-phenyl)-4,4,4-trifluoro-butane-1,3-dione (302 mg, 1.0 mmol), prepared from commercially available 4-fluoro3-trifluoromethyl-acetophenone according to general procedure A, and 3-amino-4-cyano-pyrazole (108 mg, 1.0 mmol) according to general procedure B yielded the title compound as an off-white solid (144 mg, 38%). MS (ISP) 375.0 [(M+H)$^+$]; mp 204° C.

EXAMPLE 1.14

5-(3-Chloro-4-fluoro-phenyl)-7-trifluoromethyl-pyrazolo[1,5-a]pyrimidine-3-carbonitrile Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and 3-amino-4-cyano-pyrazole (108 mg, 1.0 mmol) according to general procedure B yielded the title compound as an off-white solid (109 mg, 32%). MS (ISP) 341.0 [(M+H)$^+$]; mp 190° C.

EXAMPLE 1.15

5-(4-Chloro-3-methyl-phenyl)-7-trifluoromethyl-pyrazolo[1,5-a]pyrimidine-3-carbonitrile Reaction of 1-(4-chloro-3-methyl-phenyl)-4,4,4-trifluoro-butane-1,3-dione (264 mg, 1.0 mmol), prepared from commercially available 4-chloro-3-methyl-acetophenone according to general procedure A, and 3-amino-4-cyano-pyrazole (108 mg, 1.0 mmol) according to general procedure B yielded the title compound as an off-white solid (128 mg, 38%). MS (ISP) 337.1 [(M+H)$^+$]; mp 216° C.

EXAMPLE 1.16

5-(3,4-Dichloro-phenyl)-7-trifluoromethyl-pyrazolo[1,5-a]pyrimidine-3-carbonitrile Reaction of 1-(3,4-dichloro-phenyl)-4,4,4-trifluoro-butane-1,3-dione (285 mg, 1.0 mmol), prepared from commercially available 3,4-dichloro-acetophenone according to general procedure A, and 3-amino-4-cyano-pyrazole (108 mg, 1.0 mmol) according to general procedure B yielded the title compound as a yellow solid (140 mg, 39%). MS (ISP) 356.9 [(M+H)$^+$]; mp 206° C.

EXAMPLE 1.17

5-(3-Fluoro-4-trifluoromethyl-phenyl)-7-trifluoromethyl-pyrazolo[1,5-a]pyrimidine-3-carbonitrile Reaction of 1-(3-fluoro-4-trifluoromethyl-phenyl)-4,4,4-trifluoro-butane-1,3-dione (302 mg, 1.0 mmol), prepared from commercially available 3-fluoro-4-trifluoromethyl-acetophenone according to general procedure A, and 3-amino-4-cyano-pyrazole (108 mg, 1.0 mmol) according to general procedure B yielded the title compound as an off-white solid (139 mg, 37%). MS (ISP) 375.0 [(M+H)$^+$]; mp 184° C.

EXAMPLE 1.18

2-(3-Methyl-4-trifluoromethyl-phenyl)-4-trifluoromethyl-pyrazolo[1,5-a]pyrimidine-8-carbonitrile Reaction of 1-(3-methyl-4-trifluoromethyl-phenyl)-4,4,4-trifluoro-butane-1,3-dione (224 mg, 0.75 mmol), prepared from 3-methyl-4-trifluoromethyl-acetophenone (synthesis: see part acetophenone derivatives) according to general procedure A, and 3-amino-4-cyano-pyrazole (81 mg, 0.75 mmol) according to general procedure B yielded the title compound as an off-white solid (142 mg, 51%). MS (ISP) 371.1 [(M+H)$^+$]; mp 209° C.

EXAMPLE 1.19

2-(4-Trifluoroethoxy-3-trifluoromethyl-phenyl)-4-trifluoromethyl-pyrazolo[1,5-a]pyrimidine-8-carbonitrile Reaction of 1-(4-trifluoroethoxy-3-trifluoromethyl-phenyl)-4,4,4-trifluoro-butane-1,3-dione (382 mg, 1.0 mmol), prepared from 4-trifluoroethoxy-3-trifluoromethyl-acetophenone (synthesis: see part acetophenone derivatives) according to general procedure A, and 3-amino-4-cyano-pyrazole (108 mg, 1.0 mmol) according to general procedure B yielded the title compound as an off-white solid (226 mg, 50%). MS (ISP) 453.0 [M$^+$]; mp 215° C.

EXAMPLE 1.20

5-Pyridin-2-yl-7-trifluoromethyl-pyrazolo[1,5-a]pyrimidine-3-carbonitrile

Reaction of 1-pyridin-2-yl-4,4,4-trifluoro-butane-1,3-dione (217 mg, 1.0 mmol), prepared from commercially available 2-acetylpyridine according to general procedure A, and 3-amino-4-cyano-pyrazole (108 mg, 1.0 mmol) according to general procedure B yielded the title compound as a light brown solid (135 mg, 47%). MS (ISP) 289.9 [(M+H)$^+$]; mp 208° C.

EXAMPLE 1.21

5-Pyridin-3-yl-7-trifluoromethyl-pyrazolo[1,5-a] pyrimidine-3-carbonitrile

Reaction of 1-pyridin-3-yl-4,4,4-trifluoro-butane-1,3-dione (217 mg, 1.0 mmol), prepared from commercially available 3-acetylpyridine according to general procedure A, and 3-amino-4-cyano-pyrazole (108 mg, 1.0 mmol) according to general procedure B yielded the title compound as an off-white solid (45 mg, 16%). MS (ISP) 290.2 [(M+H)$^+$]; mp 193° C.

EXAMPLE 1.22

5-Pyridin-4-yl-7-trifluoromethyl-pyrazolo[1,5-a] pyrimidine-3-carbonitrile

Reaction of 1-pyridin-4-yl-4,4,4-trifluoro-butane-1,3-dione (217 mg, 1.0 mmol), prepared from commercially available 4-acetylpyridine according to general procedure A, and 3-amino-4-cyano-pyrazole (108 mg, 1.0 mmol) according to general procedure B yielded the title compound as a light yellow solid (110 mg, 38%). MS (ISP) 289.8 [(M+H)$^+$]; mp 233° C.

EXAMPLE 2

Preparation of phenyl-7-trifluoromethyl-pyrazolo[1, 5-a]pyrimidine-3-carbonitriles (General Procedure B)

A stirred mixture of commercially available 3-amino-4-cyano-5-methyl-pyrazole (1 eq.) and a 1-phenyl-4,4,4-trifluoro-butane-1,3-dione (1 eq.), prepared according to general procedure A, in acetic acid was heated under reflux conditions for about 3.5 h. The reaction mixture was evaporated and the product was isolated by column chromatography (heptane/ethyl acetate) and further purified by crystallization. If the product precipitates during the reaction it can be isolated by filtration and further purified by crystallization.

EXAMPLE 2.1

2-Methyl-5-(4-trifluoromethyl-phenyl)-7-trifluoromethyl-pyrazolo[1,5-a]pyrimidine-3-carbonitrile Reaction of 1-(4-trifluoromethyl-phenyl)-4,4,4-trifluoro-butane-1,3-dione (284 mg, 1.0 mmol), prepared from commercially available 4-trifluoromethyl-acetophenone according to general procedure A, and commercially available 3-amino-4-cyano-5-methyl-pyrazole (122 mg, 1.0 mmol) according to general procedure B yielded the title compound as a light yellow solid (234 mg, 63%). MS (ISP) 371.1 [(M+H)$^+$]; mp 184° C.

EXAMPLE 2.2

2-Methyl-5-(3-trifluoromethyl-phenyl)-7-trifluoromethyl-pyrazolo[1,5-a]pyrimidine-3-carbonitrile Reaction of 1-(3-trifluoromethyl-phenyl)-4,4,4-trifluoro-butane-1,3-dione (284 mg, 1.0 mmol), prepared from commercially available 3-trifluoromethyl-acetophenone according to general procedure A, and commercially available 3-amino-4-cyano-5-methyl-pyrazole (122 mg, 1.0 mmol) according to general procedure B yielded the title compound as a light yellow solid (272 mg, 73%). MS (ISP) 371.1 [(M+H)$^+$]; mp 215° C.

EXAMPLE 2.3

5-(4-Chloro-phenyl)-2-methyl-7-trifluoromethyl-pyrazolo[1,5-a]pyrimidine-3-carbonitrile Reaction of 1-(4-chloro-phenyl)-4,4,4-trifluoro-butane-1, 3-dione (251 mg, 1.0 mol), prepared from commercially available 4-chloro-acetophenone according to general procedure A, and commercially available 3-amino-4-cyano-5-methyl-pyrazole (122 mg, 1.0 mmol) according to general procedure B yielded the title compound as a yellow solid (222 mg, 66%). MS (ISP) 337.1 [(M+H)$^+$]; mp 238° C.

EXAMPLE 2.4

5-(3-Chloro-4-fluoro-phenyl)-2-methyl-7-trifluoromethyl-pyrazolo[1,5-a]pyrimidine-3-carbonitrile Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and commercially available 3-amino-4-cyano-5-methyl-pyrazole (122 mg, 1.0 mmol) according to general procedure B yielded the title compound as a light yellow solid (243 mg, 69%). MS (ISP) 355.0 [(M+H)$^+$]; mp 196° C.

| Ex. | dione | compound name | MS (ISP)/mp |
|---|---|---|---|
| 2.1 | S1.7 | 2-methyl-5-(4-trifluoromethyl-phenyl)-7-trifluoromethyl-pyrazolo[1,5-a]pyrimidine-3-carbonitrile | 371.1 [(M + H)$^+$] mp 184° C. |
| 2.2 | S1.6 | 2-methyl-5-(3-trifluoromethyl-phenyl)-7-trifluoromethyl-pyrazolo[1,5-a]pyrimidine-3-carbonitrile | 371.1 [(M + H)$^+$] mp 215° C. |
| 2.3 | S1.17 | 5-(4-chloro-phenyl)-2-methyl-7-trifluoromethyl-pyrazolo[1,5-a]pyrimidine-3-carbonitrile | 337.1 [(M + H)$^+$] mp 238° C. |
| 2.4 | S1.14 | 5-(3-chloro-4-fluoro-phenyl)-2-methyl-7-trifluoromethyl-pyrazolo[1,5-a]pyrimidine-3-carbonitrile | 355.0 [(M + H)$^+$] mp 196° C. |

EXAMPLE 3

Preparation of phenyl-7-trifluoromethyl-pyrazolo[1,5-a]pyrimidine-3-carbonitriles (General Procedure B)

A stirred mixture of commercially available 3-amino-4-cyano-5-cyanomethyl-pyrazole (1 eq.) and a 1-phenyl-4,4,4-trifluoro-butane-1,3-dione (1 eq.), prepared according to general procedure A, in acetic acid was heated under reflux conditions for 3.5 h. The reaction mixture was evaporated and the product was isolated by column chromatography (heptane/ethyl acetate) and further purified by crystallization. If the product precipitates during the reaction it can be isolated by filtration and further purified by crystallization.

| Ex. | dione | compound name | MS (ISP)/mp |
|---|---|---|---|
| 3.1 | S1.14 | 5-(3-chloro-4-fluoro-phenyl)-2-cyanomethyl-7-trifluoromethyl-pyrazolo[1,5-a]pyrimidine-3-carbonitrile | 380.1 [(M + H)$^+$] mp 185° C. |
| 3.2 | S1.15 | 5-(4-chloro-3-methyl-phenyl)-2-cyanomethyl-7-trifluoromethyl-pyrazolo[1,5-a]pyrimidine-3-carbonitrile | 376.1 [(M + H)$^+$] mp 238° C. |

EXAMPLE 3.1

5-(3-Chloro-4-fluoro-phenyl)-2-cyanomethyl-7-trifluoromethyl-pyrazolo[1,5-a]pyrimidine-3-carbonitrile Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and commercially available 3-amino-4-cyano-5-cyanomethyl-pyrazole (147 mg, 1.0 mmol) according to general procedure B yielded the title compound as a light yellow solid (223 mg, 59%). MS (ISP) 380.1 [(M+H)$^+$]; mp 185° C.

EXAMPLE 3.2

5-(4-Chloro-3-methyl-phenyl)-2-cyanomethyl-7-trifluoromethyl-pyrazolo[1,5-a]pyrimidine-3-carbonitrile Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and commercially available 3-amino-4-cyano-5-cyanomethyl-pyrazole (74 mg, 0.5 mmol) according to general procedure B yielded the title compound as a light yellow solid (99 mg, 53%). MS (ISP) 376.1 [(M+H)$^+$]; mp 238° C.

EXAMPLE 4

Preparation of 5-phenyl-3-pyridinyl-7-trifluoromethyl-pyrazolo[1,5-a]pyrimidines (General Procedure B)

A stirred mixture of a 3-amino-4-pyridinyl-pyrazole (1 eq.) and a 1-phenyl-4,4,4-trifluoro-butane-1,3-dione (1 eq.), prepared according to general procedure A, in acetic acid was heated under reflux conditions for 3.5 h. The reaction mixture was evaporated and the product was isolated by column chromatography (heptane/ethyl acetate) and further purified by crystallization. If the product precipitates during the reaction it can be isolated by filtration and further purified by crystallization.

| Ex. | dione | pyrazole | compound name | MS (ISP)/mp |
|---|---|---|---|---|
| 4.1 | S1.17 | S3.1 | 5-(4-chloro-phenyl)-3-pyridin-3-yl-7-trifluoromethyl-pyrazolo[1,5-a]pyrimidine | 375.3 [(M + H)$^+$] mp 188° C. |
| 4.2 | S1.17 | S3.2 | 5-(4-chloro-phenyl)-3-pyridin-4-yl-7-trifluoromethyl-pyrazolo[1,5-a]pyrimidine | 375.3 [(M + H)$^+$] mp 274° C. |
| 4.3 | S1.15 | S3.1 | 5-(4-chloro-3-methyl-phenyl)-3-pyridin-3-yl-7-trifluoromethyl-pyrazolo[1,5-a]pyrimidine | 375.3 [(M + H)$^+$] mp 193° C. |
| 4.4 | S1.15 | S3.2 | 5-(4-chloro-3-methyl-phenyl)-3-pyridin-4-yl-7-trifluoromethyl-pyrazolo[1,5-a]pyrimidine | 389.2 [(M + H)$^+$] mp 247° C. |
| 4.5 | S1.15 | S3.3 | 5-(4-chloro-3-methyl-phenyl)-3-pyridin-2-yl-7-trifluoromethyl-pyrazolo[1,5-a]pyrimidine | 389.2 [(M + H)$^+$] mp 183° C. |
| 4.6 | S1.14 | S3.1 | 5-(3-chloro-4-fluoro-phenyl)-3-pyridin-3-yl-7-trifluoromethyl-pyrazolo[1,5-a]pyrimidine | 393.1 [(M + H)$^+$] mp 190° C. |
| 4.7 | S1.14 | S3.2 | 5-(3-chloro-4-fluoro-phenyl)-3-pyridin-4-yl-7-trifluoromethyl-pyrazolo[1,5-a]pyrimidine | 393.1 [(M + H)$^+$] mp 265° C. |
| 4.8 | S1.14 | S3.3 | 5-(3-chloro-4-fluoro-phenyl)-3-pyridin-2-yl-7-trifluoromethyl-pyrazolo[1,5-a]pyrimidine | 393.1 [(M + H)$^+$] mp 197° C. |
| 4.9 | S1.16 | S3.1 | 5-(3,4-dichloro-phenyl)-3-pyridin-3-yl-7-trifluoromethyl-pyrazolo[1,5-a]pyrimidine | 409.1 [(M + H)$^+$] mp 224° C. |
| 4.10 | S1.16 | S3.2 | 5-(3,4-dichloro-phenyl)-3-pyridin-4-yl-7-trifluoromethyl-pyrazolo[1,5-a]pyrimidine | 409.2 [(M + H)$^+$] mp 260° C. |
| 4.11 | S1.16 | S3.3 | 5-(3,4-dichloro-phenyl)-3-pyridin-2-yl-7-trifluoromethyl-pyrazolo[1,5-a]pyrimidine | 409.2 [(M + H)$^+$] mp 188° C. |
| 4.12 | S1.7 | S3.3 | 5-(4-trifluoromethyl-phenyl)-3-pyridin-2-yl-7-trifluoromethyl-pyrazolo[1,5-a]pyrimidine | 409.2 [(M + H)$^+$] mp 202° C. |

-continued

| Ex. | dione | pyrazole | compound name | MS (ISP)/mp |
|---|---|---|---|---|
| 4.13 | S1.6 | S3.1 | 5-(3-trifluoromethyl-phenyl)-3-pyridin-3-yl-7-trifluoromethyl-pyrazolo[1,5-a]pyrimidine | 409.2 [(M + H)+] mp 171° C. |
| 4.14 | S1.7 | S3.1 | 5-(4-trifluoromethyl-phenyl)-3-pyridin-3-yl-7-trifluoromethyl-pyrazolo[1,5-a]pyrimidine | 409.2 [(M + H)+] mp 163° C. |
| 4.15 | S1.7 | S3.2 | 5-(4-trifluoromethyl-phenyl)-3-pyridin-4-yl-7-trifluoromethyl-pyrazolo[1,5-a]pyrimidine | 409.2 [(M + H)+] mp 261° C. |
| 4.16 | S1.6 | S3.2 | 5-(3-trifluoromethyl-phenyl)-3-pyridin-4-yl-7-trifluoromethyl-pyrazolo[1,5-a]pyrimidine | 409.2 [(M + H)+] mp 241° C. |
| 4.17 | S1.18 | S3.2 | 5-(3-fluoro-4-trifluoromethyl-phenyl)-3-pyridin-4-yl-7-trifluoromethyl-pyrazolo[1,5-a]pyrimidine | 427.0 [(M + H)+] mp 262° C. |
| 4.18 | S1.18 | S3.1 | 5-(3-fluoro-4-trifluoromethyl-phenyl)-3-pyridin-3-yl-7-trifluoromethyl-pyrazolo[1,5-a]pyrimidine | 427.0 [(M + H)+] mp 162° C. |
| 4.19 | S1.17 | S3.4 | 5-(4-chloro-phenyl)-3-(2,6-dimethyl-pyridin-4-yl)-7-trifluoromethyl-pyrazolo[1,5-a]pyrimidine | 403.2 [(M + H)+] mp 256° C. |
| 4.20 | S1.15 | S3.4 | 5-(4-chloro-3-methyl-phenyl)-3-(2,6-dimethyl-pyridin-4-yl)-7-trifluoromethyl-pyrazolo[1,5-a]pyrimidine | 417.2 [(M + H)+] mp 254° C. |
| 4.21 | S1.14 | S3.4 | 5-(3-chloro-4-fluoro-phenyl)-3-(2,6-dimethyl-pyridin-4-yl)-7-trifluoromethyl-pyrazolo[1,5-a]pyrimidine | 421.1 [(M + H)+] mp 271° C. |
| 4.22 | S1.16 | S3.4 | 5-(3,4-dichloro-phenyl)-3-(2,6-dimethyl-pyridin-4-yl)-7-trifluoromethyl-pyrazolo[1,5-a]pyrimidine | 437.1 [(M + H)+] mp 281° C. |
| 4.23 | S1.7 | S3.4 | 5-(4-trifluoromethyl-phenyl)-3-(2,6-dimethyl-pyridin-4-yl)-7-trifluoromethyl-pyrazolo[1,5-a]pyrimidine | 437.2 [(M + H)+] mp 257° C. |
| 4.24 | S1.6 | S3.4 | 5-(3-trifluoromethyl-phenyl)-3-(2,6-dimethyl-pyridin-4-yl)-7-trifluoromethyl-pyrazolo[1,5-a]pyrimidine | 437.2 [(M + H)+] mp 236° C. |
| 4.25 | S1.18 | S3.4 | 5-(3-fluoro-4-trifluoromethyl-phenyl)-3-(2,6-dimethyl-pyridin-4-yl)-7-trifluoromethyl-pyrazolo[1,5-a]pyrimidine | 455.0 [(M + H)+] mp 245° C. |
| 4.26 | S1.21 | S3.1 | 5-(4-methyl-3-trifluoromethyl-phenyl)-3-pyridin-3-yl-7-trifluoromethyl-pyrazolo[1,5-a]pyrimidine | 423.2 [(M + H)+] mp 182° C. |
| 4.27 | S1.21 | S3.2 | 5-(4-methyl-3-trifluoromethyl-phenyl)-3-pyridin-4-yl-7-trifluoromethyl-pyrazolo[1,5-a]pyrimidine | 423.1 [(M + H)+] mp 218° C. |
| 4.28 | S1.21 | S3.4 | 5-(4-methyl-3-trifluoromethyl-phenyl)-3-(2,6-dimethyl-pyridin-4-yl)-7-trifluoromethyl-pyrazolo[1,5-a]pyrimidine | 451.2 [(M + H)+] mp 258° C. |
| 4.29 | S1.17 | S3.5 | 5-(4-chloro-phenyl)-3-(2-methyl-pyridin-4-yl)-7-trifluoromethyl-pyrazolo[1,5-a]pyrimidine | 389.1 [(M + H)+] mp 220° C. |
| 4.30 | S1.15 | S3.5 | 5-(4-chloro-3-methyl-phenyl)-3-(2-methyl-pyridin-4-yl)-7-trifluoromethyl-pyrazolo[1,5-a]pyrimidine | 403.5 [(M + H)+] mp 240° C. |
| 4.31 | S1.14 | S3.5 | 5-(3-chloro-4-fluoro-phenyl)-3-(2-methyl-pyridin-4-yl)-7-trifluoromethyl-pyrazolo[1,5-a]pyrimidine | 407.3 [(M + H)+] mp 292° C. |
| 4.32 | S1.16 | S3.5 | 5-(3,4-dichloro-phenyl)-3-(2-methyl-pyridin-4-yl)-7-trifluoromethyl-pyrazolo[1,5-a]pyrimidine | 423.0 [(M + H)+] mp 275° C. |
| 4.33 | S1.7 | S3.5 | 5-(4-trifluoromethyl-phenyl)-3-(2-methyl-pyridin-4-yl)-7-trifluoromethyl-pyrazolo[1,5-a]pyrimidine | 423.0 [(M + H)+] mp 243° C. |
| 4.34 | S1.6 | S3.5 | 5-(3-trifluoromethyl-phenyl)-3-(2-methyl-pyridin-4-yl)-7-trifluoromethyl-pyrazolo[1,5-a]pyrimidine | 423.3 [(M + H)+] mp 232° C. |
| 4.35 | S1.18 | S3.5 | 5-(3-fluoro-4-trifluoromethyl-phenyl)-3-(2-methyl-pyridin-4-yl)-7-trifluoromethyl-pyrazolo[1,5-a]pyrimidine | 441.5 [(M + H)+] mp 250° C. |
| 4.36 | S1.19 | S3.1 | 5-(3-methyl-4-trifluoromethyl-phenyl)-3-pyridin-3-yl-7-trifluoromethyl-pyrazolo[1,5-a]pyrimidine | 423.3 [(M + H)+] mp 177° C. |

-continued

| Ex. | dione | pyrazole | compound name | MS (ISP)/mp |
|---|---|---|---|---|
| 4.37 | S1.19 | S3.2 | 5-(3-methyl-4-trifluoromethyl-phenyl)-3-pyridin-4-yl-7-trifluoromethyl-pyrazolo[1,5-a]pyrimidine | 423.3 [(M + H)+] mp 227° C. |
| 4.38 | S1.19 | S3.4 | 5-(3-methyl-4-trifluoromethyl-phenyl)-3-(2,6-dimethyl-pyridin-4-yl)-7-trifluoromethyl-pyrazolo[1,5-a]pyrimidine | 451.5 [(M + H)+] mp 253° C. |
| 4.39 | S1.19 | S3.5 | 5-(3-methyl-4-trifluoromethyl-phenyl)-3-(2-methyl-pyridin-4-yl)-7-trifluoromethyl-pyrazolo[1,5-a]pyrimidine | 437.5 [(M + H)+] mp 237° C. |
| 4.40 | S1.22 | S3.1 | 5-(4-ethoxy-3-trifluoromethyl-phenyl)-3-pyridin-3-yl-7-trifluoromethyl-pyrazolo[1,5-a]pyrimidine | 453.5 [(M + H)+] mp 178° C. |
| 4.41 | S1.22 | S3.2 | 5-(4-ethoxy-3-trifluoromethyl-phenyl)-3-pyridin-4-yl-7-trifluoromethyl-pyrazolo[1,5-a]pyrimidine | 453.5 [(M + H)+] mp 233° |
| 4.42 | S1.20 | S3.1 | 5-(4-trifluoroethoxy-3-trifluoromethyl-phenyl)-3-pyridin-3-yl-7-trifluoromethyl-pyrazolo[1,5-a]pyrimidine | 507.5 [(M + H)+] mp 181° C. |
| 4.43 | S1.20 | S3.2 | 5-(4-trifluorothoxy-3-trifluoromethyl-phenyl)-3-pyridin-4-yl-7-trifluoromethyl-pyrazolo[1,5-a]pyrimidine | 507.5 [(M + H)+] mp 247° C. |
| 4.44 | S1.22 | S3.5 | 5-(4-ethoxy-3-trifluoromethyl-phenyl)-3-(2-methyl-pyridin-4-yl)-7-trifluoromethyl-pyrazolo[1,5-a]pyrimidine | 467.2 [(M + H)+] mp 250° C. |
| 4.45 | S1.20 | S3.4 | 5-(4-trifluoroethoxy-3-trifluoromethyl-phenyl)-3-(2,6-dimethyl-pyridin-4-yl)-7-trifluoromethyl-pyrazolo[1,5-a]pyrimidine | 535.5 [(M + H)+] mp 229° C. |
| 4.46 | S1.20 | S3.5 | 5-(4-trifluoroethoxy-3-trifluoromethyl-phenyl)-3-(2-methyl-pyridin-4-yl)-7-trifluoromethyl-pyrazolo[1,5-a]pyrimidine | 521.5 [(M + H)+] mp 210° C. |
| 4.47 | S1.26 | S3.2 | 5-(3-Ethoxy-4-trifluoromethyl-phenyl)-3-pyridin-4-yl-7-trifluoromethyl-pyrazolo[1,5-a]pyrimidine | MS (ISP) 453.1 [(M + H)+] mp 251° C. |
| 4.48 | S1.26 | S3.4 | 3-(2,6-Dimethyl-pyridin-4-yl)-5-(3-ethoxy-4-trifluoromethyl-phenyl)-7-trifluoromethyl-pyrazolo[1,5-a]pyrimidine | MS (ISP) 481.4 [(M + H)+] mp 257° C. |
| 4.49 | S1.26 | S3.5 | 5-(3-Ethoxy-4-trifluoromethyl-phenyl)-3-(2-methyl-pyridin-4-yl)-7-trifluoromethyl-pyrazolo[1,5-a]pyrimidine | MS (ISP) 467.4 [(M + H)+] mp 226° C. |
| 4.50 | S1.27 | S3.2 | 3-Pyridin-4-yl-5-[3-(2,2,2-trifluoro-ethoxy)-4-trifluoromethyl-phenyl]-7-trifluoromethyl-pyrazolo[1,5-a]pyrimidine | MS (ISP) 507.4 [(M + H)+] mp 251° C. |
| 4.51 | S1.27 | S3.4 | 3-(2,6-Dimethyl-pyridin-4-yl)-5-[3-(2,2,2-trifluoro-ethoxy)-4-trifluoromethyl-phenyl]-7-trifluoromethyl-pyrazolo[1,5-a]pyrimidine | MS (ISP) 535.4 [(M + H)+] mp 245° C. |
| 4.52 | S1.27 | S3.5 | 3-(2-Methyl-pyridin-4-yl)-5-[3-(2,2,2-trifluoro-ethoxy)-4-trifluoromethyl-phenyl]-7-trifluoromethyl-pyrazolo[1,5-a]pyrimidine | MS (ISP) 521.4 [(M + H)+] mp 201° C. |
| 4.53 | S1.28 | S3.2 | 5-(3,4-Bis-trifluoromethyl-phenyl)-3-pyridin-4-yl-7-trifluoromethyl-pyrazolo[1,5-a]pyrimidine. Yellow solid. | MS (ISP) 477.2 [(M + H)+] mp 209° C. |
| 4.54 | S1.28 | S3.5 | 5-(3,4-Bis-trifluoromethyl-phenyl)-3-(2-methyl-pyridin-4-yl)-7-trifluoromethyl-pyrazolo[1,5-a]pyrimidine | MS (ISP) 491.3 [(M + H)+] mp 223° C. |
| 4.55 | S1.29 | S3.2 | 5-(4-Bromo-phenyl)-3-pyridin-4-yl-7-trifluoromethyl-pyrazolo[1,5-a]pyrimidine | MS (ISP) 421.2 [(M + H)+] mp 289° C. |
| 4.56 | S1.29 | S3.5 | 5-(4-Bromo-phenyl)-3-(2-methyl-pyridin-4-yl)-7-trifluoromethyl-pyrazolo[1,5-a]pyrimidine | MS (ISP) 433.3 [(M + H)+] mp 226° C. |
| 4.57 | S1.29 | S3.4 | 5-(4-Bromo-phenyl)-3-(2,6-dimethyl-pyridin-4-yl)-7-trifluoromethyl-pyrazolo[1,5-a]pyrimidine | MS (ISP) 447.2 [(M + H)+] mp 258° C. |
| 4.58 | S1.30 | S3.2 | 5-(4-Methoxy-phenyl)-3-pyridin-4-yl-7-trifluoromethyl-pyrazolo[1,5-a]pyrimidine | MS (ISP) 371.2 [(M + H)+] mp 244° C. |

EXAMPLE 4.1

5-(4-Chloro-phenyl)-3-pyridin-3-yl-7-trifluoromethyl-pyrazolo[1,5-a]pyrimidine

Reaction of 1-(4-chloro-phenyl)-4,4,4-trifluoro-butane-1,3-dione (251 mg, 1.0 mmol), prepared from commercially available 4-chloro-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (160 mg, 1.0 mmol) according to general procedure B yielded the title compound as a yellow solid (306 mg, 82%). MS (ISP) 375.3 [(M+H)$^+$]; mp 188° C.

EXAMPLE 4.2

5-(4-Chloro-phenyl)-3-pyridin-4-yl-7-trifluoromethyl-pyrazolo[1,5-a]pyrimidine

Reaction of 1-(4-chloro-phenyl)-4,4,4-trifluoro-butane-1,3-dione (125 mg, 0.5 mmol), prepared from commercially available 4-chloro-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 9.5 mmol) according to general procedure B yielded the title compound as a yellow solid (135 mg, 72%). MS (ISP) 375.3 [(M+H)$^+$]; mp 274° C.

EXAMPLE 4.3

5-(4-Chloro-3-methyl-phenyl)-3-pyridin-3-yl-7-trifluoromethyl-pyrazolo[1,5-a]pyrimidine Reaction of 1-(4-chloro-3-methyl-phenyl)-4,4,4-trifluoro-butane-1,3-dione (265 mg, 1.0 mmol), prepared from commercially available 4-chloro-3-methyl-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (160 mg, 1.0 mmol) according to general procedure B yielded the title compound as a yellow solid (274 mg, 70%). MS (ISP) 375.3 [(M+H)$^+$]; mp 193° C.

EXAMPLE 4.4

5-(4-Chloro-3-methyl-phenyl)-3-pyridin-4-yl-7-trifluoromethyl-pyrazolo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (145 mg, 75%). MS (ISP) 389.2 [(M+H)$^+$]; mp 247° C.

EXAMPLE 4.5

5-(4-Chloro-3-methyl-phenyl)-3-pyridin-2-yl-7-trifluoromethyl-pyrazolo[1,5-a]pyrimidine Reaction of 1-(4-chloro-3-methyl-phenyl)-4,4,4-trifluoro-butane-1,3-dione (265 mg, 1.0 mmol), prepared from commercially available 4-chloro-3-methyl-acetophenone according to general procedure A, and 3-amino-4-(2-pyridinyl)-pyrazole [CAS No. 493038-87-2; prepared from 2-cyanomethyl-pyridine as described in Bioorg. Med. Chem. Lett. 12 (2002) 3537-3541] (160 mg, 1.0 mmol) according to general procedure B yielded the title compound as a yellow solid (270 mg, 69%). MS (ISP) 389.2 [(M+H)$^+$]; mp 183° C.

EXAMPLE 4.6

5-(3-Chloro-4-fluoro-phenyl)-3-pyridin-3-yl-7-trifluoromethyl-pyrazolo[1,5-a]pyrimidine Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (160 mg, 1.0 mmol) according to general procedure B yielded the title compound as a yellow solid (270 mg, 69%). MS (ISP) 393.1 [(M+H)$^+$]; mp 190° C.

EXAMPLE 4.7

5-(3-Chloro-4-fluoro-phenyl)-3-pyridin-4-yl-7-trifluoromethyl-pyrazolo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (82 mg, 42%). MS (ISP) 393.1 [(M+H)$^+$]; mp 265° C.

EXAMPLE 4.8

5-(3-Chloro-4-fluoro-phenyl)-3-pyridin-2-yl-7-trifluoromethyl-pyrazolo[1,5-a]pyrimidine Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and 3-amino-4-(2-pyridinyl)-pyrazole [CAS No. 493038-87-2; prepared from 2-cyanomethyl-pyridine as described in Bioorg. Med. Chem. Lett. 12 (2002) 3537-3541] (160 mg, 1.0 mmol) according to general procedure B yielded the title compound as a yellow solid (279 mg, 71%). MS (ISP) 393.1 [(M+H)$^+$]; mp 197° C.

EXAMPLE 4.9

5-(3,4-Dichloro-phenyl)-3-pyridin-3-yl-7-trifluoromethyl-pyrazolo[1,5-a]pyrimidine Reaction of 1-(3,4-dichloro-phenyl)-4,4,4-trifluoro-butane-1,3-dione (285 mg, 1.0 mmol), prepared from commercially available 3,4-dichloro-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (160 mg, 1.0 mmol) according to general procedure B yielded the title compound as a light yellow solid (274 mg, 67%). MS (ISP) 409.1 [(M+H)$^+$]; mp 224° C.

EXAMPLE 4.10

5-(3,4-Dichloro-phenyl)-3-pyridin-4-yl-7-trifluoromethyl-pyrazolo[1,5-a]pyrimidine Reaction of 1-(3,4-dichloro-phenyl)-4,4,4-trifluoro-butane-1,3-dione (285 mg, 1.0 mmol), prepared from commercially available 3,4-dichloro-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (160 mg, 1.0 mmol) according to general procedure B yielded the title compound as a yellow solid (94 mg, 46%). MS (ISP) 409.2 [(M+H)$^+$]; mp 260° C.

EXAMPLE 4.11

5-(3,4-Dichloro-phenyl)-3-pyridin-2-yl-7-trifluoromethyl-pyrazolo[1,5-a]pyrimidine Reaction of 1-(3,4-dichloro-phenyl)-4,4,4-trifluoro-butane-1,3-dione (285 mg, 1.0 mmol), prepared from commercially available 3,4-dichloro-acetophenone according to general procedure A, and 3-amino-4-(2-pyridinyl)-pyrazole [CAS No. 493038-87-2; prepared from 2-cyanomethyl-pyridine as described in Bioorg. Med. Chem. Lett. 12 (2002) 3537-3541] (160 mg, 1.0 mmol) according to general procedure B yielded the title compound as a yellow solid (223 mg, 55%). MS (ISP) 409.2 [(M+H)$^+$]; mp 188° C.

EXAMPLE 4.12

5-(4-Trifluoromethyl-phenyl)-3-pyridin-2-yl-7-trifluoromethyl-pyrazolo[1,5-a]pyrimidine Reaction of 1-(4-trifluoromethyl-phenyl)-4,4,4-trifluoro-butane-1,3-dione (142 mg, 0.5 mmol), prepared from commercially available 3,4-dichloro-acetophenone according to general procedure A, and 3-amino-4-(2-pyridinyl)-pyrazole [CAS No. 493038-87-2; prepared from 2-cyanomethyl-pyridine as described in Bioorg. Med. Chem. Lett. 12 (2002) 3537-3541] (80 mg, 0.5 mmol) according to general procedure B yielded the title compound as a yellow solid (145 mg, 71%). MS (ISP) 409.2 [(M+H)$^+$]; mp 202° C.

EXAMPLE 4.13

5-(3-Trifluoromethyl-phenyl)-3-pyridin-3-yl-7-trifluoromethyl-pyrazolo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (80 mg, 0.5 mmol) according to general procedure B yielded the title compound as a yellow solid (126 mg, 62%). MS (ISP) 409.2 [(M+H)$^+$]; mp 171° C.

EXAMPLE 4.14

5-(4-Trifluoromethyl-phenyl)-3-pyridin-3-yl-7-trifluoromethyl-pyrazolo[1,5-a]pyrimidine Reaction of 1-(4-trifluoromethyl-phenyl)-4,4,4-trifluoro-butane-1,3-dione (142 mg, 0.5 mmol), prepared from commercially available 4-trifluoromethyl-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (80 mg, 0.5 mmol) according to general procedure B yielded the title compound as a yellow solid (142 mg, 70%). MS (ISP) 409.2 [(M+H)$^+$]; mp 163° C.

EXAMPLE 4.15

5-(4-Trifluoromethyl-phenyl)-3-pyridin-4-yl-7-trifluoromethyl-pyrazolo[1,5-a]pyrimidine Reaction of 1-(4-trifluoromethyl-phenyl)-4,4,4-trifluoro-butane-1,3-dione (142 mg, 0.5 mmol), prepared from commercially available 4-trifluoromethyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (93 mg, 46%). MS (ISP) 409.2 [(M+H)$^+$]; mp 261° C.

EXAMPLE 4.16

5-(3-Trifluoromethyl-phenyl)-3-pyridin-4-yl-7-trifluoromethyl-pyrazolo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (95 mg, 47%). MS (ISP) 409.2 [(M+H)$^+$]; mp 241° C.

EXAMPLE 4.17

5-(3-Fluoro-4-trifluoromethyl-phenyl)-3-pyridin-4-yl-7-trifluoromethyl-pyrazolo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (92 mg, 43%). MS (ISP) 427.0 [(M+H)$^+$]; mp 262° C.

EXAMPLE 4.18

5-(3-Fluoro-4-trifluoromethyl-phenyl)-3-pyridin-3-yl-7-trifluoromethyl-pyrazolo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (80 mg, 0.5 mmol) according to general procedure B yielded the title compound as a yellow solid (135 mg, 63%). MS (ISP) 427.0 [(M+H)$^+$]; mp 162° C.

EXAMPLE 4.19

5-(4-Chloro-phenyl)-3-(2,6-dimethyl-pyridin-4-yl)-7-trifluoromethyl-pyrazolo[1,5-a]pyrimidine Reaction of 1-(4-chloro-phenyl)-4,4,4-trifluoro-butane-1,3-dione (125 mg, 0.5 mmol), prepared from commercially available 4-chloro-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (95 mg, 47%). MS (ISP) 403.2 [(M+H)$^+$]; mp 256° C.

EXAMPLE 4.20

5-(4-Chloro-3-methyl-phenyl)-3-(2,6-dimethyl-pyridin-4-yl)-7-trifluoromethyl-pyrazolo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 3-amino-4-(2,6-dimethyl-4-pyridinyl)-pyrazole [prepared from 4-cyanomethyl-2,6-dimethyl-pyridine, see part synthesis of amino-pyrazole derivatives] (94 mg, 0.5 mmol) according to general procedure B yielded the title compound as a yellow solid (95 mg, 46%). MS (ISP) 417.2 [(M+H)$^+$]; mp 254° C.

EXAMPLE 4.21

5-(3-Chloro-4-fluoro-phenyl)-3-(2,6-dimethyl-pyridin-4-yl)-7-trifluoromethyl-pyrazolo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (97 mg, 46%). MS (ISP) 421.1 [(M+H)$^+$]; mp 271° C.

EXAMPLE 4.22

5-(3,4-Dichloro-phenyl)-3-(2,6-dimethyl-pyridin-4-yl)-7-trifluoromethyl-pyrazolo[1,5-a]pyrimidine Reaction of 1-(3,4-dichloro-phenyl)-4,4,4-trifluoro-butane-1,3-dione (143 mg, 0.5 mmol), prepared from commercially available 3,4-dichloro-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (106 mg, 48%). MS (ISP) 437.1 [(M+H)$^+$]; mp 281° C.

EXAMPLE 4.23

5-(4-Trifluoromethyl-phenyl)-3-(2,6-dimethyl-pyridin-4-yl)-7-trifluoromethyl-pyrazolo[1,5-a]pyrimidine Reaction of 1-(4-trifluoromethyl-phenyl)-4,4,4-trifluoro-butane-1,3-dione (142 mg, 0.5 mmol), prepared from commercially available 4-trifluoromethyl-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (102 mg, 47%). MS (ISP) 437.2 [(M+H)$^+$]; mp 257° C.

EXAMPLE 4.24

5-(3-Trifluoromethyl-phenyl)-3-(2,6-dimethyl-pyridin-4-yl)-7-trifluoromethyl-pyrazolo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (99 mg, 45%). MS (ISP) 437.2 [(M+H)$^+$]; mp 236° C.

EXAMPLE 4.25

5-(3-Fluoro-4-trifluoromethyl-phenyl)-3-(2,6-dimethyl-pyridin-4-yl)-7-trifluoromethyl-pyrazolo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (46 mg, 20%). MS (ISP) 455.0 [(M+H)$^+$]; mp 245° C.

EXAMPLE 4.26

5-(4-Methyl-3-trifluoromethyl-phenyl)-3-pyridin-3-yl-7-trifluoromethyl-pyrazolo[1,5-a]pyrimidine Reaction of 1-(4-methyl-3-trifluoromethyl-phenyl)-4,4,4-trifluoro-butane-1,3-dione (149 mg, 0.5 mmol), prepared from 4-methyl-3-trifluoromethyl-acetophenone according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (80 mg, 0.5 mmol) according to general procedure B yielded the title compound as a yellow solid (160 mg, 76%). MS (ISP) 423.2 [(M+H)$^+$]; mp 182° C.

EXAMPLE 4.27

5-(4-Methyl-3-trifluoromethyl-phenyl)-3-pyridin-4-yl-7-trifluoromethyl-pyrazolo[1,5-a]pyrimidine Reaction of 1-(4-methyl-3-trifluoromethyl-phenyl)-4,4,4-trifluoro-butane-1,3-dione (149 mg, 0.5 mmol), prepared from 4-methyl-3-trifluoromethyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (122 mg, 58%). MS (ISP) 423.1 [(M+H)$^+$]; mp 218° C.

EXAMPLE 4.28

5-(4-Methyl-3-trifluoromethyl-phenyl)-3-(2,6-dimethyl-pyridin-4-yl)-7-trifluoromethyl-pyrazolo[1,5-a]pyrimidine Reaction of 1-(4-methyl-3-trifluoromethyl-phenyl)-4,4,4-trifluoro-butane-1,3-dione (149 mg, 0.5 mmol), prepared from 4-methyl-3-trifluoromethyl-acetophenone (synthesis: see part acetophenone derivatives) according to general procedure A, and 3-amino-4-(2,6-dimethyl-4-pyridinyl)-pyrazole [prepared from 4-cyanomethyl-2,6-dimethyl-pyridine, see part synthesis of amino-pyrazole derivatives] (94 mg, 0.5 mmol) according to general procedure B yielded the title compound as a yellow solid (114 mg, 51%). MS (ISP) 451.2 [(M+H)$^+$]; mp 258° C.

EXAMPLE 4.29

5-(4-Chloro-phenyl)-3-(2-methyl-pyridin-4-yl)-7-trifluoromethyl-pyrazolo[1,5-a]pyrimidine Reaction of 1-(4-chloro-phenyl)-4,4,4-trifluoro-butane-1,3-dione (125 mg, 0.5 mmol), prepared from commercially available 4-chloro-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (84 mg, 43%). MS (ISP) 389.1 [(M+H)$^+$]; mp 220° C.

EXAMPLE 4.30

5-(4-Chloro-3-methyl-phenyl)-3-(2-methyl-pyridin-4-yl)-7-trifluoromethyl -pyrazolo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (97 mg, 48%). MS (ISP) 403.5 [(M+H)$^+$]; mp 240° C.

EXAMPLE 4.31

5-(3-Chloro-4-fluoro-phenyl)-3-(2-methyl-pyridin-4-yl)-7-trifluoromethyl-pyrazolo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (86 mg, 42%). MS (ISP) 407.3 [(M+H)$^+$]; mp 292° C.

EXAMPLE 4.32

5-(3,4-Dichloro-phenyl)-3-(2-methyl-pyridin-4-yl)-7-trifluoromethyl-pyrazolo[1,5-a]pyrimidine Reaction of 1-(3,4-dichloro-phenyl)-4,4,4-trifluoro-butane-1,3-dione (143 mg, 0.5 mmol), prepared from commercially available 3,4-dichloro-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (100 mg, 47%). MS (ISP) 423.0 [(M+H)$^+$]; mp 275° C.

EXAMPLE 4.33

5-(4-Trifluoromethyl-phenyl)-3-(2-methyl-pyridin-4-yl)-7-trifluoromethyl -pyrazolo[1,5-a]pyrimidine Reaction of 1-(4-trifluoromethyl-phenyl)-4,4,4-trifluoro-butane-1,3-dione (142 mg, 0.5, mmol), prepared from commercially available 4-trifluoromethyl-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (111 mg, 53%). MS (ISP) 423.0 [(M+H)$^+$]; mp 243° C.

EXAMPLE 4.34

5-(3-Trifluoromethyl-phenyl)-3-(2-methyl-pyridin-4-yl)-7-trifluoromethyl-pyrazolo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (108 mg, 51%). MS (ISP) 423.3 [(M+H)$^+$]; mp 232° C.

EXAMPLE 4.35

5-(3-Fluoro-4-trifluoromethyl-phenyl)-3-(2-methyl-pyridin-4-yl)-7-trifluoromethyl-pyrazolo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (85 mg, 39%). MS (ISP) 441.5 [(M+H)$^+$]; mp 250° C.

EXAMPLE 4.36

5-(3-Methyl-4-trifluoromethyl-phenyl)-3-pyridin-3-yl-7-trifluoromethyl-pyrazolo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 3-amino-4-(3-pyridinyl)-pyrazole [CAS No. 40545-68-2; prepared from 3-cyanomethyl -pyridine as described in Bioorg. Med. Chem. Lett. 12 (2002) 3537-3541] (80 mg, 0.5 mmol) according to general procedure B yielded the title compound as an orange solid (116 mg, 55%). MS (ISP) 423.3 [(M+H)$^+$]; mp 177° C.

EXAMPLE 4.37

5-(3-Methyl-4-trifluoromethyl-phenyl)-3-pyridin-4-yl-7-trifluoromethyl-pyrazolo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl -pyridine as described in Bioorg. Med. Chem. Lett. 12 (2002) 3537-3541] (80 mg, 0.5 mmol) according to general procedure B yielded the title compound as a yellow solid (104 mg, 49%). MS (ISP) 423.3 [(M+H)$^+$]; mp 227° C.

EXAMPLE 4.38

5-(3-Methyl-4-trifluoromethyl-phenyl)-3-(2,6-dimethyl-pyridin-4-yl)-7-trifluoromethyl-pyrazolo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (107 mg, 48%). MS (ISP) 451.5 [(M+H)$^+$]; mp 253° C.

EXAMPLE 4.39

5-(3-Methyl-4-trifluoromethyl-phenyl)-3-(2-methyl-pyridin-4-yl)-7-trifluoromethyl-pyrazolo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (113 mg, 52%). MS (ISP) 437.5 [(M+H)$^+$]; mp 237° C.

EXAMPLE 4.40

5-(4-Ethoxy-3-trifluoromethyl-phenyl)-3-pyridin-3-yl-7-trifluoromethyl-pyrazolo[1,5-a]pyrimidine Reaction of 1-(4-ethoxy-3-trifluoromethyl-phenyl)-4,4,4-trifluoro-butane-1,3-dione (164 mg, 0.5 mmol), prepared from 4-ethoxy-3-trifluoromethyl-acetophenone (synthesis: see part acetophenone derivatives) according to general procedure A, and 3-amino-4-(3-pyridinyl)-pyrazole [CAS No. 40545-68-2; prepared from 3-cyanomethyl -pyridine as described in Bioorg. Med. Chem. Lett. 12 (2002) 3537-3541] (80 mg, 0.5 mmol) according to general procedure B yielded the title compound as a yellow solid (155 mg, 68%). MS (ISP) 453.5 [(M+H)$^+$]; mp 178° C.

EXAMPLE 4.41

5-(4-Ethoxy-3-trifluoromethyl-phenyl)-3-pyridin-4-yl-7-trifluoromethyl-pyrazolo[1,5-a]pyrimidine Reaction of 1-(4-ethoxy-3-trifluoromethyl-phenyl)-4,4,4-trifluoro-butane-1,3-dione (1164 mg, 0.5 mmol), prepared from 4-ethoxy-3-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (128 mg, 57%). MS (ISP) 453.5 [(M+H)$^+$]; mp 233° C.

EXAMPLE 4.42

5-(4-Trifluoroethoxy-3-trifluoromethyl-phenyl)-3-pyridin-3-yl-7-trifluoromethyl -pyrazolo[1,5-a]pyrimidine Reaction of 1-(4-trifluoroethoxy-3-trifluoromethyl-phenyl)-4,4,4-trifluoro-butane-1,3-dione (191 mg, 0.5 mmol), prepared from 4-trifluoroethoxy-3-trifluoromethyl -acetophenone (synthesis: see part acetophenone derivatives) according to general procedure A, and 3-amino-4-(3-pyridinyl)-pyrazole [CAS No. 40545-68-2; prepared from 3-cyanomethyl-pyridine as described in Bioorg. Med. Chem. Lett. 12 (2002) 3537-3541] (80 mg, 0.5 mmol) according to general procedure B yielded the title compound as a yellow solid (174 mg, 69%). MS (ISP) 507.5 [(M+H)$^+$]; mp 181° C.

EXAMPLE 4.43

5-[4-(2,2,2-Trifluorothoxy)-3-trifluoromethyl-phenyl]-3-pyridin-4-yl-7-trifluoromethyl-pyrazolo[1,5-a]pyrimidine Reaction of 1-[4-(2,2,2-trifluoroethoxy)-3-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) accord-

EXAMPLE 4.44

5-(4-Ethoxy-3-trifluoromethyl-phenyl)-3-(2-methyl-pyridin-4-yl)-7-trifluoromethyl-pyrazolo[1,5-a]pyrimidine Reaction of 1-(4-ethoxy-3-trifluoromethyl-phenyl)-4,4,4-trifluoro-butane-1,3-dione (164 mg, 0.5 mmol), prepared from 4-ethoxy-3-trifluoromethyl-acetophenone (synthesis: see part acetophenone derivatives) according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (145 mg, 62%). MS (ISP) 467.2 [(M+H)$^+$]; mp 250° C.

EXAMPLE 4.45

5-[4-(2,2,2-Trifluoroethoxy)-3-trifluoromethyl-phenyl]-3-(2,6-dimethyl-pyridin-4-yl)-7-trifluoromethyl-pyrazolo[1,5-a]pyrimidine Reaction of 1-[4-(2,2,2-trifluoroethoxy)-3-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino-4-(2,6-dimethyl-4-pyridinyl)-pyrazole [prepared from 4-cyanomethyl-2,6-dimethyl-pyridine, CAS No. 130138-46-4, see part synthesis of amino-pyrazole derivatives] (94 mg, 0.5 mmol) according to general procedure B yielded the title compound as a yellow solid (165 mg, 62%). MS (ISP) 535.5 [(M+H)$^+$]; mp 229° C.

EXAMPLE 4.46

5-[4-(2,2,2-Trifluoroethoxy)-3-trifluoromethyl-phenyl]-3-(2-methyl-pyridin-4-yl)-7-trifluoromethyl-pyrazolo[1,5-a]pyrimidine Reaction of 1-[4-(2,2,2-trifluoroethoxy)-3-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino-4-(2-methyl-4-pyridinyl)-pyrazole [see part synthesis of amino-pyrazole derivatives] (87 mg, 0.5 mmol) according to general procedure B yielded the title compound as a yellow solid (176 mg, 68%). MS (ISP) 521.5 [(M+H)$^+$]; mp 210° C.

EXAMPLE 4.47

5-(3-Ethoxy-4-trifluoromethyl-phenyl)-3-pyridin-4-yl-7-trifluoromethyl-pyrazolo[1,5-a]pyrimidine Reaction of 1-(3-ethoxy-4-trifluoromethyl-phenyl)-4,4,4-trifluoro-butane-1,3-dione (164 mg, 0.5 mmol), prepared from 3-ethoxy-4-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (108 mg, 48%). MS (ISP) 453.1 [(M+H)$^+$]; mp 251° C.

EXAMPLE 4.48

3-(2,6-Dimethyl-pyridin-4-yl)-5-(3-ethoxy-4-trifluoromethyl-phenyl)-7-trifluoromethyl-pyrazolo[1,5-a]pyrimidine Reaction of 1-(3-ethoxy-4-trifluoromethyl-phenyl)-4,4,4-trifluoro-butane-1,3-dione (164 mg, 0.5 mmol), prepared from 3-ethoxy-4-trifluoromethyl-acetophenone (synthesis: see part acetophenone derivatives) according to general procedure A, and 3-amino-4-(2,6-dimethyl-4-pyridinyl)-pyrazole [prepared from 4-cyanomethyl-2,6-dimethyl-pyridine, CAS No. 130138-46-4, as described in Bioorg. Med. Chem. Lett. 12 (2002) 3537-3541] (94 mg, 0.5 mmol) according to general procedure B yielded the title compound as a yellow solid (120 mg, 50%). MS (ISP) 481.4 [(M+H)$^+$]; mp 257° C.

EXAMPLE 4.49

5-(3-Ethoxy-4-trifluoromethyl-phenyl)-3-(2-methyl-pyridin-4-yl)-7-trifluoromethyl-pyrazolo[1,5-a]pyrimidine Reaction of 1-(3-ethoxy-4-trifluoromethyl-phenyl)-4,4,4-trifluoro-butane-1,3-dione (164 mg, 0.5 mmol), prepared from 3-ethoxy-4-trifluoromethyl-acetophenone (synthesis: see part acetophenone derivatives) according to general procedure A, and 3-amino-4-(2-methyl-4-pyridinyl)-pyrazole [prepared from 4-cyanomethyl-2-methyl-pyridine, as described in Bioorg. Med. Chem. Lett. 12 (2002) 3537-3541] (87 mg, 0.5 mmol) according to general procedure B yielded the title compound as a yellow solid (113 mg, 49%). MS (ISP) 467.4 [(M+H)$^+$]; mp 226° C.

EXAMPLE 4.50

3-Pyridin-4-yl-5-[3-(2,2,2-trifluoro-ethoxy)-4-trifluoromethyl-phenyl]-7-trifluoromethyl-pyrazolo[1,5-a]pyrimidine Reaction of 1-[3-(2,2,2-trifluoroethoxy)-4-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (127 mg, 50%). MS (ISP) 507.4 [(M+H)$^+$]; mp 251° C.

EXAMPLE 4.51

3-(2,6-Dimethyl-pyridin-4-yl)-5-[3-(2,2,2-trifluoro-ethoxy)-4-trifluoromethyl-phenyl]-7-trifluoromethyl-pyrazolo[1,5-a]pyrimidine Reaction of 1-[3-(2,2,2-trifluoroethoxy)-4-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino- 4-(2,6-dimethyl-4-pyridinyl)-pyrazole [prepared from 4-cyanomethyl-2,6-dimethyl-pyridine, CAS No. 130138-46-4, as described in Bioorg. Med. Chem. Lett. 12 (2002) 3537-3541] (94 mg, 0.5 mmol) according to general procedure B yielded the title compound as a yellow solid (139 mg, 52%). MS (ISP) 535.4 [(M+H)$^+$]; mp 245° C.

EXAMPLE 4.52

3-(2-Methyl-pyridin-4-yl)-5-[3-(2,2,2-trifluoro-ethoxy)-4-trifluoromethyl-phenyl]-7-trifluoromethyl-pyrazolo[1,5-a]pyrimidine Reaction of 1-[3-(2,2,2-trifluoroethoxy)-4-trifluoromethyl-phenyl]-4,4,4-trifluoro-butane-1,3-dione (191 mg, 0.5 mmol), prepared from 4-(2,2,2-trifluoroethoxy)-3-trifluoromethyl-acetophenone (synthesis: see part acetophenone derivatives) according to general procedure A, and 3-amino-4-(2-methyl-4-pyridinyl)-pyrazole [prepared from 4-cyanomethyl-2-methyl-pyridine, as described in Bioorg. Med. Chem. Lett. 12 (2002) 3537-3541] (87 mg, 0.5 mmol) according to general procedure B yielded the title compound as a yellow solid (140 mg, 54%). MS (ISP) 521.4 [(M+H)$^+$]; mp 201° C.

EXAMPLE 4.53

5-(3,4-Bis-trifluoromethyl-phenyl)-3-pyridin-4-yl-7-trifluoromethyl-pyrazolo[1,5-a]pyrimidine Reaction of 1-(3,4-bis-trifluoromethyl-phenyl)-4,4,4-trifluoro-butane-1,3-dione (176 mg, 0.5 mmol), prepared from commercially available 3,4-bis-trifluoromethyl-acetophenone [CAS No. 129604-25-7] according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (83 mg, 35%). Yellow solid. MS (ISP) 477.2 [(M+H)$^+$]; mp 209° C.

EXAMPLE 4.54

5-(3,4-Bis-trifluoromethyl-phenyl)-3-(2-methyl-pyridin-4-yl)-7-trifluoromethyl-pyrazolo[1,5-a]pyrimidine Reaction of 1-(3,4-bis-trifluoromethyl-phenyl)-4,4,4-trifluoro-butane-1,3-dione (176 mg, 0.5 mmol), prepared from commercially available 3,4-bis-trifluoromethyl-acetophenone [CAS No. 129604-25-7] according to general procedure A, and 3-amino-4-(2-methyl-4-pyridinyl)-pyrazole [prepared from 4-cyanomethyl-2-methyl-pyridine, as described in Bioorg. Med. Chem. Lett. 12 (2002) 3537-3541] (87 mg, 0.5 mmol) according to general procedure B yielded the title compound as a yellow solid (93 mg, 38%). MS (ISP) 491.3 [(M+H)$^+$]; mp 223° C.

EXAMPLE 4.55

5-(4-Bromo-phenyl)-3-pyridin-4-yl-7-trifluoromethyl-pyrazolo[1,5-a]pyrimidine

Reaction of 1-(4-bromo-phenyl)-4,4,4-trifluoro-butane-1,3-dione (148 mg, 0.5 mmol), prepared from commercially available 4-bromo-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (79 mg, 38%). MS (ISP) 421.2 [(M+H)$^+$]; mp 289° C.

EXAMPLE 4.56

5-(4-Bromo-phenyl)-3-(2-methyl-pyridin-4-yl)-7-trifluoromethyl-pyrazolo[1,5-a]pyrimidine Reaction of 1-(4-bromo-phenyl)-4,4,4-trifluoro-butane-1,3-dione (148 mg, 0.5 mmol), prepared from commercially available 4-bromo-acetophenone according to general procedure A, and 3-amino-4-(2-methyl-4-pyridinyl)-pyrazole [prepared from 4-cyanomethyl-2-methyl-pyridine, as described in Bioorg. Med. Chem. Lett. 12 (2002) 3537-3541] (87 mg, 0.5 mmol) according to general procedure B yielded the title compound as a yellow solid (94 mg, 43%). MS (ISP) 433.3 [(M+H)$^+$]; mp 226° C.

EXAMPLE 4.57

5-(4-Bromo-phenyl)-3-(2,6-dimethyl-pyridin-4-yl)-7-trifluoromethyl-pyrazolo[1,5-a]pyrimidine Reaction of 1-(4-bromo-phenyl)-4,4,4-trifluoro-butane-1,3-dione (148 mg, 0.5 mmol), prepared from commercially available 4-bromo-acetophenone according to general procedure A, and 3-amino-4-(2,6-dimethyl-4-pyridinyl)-pyrazole [prepared from 4-cyanomethyl-2,6-dimethyl-pyridine, CAS No. 130138-46-4, as described in Bioorg. Med. Chem. Lett. 12 (2002) 3537-3541] (94 mg, 0.5 mmol) according to general procedure B yielded the title compound as a yellow solid (93 mg, 42%). MS (ISP) 447.2 [(M+H)$^+$]; mp 258° C.

EXAMPLE 4.58

5-(4-Methoxy-phenyl)-3-pyridin-4-yl-7-trifluoromethyl-pyrazolo[1,5-a]pyrimidine

Reaction of 1-(4-methoxy-phenyl)-4,4,4-trifluoro-butane-1,3-dione (123 mg, 0.5 mmol), prepared from commercially available 4-methoxy-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (110 mg, 59%). MS (ISP) 371.2 [(M+H)$^+$]; mp 244° C.

EXAMPLE 5

Preparation of phenyl-4-trifluoromethyl-imidazo[1,5-a]pyrimidine-8-carbonitriles and pyridinyl-4-trifluoromethyl-imidazo[1,5-a]pyrimidine-8-carbonitriles A stirred mixture of commercially available 4-amino-5-cyano-1H-imidazole (1 eq.) and a 1-phenyl-4,4,4-trifluoro-butane-1,3-dione or 1-pyridin-2-yl-4,4,4-trifluoro-butane-1,3-dione (1 eq.), prepared according to general procedure A, in acetic acid was heated under reflux conditions for 3.5 h. The reaction mixture was evaporated and the product was isolated by column chromatography (heptane/ethyl acetate) and further purified by crystallization. If the product precipitates during the reaction it can be isolated by filtration and further purified by crystallization.

| Ex. | dione | compound name | MS (ISP)/mp |
|---|---|---|---|
| 5.1 | S1.23 | 2-phenyl-4-trifluoromethyl-imidazo[1,5-a]pyrimidine-8-carbonitrile | 289.0 [(M + H)+] mp 202° C. |
| 5.2 | S1.17 | 2-(4-chloro-phenyl)-4-trifluoromethyl-imidazo[1,5-a]pyrimidine-8-carbonitrile | 323.1 [(M + H)+] mp 205° C. |
| 5.3 | S1.1 | 2-(3-chloro-phenyl)-4-trifluoromethyl-imidazo[1,5-a]pyrimidine-8-carbonitrile | 323.1 [(M + H)+] mp 221° C. |
| 5.4 | S1.2 | 2-(4-methyl-phenyl)-4-trifluoromethyl-imidazo[1,5-a]pyrimidine-8-carbonitrile | 303.1 [(M + H)+] mp 197° C. |
| 5.5 | S1.24 | 2-(4-methoxy-phenyl)-4-trifluoromethyl-imidazo[1,5-a]pyrimidine-8-carbonitrile | 319.1 [(M + H)+] mp 192° C. |
| 5.6 | S1.3 | 2-(2-chloro-phenyl)-4-trifluoromethyl-imidazo[1,5-a]pyrimidine-8-carbonitrile | 323.1 [(M + H)+] mp 180° C. |
| 5.7 | S1.4 | 2-(2,4-dichloro-phenyl)-4-trifluoromethyl-imidazo[1,5-a]pyrimidine-8-carbonitrile | 357.0 [(M + H)+] mp 139° C. |
| 5.8 | S1.25 | 2-(2-methyl-phenyl)-4-trifluoromethyl-imidazo[1,5-a]pyrimidine-8-carbonitrile | 303.0 [(M + H)+] mp 151° C. |
| 5.9 | S1.5 | 2-(3-methyl-phenyl)-4-trifluoromethyl-imidazo[1,5-a]pyrimidine-8-carbonitrile | 302.9 [(M + H)+] mp 202° C. |
| 5.10 | S1.2 | 2-(4-trifluoromethyl-phenyl)-4-trifluoromethyl-imidazo[1,5-a]pyrimidine-8-carbonitrile | 357.0 [(M + H)+] mp 236° C. |
| 5.11 | S1.6 | 2-(3-trifluoromethyl-phenyl)-4-trifluoromethyl-imidazo[1,5-a]pyrimidine-8-carbonitrile | 357.0 [(M + H)+] mp 202° C. |
| 5.12 | S1.8 | 5-(3-fluoro-phenyl)-7-trifluoromethyl-imidazo[1,5-a]pyrimidine-8-carbonitrile | 307.0 [(M + H)+] mp 210° C. |
| 5.13 | S1.9 | 5-(4-fluoro-phenyl)-7-trifluoromethyl-imidazo[1,5-a]pyrimidine-8-carbonitrile | 307.0 [(M + H)+] mp 206° C. |
| 5.14 | S1.10 | 5-(2,4-difluoro-phenyl)-7-trifluoromethyl-imidazo[1,5-a]pyrimidine-8-carbonitrile | 325.2 [(M + H)+] mp 169° C. |
| 5.15 | S1.11 | 5-(2-fluoro-phenyl)-7-trifluoromethyl-imidazo[1,5-a]pyrimidine-8-carbonitrile | 307.1 [(M + H)+] mp 147° C. |
| 5.16 | S1.12 | 5-(3,4-difluoro-phenyl)-7-trifluoromethyl-imidazo[1,5-a]pyrimidine-8-carbonitrile | 325.2 [(M + H)+] mp 187° C. |
| 5.17 | S1.13 | 5-(4-fluoro-3-trifluoromethyl-phenyl)-7-trifluoromethyl-imidazo[1,5-a]pyrimidine-8-carbonitrile | 375.3 [(M + H)+] mp 207° C. |
| 5.18 | S1.14 | 5-(3-chloro-4-fluoro-phenyl)-7-trifluoromethyl-imidazo[1,5-a]pyrimidine-8-carbonitrile | 341.1 [(M + H)+] mp 195° C. |
| 5.19 | S1.15 | 5-(4-chloro-3-methyl-phenyl)-7-trifluoromethyl-imidazo[1,5-a]pyrimidine-8-carbonitrile | 337.1 [(M + H)+] mp 238° C. |
| 5.20 | S1.16 | 5-(3,4-dichloro-phenyl)-7-trifluoromethyl-imidazo[1,5-a]pyrimidine-8-carbonitrile | 357.2 [(M + H)+] mp 219° C. |
| 5.21 | S1.18 | 5-(3-fluoro-4-trifluoromethyl-phenyl)-7-trifluoromethyl-imidazo[1,5-a]pyrimidine-8-carbonitrile | 375.0 [(M + H)+] mp 210° C. |
| 5.22 | S1.21 | 2-(4-methyl-3-trifluoromethyl-phenyl)-4-trifluoromethyl-imidazo[1,5-a]pyrimidine-8-carbonitrile | 371.1 [(M + H)+] mp 220° C. |
| 5.23 | S1.19 | 2-(3-methyl-4-trifluoromethyl-phenyl)-4-trifluoromethyl-imidazo[1,5-a]pyrimidine-8-carbonitrile | 371.1 [(M + H)+] mp 217° C. |
| 5.24 | S1.20 | 2-(4-trifluoroethoxy-3-trifluoromethyl-phenyl)-4-trifluoromethyl-imidazo[1,5-a]pyrimidine-8-carbonitrile | 453.0 [M+] mp 189° C. |
| 5.25 | S2.1 | 2-pyridin-2-yl-4-trifluoromethyl-imidazo[1,5-a]pyrimidine-8-carbonitrile | 289.9 [(M + H)+] mp 205° C. |
| 5.26 | S2.2 | 2-pyridin-3-yl-4-trifluoromethyl-imidazo[1,5-a]pyrimidine-8-carbonitrile | 290.1 [(M + H)+] mp 222° C. |
| 5.27 | S2.3 | 2-pyridin-4-yl-4-trifluoromethyl-imidazo[1,5-a]pyrimidine-8-carbonitrile | 289.8 [(M + H)+] mp 254° C. |

EXAMPLE 5.1

2-Phenyl-4-trifluoromethyl-imidazo[1,5-a]pyrimidine-8-carbonitrile

Reaction of 1-phenyl-4,4,4-trifluoro-butane-1,3-dione (216 mg, 1.0 mmol), prepared from commercially available acetophenone according to general procedure A, and 4-amino-5-cyano-1H-imidazole (108 mg, 1.0 mmol) according to general procedure B yielded the title compound as a yellow solid (107 mg, 37%). MS (ISP) 289.0 [(M+H)$^+$]; mp 202° C.

EXAMPLE 5.2

2-(4-Chloro-phenyl)-4-trifluoromethyl-imidazo[1,5-a]pyrimidine-8-carbonitrile

Reaction of 1-(4-chloro-phenyl)-4,4,4-trifluoro-butane-1,3-dione (251 mg, 1.0 mmol), prepared from commercially available 4-chloro-acetophenone according to general procedure A, and 4-amino-5-cyano-1H-imidazole (108 mg, 1.0 mmol) according to general procedure B yielded the title compound as a yellow solid (124 mg, 38%). MS (ISP) 323.1 [(M+H)$^+$]; mp 205° C.

EXAMPLE 5.3

2-(3-Chloro-phenyl)-4-trifluoromethyl-imidazo[1,5-a]pyrimidine-8-carbonitrile

Reaction of 1-(3-chloro-phenyl)-4,4,4-trifluoro-butane-1,3-dione (251 mg, 1.0 mmol), prepared from commercially available 3-chloro-acetophenone according to general procedure A, and 4-amino-5-cyano-1H-imidazole (108 mg, 1.0 mmol) according to general procedure B yielded the title compound as a yellow solid (133 mg, 41%). MS (ISP) 323.1 [(M+H)$^+$]; mp 221° C.

EXAMPLE 5.4

2-(4-Methyl-phenyl)-4-trifluoromethyl-imidazo[1,5-a]pyrimidine-8-carbonitrile

Reaction of 1-(4-methyl-phenyl)-4,4,4-trifluoro-butane-1,3-dione (230 mg, 1.0 mmol), prepared from commercially available 4-methyl-acetophenone according to general procedure A, and 4-amino-5-cyano-1H-imidazole (108 mg, 1.0 mmol) according to general procedure B yielded the title compound as a yellow solid (133 mg, 44%). MS (ISP) 303.1 [(M+H)$^+$]; mp 197° C.

EXAMPLE 5.5

2-(4-Methoxy-phenyl)-4-trifluoromethyl-imidazo[1,5-a]pyrimidine-8-carbonitrile

Reaction of 1-(4-methoxy-phenyl)-4,4,4-trifluoro-butane-1,3-dione (246 mg, 1.0 mmol), prepared from commercially available 4-methoxy-acetophenone according to general procedure A, and 4-amino-5-cyano-1H-imidazole (108 mg, 1.0 mmol) according to general procedure B yielded the title compound as a yellow solid (125 mg, 39%). MS (ISP) 319.1 [(M+H)$^+$]; mp 192° C.

EXAMPLE 5.6

2-(2-Chloro-phenyl)-4-trifluoromethyl-imidazo[1,5-a]pyrimidine-8-carbonitrile

Reaction of 1-(2-chloro-phenyl)-4,4,4-trifluoro-butane-1,3-dione (251 mg, 1.0 mmol), prepared from commercially available 2-chloro-acetophenone according to general procedure A, and 4-amino-5-cyano-1H-imidazole (108 mg, 1.0 mmol) according to general procedure B yielded the title compound as a yellow solid (55 mg, 17%). MS (ISP) 323.1 [(M+H)$^+$]; mp 180° C.

EXAMPLE 5.7

2-(2,4-Dichloro-phenyl)-4-trifluoromethyl-imidazo[1,5-a]pyrimidine-8-carbonitrile Reaction of 1-(2,4-dichloro-phenyl)-4,4,4-trifluoro-butane-1,3-dione (285 mg, 1.0 mmol), prepared from commercially available 2,4-dichloro-acetophenone according to general procedure A, and 4-amino-5-cyano-1H-imidazole (108 mg, 1.0 mmol) according to general procedure B yielded the title compound as a yellow solid (43 mg, 12%). MS (ISP) 357.0 [(M+H)$^+$]; mp 139° C.

EXAMPLE 5.8

2-(2-Methyl-phenyl)-4-trifluoromethyl-imidazo[1,5-a]pyrimidine-8-carbonitrile

Reaction of 1-(2-methyl-phenyl)-4,4,4-trifluoro-butane-1,3-dione (230 mg, 1.0 mmol), prepared from commercially available 2-methyl-acetophenone according to general procedure A, and 4-amino-5-cyano-1H-imidazole (108 mg, 1.0 mmol) according to general procedure B yielded the title compound as a yellow solid (19 mg, 6%). MS (ISP) 303.0 [(M+H)$^+$]; mp 151° C.

EXAMPLE 5.9

2-(3-Methyl-phenyl)-4-trifluoromethyl-imidazo[1,5-a]pyrimidine-8-carbonitrile

Reaction of 1-(3-methyl-phenyl)-4,4,4-trifluoro-butane-1,3-dione (230 mg, 1.0 mmol), prepared from commercially available 3-methyl-acetophenone according to general procedure A, and 4-amino-5-cyano-1H-imidazole (108 mg, 1.0 mmol) according to general procedure B yielded the title compound as a yellow solid (161 mg, 53%). MS (ISP) 302.9 [(M+H)$^+$]; mp 202° C.

EXAMPLE 5.10

2-(4-Trifluoromethyl-phenyl)-4-trifluoromethyl-imidazo[1,5-a]pyrimidine-8-carbonitrile Reaction of 1-(4-trifluoromethyl-phenyl)-4,4,4-trifluoro-butane-1,3-dione (284 mg, 1.0 mmol), prepared from commercially available 4-trifluoromethyl-acetophenone according to general procedure A, and 4-amino-5-cyano-1H-imidazole (108 mg, 1.0 mmol) according to general procedure B yielded the title compound as a yellow solid (151 mg, 42%). MS (ISP) 357.0 [(M+H)$^+$]; mp 236° C.

EXAMPLE 5.11

2-(3-Trifluoromethyl-phenyl)-4-trifluoromethyl-imidazo[1,5-a]pyrimidine-8-carbonitrile Reaction of 1-(3-trifluoromethyl-phenyl)-4,4,4-trifluoro-butane-1,3-dione (284 mg, 1.0 mmol), prepared from commercially available 3-trifluoromethyl-acetophenone according to general procedure A, and 4-amino-5-cyano-1H-imidazole (108 mg, 1.0 mmol) according to general procedure B yielded the title compound as a yellow solid (125 mg, 35%). MS (ISP) 357.0 [(M+H)$^+$]; mp 202° C.

EXAMPLE 5.12

5-(3-Fluoro-phenyl)-7-trifluoromethyl-imidazo[1,5-a]pyrimidine-8-carbonitrile

Reaction of 1-(3-fluoro-phenyl)-4,4,4-trifluoro-butane-1,3-dione (234 mg, 1.0 mmol), prepared from commercially available 3-fluoro-acetophenone according to general procedure A, and 4-amino-5-cyano-1H-imidazole (108 mg, 1.0 mmol) according to general procedure B yielded the title compound as a yellow solid (128 mg, 42%). MS (ISP) 307.0 [(M+H)$^+$]; mp 210° C.

EXAMPLE 5.13

5-(4-Fluoro-phenyl)-7-trifluoromethyl-imidazo[1,5-a]pyrimidine-8-carbonitrile

Reaction of 1-(4-fluoro-phenyl)-4,4,4-trifluoro-butane-1,3-dione (234 mg, 1.0 mmol), prepared from commercially available 4-fluoro-acetophenone according to general procedure A, and 4-amino-5-cyano-1H-imidazole (108 mg, 1.0 mmol) according to general procedure B yielded the title compound as a yellow solid (119 mg, 39%). MS (ISP) 307.0 [(M+H)$^+$]; mp 206° C.

EXAMPLE 5.14

5-(2,4-Difluoro-phenyl)-7-trifluoromethyl-imidazo[1,5-a]pyrimidine-8-carbonitrile Reaction of 1-(2,4-difluoro-phenyl)-4,4,4-trifluoro-butane-1,3-dione (252 mg, 1.0 mmol), prepared from commercially available 2,4-difluoro-acetophenone according to general procedure A, and 4-amino-5-cyano-1H-imidazole (108 mg, 1.0 mmol) according to general procedure B yielded the title compound as a yellow solid (75 mg, 23%). MS (ISP) 325.2 [(M+H)$^+$]; mp 169° C.

EXAMPLE 5.15

5-(2-Fluoro-phenyl)-7-trifluoromethyl-imidazo[1,5-a]pyrimidine-8-carbonitrile

Reaction of 1-(2-fluoro-phenyl)-4,4,4-trifluoro-butane-1,3-dione (234 mg, 1.0 mmol), prepared from commercially available 2-fluoro-acetophenone according to general procedure A, and 4-amino-5-cyano-1H-imidazole (108 mg, 1.0 mmol) according to general procedure B yielded the title compound as a yellow solid (99 mg, 32%). MS (ISP) 307.1 [(M+H)$^+$]; mp 147° C.

EXAMPLE 5.16

5-(3,4-Difluoro-phenyl)-7-trifluoromethyl-imidazo[1,5-a]pyrimidine-8-carbonitrile Reaction of 1-(3,4-difluoro-phenyl)-4,4,4-trifluoro-butane-1,3-dione (252 mg, 1.0 mmol), prepared from commercially available 3,4-difluoro-acetophenone according to general procedure A, and 4-amino-5-cyano-1H-imidazole (108 mg, 1.0 mmol) according to general procedure B yielded the title compound as a yellow solid (107 mg, 33%). MS (ISP) 325.2 [(M+H)$^+$]; mp 187° C.

EXAMPLE 5.17

5-(4-Fluoro-3-trifluoromethyl-phenyl)-7-trifluoromethyl-imidazo[1,5-a]pyrimidine-8-carbonitrile Reaction of 1-(4-fluoro-3-trifluoromethyl-phenyl)-4,4,4-trifluoro-butane-1,3-dione (302 mg, 1.0 mmol), prepared from commercially available 4-fluoro-3-trifluoromethyl-acetophenone according to general procedure A, and 4-amino-5-cyano-1H-imidazole (108 mg, 1.0 mmol) according to general procedure B yielded the title compound as a yellow solid (141 mg, 38%). MS (ISP) 375.3 [(M+H)$^+$]; mp 207° C.

EXAMPLE 5.18

5-(3-Chloro-4-fluoro-phenyl)-7-trifluoromethyl-imidazo[1,5-a]pyrimidine-8-carbonitrile Reaction of 1-(3-chloro-4-fluoro-phenyl)-4,4,4-trifluoro-butane-1,3-dione (269 mg, 1.0 mmol), prepared from commercially available 3-chloro-4-fluoro-acetophenone according to general procedure A, and 4-amino-5-cyano-1H-imidazole (108 mg, 1.0 mmol) according to general procedure B yielded the title compound as a yellow solid (120 mg, 35%). MS (ISP) 341.1 [(M+H)$^+$]; mp 195° C.

EXAMPLE 5.19

5-(4-Chloro-3-methyl-phenyl)-7-trifluoromethyl-imidazo[1,5-a]pyrimidine-8-carbonitrile Reaction of 1-(4-chloro-3-methyl-phenyl)-4,4,4-trifluoro-butane-1,3-dione (265 mg, 1.0 mmol), prepared from commercially available 4-chloro-3-methyl-acetophenone according to general procedure A, and 4-amino-5-cyano-1H-imidazole (108 mg, 1.0 mmol) according to general procedure B yielded the title compound as a yellow solid (171 mg, 51%). MS (ISP) 337.1 [(M+H)$^+$]; mp 238° C.

EXAMPLE 5.20

5-(3,4-Dichloro-phenyl)-7-trifluoromethyl-imidazo[1,5-a]pyrimidine-8-carbonitrile Reaction of 1-(3,4-dichloro-phenyl)-4,4,4-trifluoro-butane-1,3-dione (285 mg, 1.0 mmol), prepared from commercially available 3,4-dichloro-acetophenone according to general procedure A, and 4-amino-5-cyano-1H-imidazole (108 mg, 1.0 mmol) according to general procedure B yielded the title compound as a yellow solid (161 mg, 45%). MS (ISP) 357.2 [(M+H)$^+$]; mp 219° C.

EXAMPLE 5.21

5-(3-Fluoro-4-trifluoromethyl-phenyl)-7-trifluoromethyl-imidazo[1,5-a]pyrimidine-8-carbonitrile Reaction of 1-(3-fluoro-4-trifluoromethyl-phenyl)-4,4,4-trifluoro-butane-1,3-dione (302 mg, 1.0 mmol), prepared from commercially available 3-fluoro-4-trifluoromethyl-acetophenone according to general procedure A, and 4-amino-5-cyano-1H-imidazole (108 mg, 1.0 mmol) according to general procedure B yielded the title compound as a yellow solid (110 mg, 29%). MS (ISP) 375.0 [(M+H)$^+$]; mp 210° C.

EXAMPLE 5.22

2-(4-Methyl-3-trifluoromethyl-phenyl)-4-trifluoromethyl-imidazo[1,5-a]pyrimidine-8-carbonitrile Reaction of 1-(4-methyl-3-trifluoromethyl-phenyl)-4,4,4-trifluoro-butane-1,3-dione (298 mg, 1.0 mmol), prepared from 4-methyl-3-trifluoromethyl-acetophenone (synthesis: see part acetophenone derivatives) according to general procedure A, and 4-amino-5-cyano-1H-imidazole (108 mg, 1.0 mmol) according to general procedure B yielded the title compound as a yellow solid (143 mg, 39%). MS (ISP) 371.1 [(M+H)$^+$]; mp 220° C.

EXAMPLE 5.23

2-(3-Methyl-4-trifluoromethyl-phenyl)-4-trifluoromethyl-imidazo[1,5-a]pyrimidine-8-carbonitrile Reaction of 1-(3-methyl-4-trifluoromethyl-phenyl)-4,4,4-trifluoro-butane-1,3-dione (224 mg, 0.75 mmol), prepared from 3-methyl-4-trifluoromethyl-acetophenone (synthesis: see part acetophenone derivatives) according to general procedure A, and 4-amino-5-cyano-1H-imidazole (81 mg, 0.75 mmol) according to general procedure B yielded the title compound as a yellow solid (131 mg, 47%). MS (ISP) 371.1 [(M+H)$^+$]; mp 217° C.

EXAMPLE 5.24

2-(4-Trifluoroethoxy-3-trifluoromethyl-phenyl)-4-trifluoromethyl-imidazo[1,5-a]pyrimidine-8-carbonitrile Reaction of 1-(4-trifluoroethoxy-3-trifluoromethyl-phenyl)-4,4,4-trifluoro-butane-1,3-dione (382 mg, 1.0 mmol), prepared from 4-trifluoroethoxy-3-trifluoromethyl -acetophenone (synthesis: see part acetophenone derivatives) according to general procedure A, and 4-amino-5-cyano-1H-imidazole (108 mg, 1.0 mmol) according to general procedure B yielded the title compound as a yellow solid (182 mg, 40%). MS (ISP) 453.0 [M$^+$]; mp 189° C.

EXAMPLE 5.25

2-Pyridin-2-yl-4-trifluoromethyl-imidazo[1,5-a]pyrimidine-8-carbonitrile

Reaction of 1-pyridin-2-yl-4,4,4-trifluoro-butane-1,3-dione (217 mg, 1.0 mmol), prepared from commercially available 2-acetylpyridine according to general procedure A, and 4-amino-5-cyano-1H-imidazole (108 mg, 1.0 mmol) according to general procedure B yielded the title compound as a yellow solid (135 mg, 47%). MS (ISP) 289.9 [(M+H)$^+$]; mp 205° C.

EXAMPLE 5.26

2-Pyridin-3-yl-4-trifluoromethyl-imidazo[1,5-a]pyrimidine-8-carbonitrile

Reaction of 1-pyridin-3-yl-4,4,4-trifluoro-butane-1,3-dione (217 mg, 1.0 mmol), prepared from commercially available 3-acetylpyridine according to general procedure A, and 4-amino-5-cyano-1H-imidazole (108 mg, 1.0 mmol) according to general procedure B yielded the title compound as a yellow solid (37 mg, 13%). MS (ISP) 290.1 [(M+H)$^+$]; mp 222° C.

EXAMPLE 5.27

2-Pyridin-4-yl-4-trifluoromethyl-imidazo[1,5-a]pyrimidine-8-carbonitrile

Reaction of 1-pyridin-4-yl-4,4,4-trifluoro-butane-1,3-dione (217 mg, 1.0 mmol), prepared from commercially available 4-acetylpyridine according to general procedure A, and 4-amino-5-cyano-1H-imidazole (108 mg, 1.0 mmol) according to general procedure B yielded the title compound as a yellow solid (77 mg, 27%). MS (ISP) 289.8 [(M+H)$^+$]; mp 254° C.

EXAMPLE 6

5-phenyl)-3-(2-hydroxymethyl-pyridin-4-yl)-7-trifluoromethyl-pyrazolo[1,5-a]pyrimidines (General Procedure C)

General Procedure C:

To a stirred solution of a 5-phenyl-3-(2-methyl-pyridin-4-yl)-7-trifluoromethyl -pyrazolo[1,5-a]pyrimidine prepared according to general procedure B (example 4) in dichloromethane MeOH and 3-chloro-perbenzoic acid are added at RT. The solution is stirred at RT for about 17 h, sat. NaHCO$_3$ solution and dichloromethane is added and the mixture was stirred for about 30 min. The organic layer is separated, washed with a Na$_2$S$_2$O$_3$ solution, sat. NaHCO$_3$ solution, brine and dried (Mg$_2$SO$_4$). Evaporation of the solvent yields a crude 5-phenyl-3-(2-methyl-1-oxo-pyridin-4-yl)-7-trifluoromethyl-pyrazolo[1,5-a]pyrimidine compound as a solid, which can be used without further purification.

b) A stirred mixture of a 5-phenyl-3-(2-methyl-1-oxo-pyridin-4-yl)-7-trifluoromethyl-pyrazolo[1,5-a]pyrimidine compound and acetic acid anhydride is refluxed for about 30 min, poured into sat. NaHCO$_3$ solution and extracted with dichloromethane (e.g. 3 times 20 ml). The combined organic layers is washed with brine and dried (MgSO$_4$). Purification of the crude product by column chromatography on silica gel (ethyl acetate/hexane 1:1) yields a 4-[5-phenyl-7-trifluoromethyl-pyrazolo[1,5-a]pyrimidin-3-yl]-pyridin-2-ylmethyl acetate compound as a solid.

c) To a stirred solution of said 4-[5-phenyl-7-trifluoromethyl-pyrazolo[1,5-a]pyrimidin-3-yl]-pyridin-2-ylmethyl acetate compound in MeOH is added at RT NaOMe. The reaction mixture is stirred for about 17 h, poured into water and extracted with dichloromethane (e.g. 3 times 40 ml). The combined organic layers is washed with brine, dried (MgSO$_4$) and evaporated. The crude product can be further purified by column chromatography on silica gel (e.g. ethyl acetate) to yield the title compounds as a solid.

| Ex. | Pyrimidine compound | compound name | MS (ISP)/mp |
|---|---|---|---|
| 6.1 | 4.33 | 5-(4-Trifluoromethyl-phenyl)-3-(2-hydroxymethyl-pyridin-4-yl)-7-trifluoromethyl-pyrazolo[1,5-a]pyrimidine | MS (ISP) 439.3 [(M + H)+] mp 102° C. |
| 6.2 | 4.39 | 5-(3-Methyl-4-trifluoromethyl-phenyl)-3-(2-hydroxymethyl-pyridin-4-yl)-7-trifluoromethyl-pyrazolo[1,5-a]pyrimidine | MS (ISP) 453.4 [(M + H)+] mp 231° C. |
| 6.3 | 4.30 | {4-[5-(4-Chloro-3-methyl-phenyl)-7-trifluoromethyl-pyrazolo[1,5-a]pyrimidin-3-yl]-pyridin-2-yl}-methanol | MS (ISP) 419.3 [(M + H)+] mp 220° C. |
| 6.4 | 4.32 | {4-[5-(3,4-Dichloro-phenyl)-7-trifluoromethyl-pyrazolo[1,5-a]pyrimidin-3-yl]-pyridin-2-yl}-methanol | MS (ISP) 439.2 [(M + H)+] mp 233° C. |

EXAMPLE 6.1

5-(4-Trifluoromethyl-phenyl)-3-(2-hydroxymethyl-pyridin-4-yl)-7-trifluoromethyl -pyrazolo[1,5-a]pyrimidine To a stirred solution of 5-(4-trifluoromethyl-phenyl)-3-(2-methyl-pyridin-4-yl)-7-trifluoromethyl-pyrazolo[1,5-a]pyrimidine (0.15 g, 0.36 mmol, synthesis: see example 89) in dichloromethane (3.5 ml) was added at room temperature MeOH (1 ml) and 3-chloro-perbenzoic acid (70%, 0.10 mg, 0.41 mmol). The yellow solution was stirred at RT for 17 h, sat. NaHCO₃ solution (10 ml) and dichloromethane (10 ml) was added and the mixture was stirred for 30 min. The organic layer was separated, washed with 10% $Na_2S_2O_3$ solution (10 ml), sat. NaHCO₃ solution (20 ml), brine (30 ml) and dried (MgSO₄). Evaporation of the solvent yielded crude 5-(4-trifluoromethyl-phenyl)-3-(2-methyl-1-oxo-pyridin-4-yl)-7-trifluoromethyl-pyrazolo[1,5-a]pyrimidine as an orange solid (0.16 g), which was used without further purification.

b) A stirred mixture of 5-(4-trifluoromethyl-phenyl)-3-(2-methyl-1-oxo-pyridin-4-yl)-7-trifluoromethyl-pyrazolo[1,5-a]pyrimidine (0.15 g, 0.33 mmol) and acetic acid anhydride (1 ml) was refluxed for 30 min, poured into sat. NaHCO₃ solution (20 ml) and extracted with dichloromethane (3 times 20 ml). The combined organic layers were washed with brine (50 ml) and dried (MgSO₄). Purification of the crude product by column chromatography on silica gel (ethyl acetate/hexane 1:1) yielded 4-[5-(4-trifluoromethyl-phenyl)-7-trifluoromethyl-pyrazolo[1,5-a]pyrimidin-3-yl]-pyridin -2-ylmethyl acetate (0.16 g, 99%) as a brown solid.

c) To a stirred solution of 4-[5-(4-trifluoromethyl-phenyl)-7-trifluoromethyl -pyrazolo[1,5-a]pyrimidin-3-yl]-pyridin-2-ylmethyl acetate (0.16 g, 0.33 mmol) in MeOH (1 ml) was added at room temperature NaOMe (5.4M in MeOH, 0.2 ml). The reaction mixture was stirred for 17 h, poured into water (40 ml) and extracted with dichloromethane (3 times 40 ml). The combined organic layers were washed with brine (100 ml), dried (MgSO₄) and evaporated. The crude product was further purified by column chromatography on silica gel (ethyl acetate) to yield the title compound (112 mg, 78%) as an orange solid. MS (ISP) 439.3 [(M+H)+]; mp 2102° C.

EXAMPLE 6.2

5-(3-Methyl-4-trifluoromethyl-phenyl)-3-(2-hydroxymethyl-pyridin-4-yl)-7-trifluoromethyl-pyrazolo[1,5-a]pyrimidine Transformation of 5-(3-methyl-4-trifluoromethyl-phenyl)-3-(2-methyl-pyridin-4-yl)-7-trifluoromethyl-pyrazolo[1,5-a]pyrimidine (0.34 g, 0.78 mmol, synthesis: see example 96) according to the general method of example 108 yielded the title compound (80 mg, 23%) as an orange solid. MS (ISP) 453.4 [(M+H)+]; mp 231° C.

EXAMPLE 6.3

{4-[5-(4-Chloro-3-methyl-phenyl)-7-trifluoromethyl-pyrazolo[1,5-a]pyrimidin-3-yl]-pyridin-2-yl}-methanol Transformation of 5-(4-chlor-3-methyl-phenyl)-3-(2-methyl-pyridin-4-yl)-7-trifluoromethyl-pyrazolo[1,5-a]pyrimidine (0.40 g, 1.0 mmol, synthesis: see example 86) according to the general method of example 108 yielded the title compound (140 mg, 33%) as an orange solid. MS (ISP) 419.3 [(M+H)+]; mp 220° C.

EXAMPLE 6.4

{4-[5-(3,4-Dichloro-phenyl)-7-trifluoromethyl-pyrazolo[1,5-a]pyrimidin-3-yl]-pyridin-2-yl}-methanol Transformation of 5-(3,4-dichloro-phenyl)-3-(2-methyl-pyridin-4-yl)-7-trifluoromethyl-pyrazolo[1,5-a]pyrimidine (0.43 g, 1.0 mmol, synthesis: see example 88) according to the general method of example 108 yielded the title compound (73 mg, 17%) as an orange solid. MS (ISP) 439.2 [(M+H)+]; mp 233° C.

EXAMPLE 7

5-(4-Chloro-3-methyl-phenyl)-3-(2-methyl-1-oxy-pyridin-4-yl)-7-trifluoromethyl-pyrazolo[1,5-a]pyrimidine (compound no. 7.1)

To a stirred solution of 5-(4-chloro-3-methyl-phenyl)-3-(2-methyl-pyridin-4-yl) -7-trifluoromethyl-pyrazolo[1,5-a] pyrimidine (0.50 g, 1.24 mmol) in dichloromethane (12 ml) was added at RT MeOH (3 ml) and 3-chloro-perbenzoic acid (70%, 0.36 mg, 1.44 mmol). The orange solution was stirred at RT for 17 h, sat. NaHCO₃ solution (75 ml) and dichloromethane (50 ml) was added and the mixture was stirred for 30 min. The organic layer was separated, washed with 10% $Na_2S_2O_3$ solution (60 ml), sat. NaHCO₃ solution (60 ml), brine (100 ml) and dried (Mg₂SO₄). Evaporation of the solvent and crystallization yielded the title compound (0.51 g, 99%) as an orange solid. MS (ISP) 418.1 [M+]; mp 279° C.

Oxidation of 5-(3,4-dichloro-phenyl)-3-(2-methyl-pyridin-4-yl)-7-trifluoromethyl -pyrazolo[1,5-a]pyrimidine (0.63 g, 1.49 mmol) according to the above procedure yielded 5-(3,4-dichloro-phenyl)-3-(2-methyl-1-oxy-pyridin-4-yl)-7-trifluoromethyl-pyrazolo[1,5-a]pyrimidine compound no. 7.2 (0.63 g, 96%) as an orange solid. MS (ISP) 438.0 [M+]; mp 287° C.

EXAMPLE 8

Preparation of 5-phenyl-3-pyridinyl-7-trifluoromethyl-imidazol[1,5-a]pyrimidines (General Procedure B)

| Ex. | dione | compound name | MS (ISP)/mp |
|---|---|---|---|
| 8.1 | S1.15 | 2-(4-Chloro-3-methyl-phenyl)-8-pyridin-3-yl-4-trifluoromethyl-imidazo[1,5-a]pyrimidine | MS (ISP) 289.3 [(M + H)⁺] mp 210° C. |
| 8.2 | S1.17 | 2-(4-Chloro-phenyl)-8-pyridin-3-yl-4-trifluoromethyl-imidazo[1,5-a]pyrimidine | MS (ISP) 375.5 [(M + H)⁺] mp 206° C. |
| 8.3 | S1.14 | 2-(3-Chloro-4-fluoro-phenyl)-8-pyridin-3-yl-4-trifluoromethyl-imidazo[1,5-a]pyrimidine | MS (ISP) 393.1 [(M + H)⁺] mp 188° C. |
| 8.4 | S1.16 | 2-(4-Dichloro-phenyl)-8-pyridin-3-yl-4-trifluoromethyl-imidazo[1,5-a]pyrimidine | MS (ISP) 409.4 [(M + H)⁺] mp 226° C. |
| 8.5 | S1.6 | 8-Pyridin-3-yl-4-trifluoromethyl-2-(3-trifluoromethyl-phenyl)-imidazo[1,5-a]pyrimidine | MS (ISP) 409.4 [(M + H)⁺] mp 194° C. |
| 8.6 | S1.7 | 8-Pyridin-3-yl-4-trifluoromethyl-2-(4-trifluoromethyl-phenyl)-imidazo[1,5-a]pyrimidine | MS (ISP) 409.4 [(M + H)⁺] mp 231° C. |
| 8.7 | S1.21 | 2-(4-Methyl-3-trifluoromethyl-phenyl)-8-pyridin-3-yl-4-trifluoromethyl-imidazo[1,5-a]pyrimidine | MS (ISP) 423.1 [(M + H)⁺] mp 236° C. |
| 8.8 | S1.19 | 2-(3-Methyl-4-trifluoromethyl-phenyl)-8-pyridin-3-yl-4-trifluoromethyl-imidazo[1,5-a]pyrimidine | MS (ISP) 423.3 [(M + H)⁺] mp 173° C. |
| 8.9 | S1.17 | 2-(4-Chloro-phenyl)-8-pyridin-4-yl-4-trifluoromethyl-imidazo[1,5-a]pyrimidine | MS (ISP) 375.5 [(M + H)⁺] mp 290° C. |
| 8.10 | S1.15 | 2-(4-Chloro-3-methyl-phenyl)-8-pyridin-4-yl-4-trifluoromethyl-imidazo[1,5-a]pyrimidine | MS (ISP) 389.3 [(M + H)⁺] mp 254° C. |
| 8.11 | S1.14 | 2-(3-Chloro-4-fluoro-phenyl)-8-pyridin-4-yl-4-trifluoromethyl-imidazo[1,5-a]pyrimidine | MS (ISP) 393.1 [(M + H)⁺] mp 266° C. |
| 8.12 | S1.16 | 2-(4-Dichloro-phenyl)-8-pyridin-4-yl-4-trifluoromethyl-imidazo[1,5-a]pyrimidine | MS (ISP) 409.3 [(M + H)⁺] mp 262° C. |
| 8.13 | S1.6 | 8-Pyridin-4-yl-4-trifluoromethyl-2-(3-trifluoromethyl-phenyl)-imidazo[1,5-a]pyrimidine | MS (ISP) 409.4 [(M + H)⁺] mp 258° C. |
| 8.14 | S1.7 | 8-Pyridin-4-yl-4-trifluoromethyl-2-(4-trifluoromethyl-phenyl)-imidazo[1,5-a]pyrimidine | MS (ISP) 409.4 [(M + H)⁺] mp 240° C. |
| 8.15 | S1.19 | 2-(3-Fluoro-4-trifluoromethyl-phenyl)-8-pyridin-4-yl-4-trifluoromethyl-imidazo[1,5-a]pyrimidine | MS (ISP) 427.4.0 [(M + H)⁺] mp 267° C. |
| 8.16 | S1.21 | 2-(4-Methyl-3-trifluoromethyl-phenyl)-8-pyridin-4-yl-4-trifluoromethyl-imidazo[1,5-a]pyrimidine | MS (ISP) 423.3 [(M + H)⁺] mp 222° C. |
| 8.17 | S1.22 | 2-(4-Ethoxy-3-trifluoromethyl-phenyl)-8-pyridin-4-yl-4-trifluoromethyl-imidazo[1,5-a]pyrimidine | MS (ISP) 453.5.0 [(M + H)⁺] mp 244° C. |
| 8.18 | S1.20 | 8-Pyridin-4-yl-2-[4-(2,2,2-trifluoro-ethoxy)-3-trifluoromethyl-phenyl]-4-trifluoromethyl-imidazo[1,5-a]pyrimidine | MS (ISP) 507.5 [(M + H)⁺] mp 269° C. |
| 8.19 | S1.19 | 2-(3-Methyl-4-trifluoromethyl-phenyl)-8-pyridin-4-yl-4-trifluoromethyl-imidazo[1,5-a]pyrimidine | MS (ISP) 422.1 [(M + H)⁺] mp 225° C. |
| 8.20 | S1.17 | 2-(4-Chloro-phenyl)-8-(2-methyl-pyridin-4-yl)-4-trifluoromethyl-imidazo[1,5-a]pyrimidine | MS (ISP) 389.2 [(M + H)⁺] mp 232° C. |
| 8.21 | S1.15 | 2-(4-Chloro-3-methyl-phenyl)-8-(2-methyl-pyridin-4-yl)-4-trifluoromethyl-imidazo[1,5-a]pyrimidine | MS (ISP) 403.4 [(M + H)⁺] mp 246° C. |
| 8.22 | S1.14 | 2-(3-Chloro-4-fluoro-phenyl)-8-(2-methyl-pyridin-4-yl)-4-trifluoromethyl-imidazo[1,5-a]pyrimidine | MS (ISP) 407.3 [(M + H)⁺] mp 255° C. |

-continued

| Ex. | dione | compound name | MS (ISP)/mp |
|---|---|---|---|
| 8.23 | S1.16 | 2-(4-Dichloro-phenyl)-8-(2-methyl-pyridin-4-yl)-4-trifluoromethyl-imidazo[1,5-a]pyrimidine | MS (ISP) 423.2 [(M + H)$^+$] mp 271° C. |
| 8.24 | S1.7 | 8-(2-Methyl-pyridin-4-yl)-4-trifluoromethyl-2-(4-trifluoromethyl-phenyl)-imidazo[1,5-a]pyrimidine | MS (ISP) 423.2 [(M + H)$^+$] mp 257° C. |
| 8.25 | S1.6 | 8-(2-Methyl-pyridin-4-yl)-4-trifluoromethyl-2-(3-trifluoromethyl-phenyl)-imidazo[1,5-a]pyrimidine | MS (ISP) 423.2 [(M + H)$^+$] mp 234° C. |
| 8.26 | S1.18 | 2-(3-Fluoro-4-trifluoromethyl-phenyl)-8-(2-methyl-pyridin-4-yl-4-trifluoromethyl-imidazo[1,5-a]pyrimidine | MS (ISP) 441.2 [(M + H)$^+$] mp 252° C. |
| 8.27 | S1.22 | 2-(4-Ethoxy-3-trifluoromethyl-phenyl)-8-(2-methyl-pyridin-4-yl-4-trifluoromethyl-imidazo[1,5-a]pyrimidine | MS (ISP) 467.4 [(M + H)$^+$] mp 249° C. |
| 8.28 | S1.20 | 8-(2-Methyl-pyridin-4-yl-2-[4-(2,2,2-trifluoro-ethoxy)-3-trifluoromethyl-phenyl]-4-trifluoromethyl-imidazo[1,5-a]pyrimidine | MS (ISP) 521.4 [(M + H)$^+$] mp 219° C. |
| 8.29 | S1.19 | 2-(3-Methyl-4-trifluoromethyl-phenyl)-8-(2-methyl-pyridin-4-yl)-4-trifluoromethyl-imidazo[1,5-a]pyrimidine | MS (ISP) 437.4 [(M + H)$^+$] mp 243° C. |
| 8.30 | S1.26 | 2-(3-Ethoxy-4-trifluoromethyl-phenyl)-8-pyridin-4-yl-4-trifluoromethyl-imidazo[1,5-a]pyrimidine | MS (ISP) 453.4 [(M + H)$^+$] mp 212° C. |
| 8.31 | S1.26 | 2-(3-Ethoxy-4-trifluoromethyl-phenyl)-8-(2-methyl-pyridin-4-yl)-4-trifluoromethyl-imidazo[1,5-a]pyrimidine | MS (ISP) 467.2 [(M + H)$^+$] mp 177° C. |
| 8.32 | S1.27 | 8-Pyridin-4-yl-2-[3-(2,2,2-trifluoro-ethoxy)-4-trifluoromethyl-phenyl]-4-trifluoromethyl-imidazo[1,5-a]pyrimidine | MS (ISP) 507.4 [(M + H)$^+$] mp 233° C. |
| 8.33 | S1.27 | 8-(2-Methyl-pyridin-4-yl)-2-[3-(2,2,2-trifluoro-ethoxy)-4-trifluoromethyl-phenyl]-4-trifluoromethyl-imidazo[1,5-a]pyrimidine | MS (ISP) 521.3 [(M + H)$^+$] mp 189° C. |
| 8.34 | S1.28 | 2-(3,4-Bis-trifluoromethyl-phenyl)-8-pyridin-4-yl-4-trifluoromethyl-imidazo[1,5-a]pyrimidine | MS (ISP) 477.2 [(M + H)$^+$] mp 211° C. |
| 8.35 | S1.28 | 2-(3,4-Bis-trifluoromethyl-phenyl)-8-(2-methyl-pyridin-4-yl)-4-trifluoromethyl-imidazo[1,5-a]pyrimidine | MS (ISP) 491.3 [(M + H)$^+$] mp 218° C. |
| 8.36 | S1.29 | 2-(4-Bromo-phenyl)-8-(2-methyl-pyridin-4-yl)-4-trifluoromethyl-imidazo[1,5-a]pyrimidine | MS (ISP) 435.3 [(M + H)$^+$] mp 249° C. |

EXAMPLE 8.1

2-(4-Chloro-3-methyl-phenyl)-8-pyridin-3-yl-4-trifluoromethyl-imidazo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as a red solid (43 mg, 22%). MS (ISP) 289.3 [(M+H)$^+$]; mp 210° C.

EXAMPLE 8.2

2-(4-Chloro-phenyl)-8-pyridin-3-yl-4-trifluoromethyl-imidazo[1,5-a]pyrimidine

Reaction of 1-(4-chloro-phenyl)-4,4,4-trifluoro-butane-1,3-dione (125 mg, 0.5 mmol), prepared from commercially available 4-chloro-acetophenone according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as an orange solid (43 mg, 23%). MS (ISP) 375.5 [(M+H)$^+$]; mp 206° C.

EXAMPLE 8.3

2-(3-Chloro-4-fluoro-phenyl)-8-pyridin-3-yl-4-trifluoromethyl-imidazo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as an orange solid (62 mg, 32%). Orange solid. MS (ISP) 393.1 [(M+H)$^+$]; mp 188° C.

EXAMPLE 8.4

2-(4-Dichloro-phenyl)-8-pyridin-3-yl-4-trifluoromethyl-imidazo[1,5-a]pyrimidine

Reaction of 1-(3,4-dichloro-phenyl)-4,4,4-trifluoro-butane-1,3-dione (143 mg, 0.5 mmol), prepared from commercially available 3,4-dichloro-acetophenone according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as an orange solid (66 mg, 32%). Red solid. MS (ISP) 409.4 [(M+H)$^+$]; mp 226° C.

EXAMPLE 8.5

8-Pyridin-3-yl-4-trifluoromethyl-2-(3-trifluoromethyl-phenyl)-imidazo[1,5-a]pyrimidine Reaction of 1-(3-trifluoromethyl-phenyl)-4,4,4-trifluoro-butane-1,3-dione (284 mg, 1.0 mmol), prepared from commercially available 3-trifluoromethyl-acetophenone according to general procedure A, and 2-amino-3-(3-pyridinyl)-1H-imidazole dihydrochloride [synthesis: see part amino-imidazole derivatives] (233 mg, 1.0 mmol) according to general procedure B yielded the title compound as a red solid (54 mg, 13%). MS (ISP) 409.4 [(M+H)$^+$]; mp 194° C.

EXAMPLE 8.6

8-Pyridin-3-yl-4-trifluoromethyl-2-(4-trifluoromethyl-phenyl)-imidazo[1,5-a]pyrimidine Reaction of 1-(4-trifluoromethyl-phenyl)-4,4,4-trifluoro-butane-1,3-dione (284 mg, 1.0 mmol), prepared from commercially available 4-trifluoromethyl-acetophenone according to general procedure A, and 2-amino-3-(3-pyridinyl)-1H-imidazole dihydrochloride [synthesis: see part amino-imidazole derivatives] (233 mg, 1.0 mmol) according to general procedure B yielded the title compound as an orange solid (73 mg, 18%). MS (ISP) 409.4 [(M+H)$^+$]; mp 231° C.

EXAMPLE 8.7

2-(4-Methyl-3-trifluoromethyl-phenyl)-8-pyridin-3-yl-4-trifluoromethyl-imidazo[1,5-a]pyrimidine Reaction of 1-(4-methyl-3-trifluoromethyl-phenyl)-4,4,4-trifluoro-butane-1,3-dione (149 mg, 0.5 mmol), prepared from 4-methyl-3-trifluoromethyl-acetophenone (synthesis: see part acetophenone derivatives) according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as a red solid (84 mg, 40%). MS (ISP) 423.1 [(M+H)$^+$]; mp 236° C.

EXAMPLE 8.8

2-(3-Methyl-4-trifluoromethyl-phenyl)-8-pyridin-3-yl-4-trifluoromethyl-imidazo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 2-amino-3-(3-pyridinyl)-1H-imidazole dihydrochloride [synthesis: see part amino-imidazole derivatives] (117 mg, 0.5 mmol) according to general procedure B yielded the title compound as an orange solid (103 mg, 49%). MS (ISP) 423.3 [(M+H)$^+$]; mp 173° C.

EXAMPLE 8.9

2-(4-Chloro-phenyl)-8-pyridin-4-yl-4-trifluoromethyl-imidazo[1,5-a]pyrimidine

Reaction of 1-(4-chloro-phenyl)-4,4,4-trifluoro-butane-1,3-dione (125 mg, 0.5 mmol), prepared from commercially available 4-chloro-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (44 mg, 23%). MS (ISP) 375.5 [(M+H)$^+$]; mp 290° C.

EXAMPLE 8.10

2-(4-Chloro-3-methyl-phenyl)-8-pyridin-4-yl-4-trifluoromethyl-imidazo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (98 mg, 50%). MS (ISP) 389.3 [(M+H)$^+$]; mp 254° C.

EXAMPLE 8.11

2-(3-Chloro-4-fluoro-phenyl)-8-pyridin-4-yl-4-trifluoromethyl-imidazo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (84 mg, 43%). MS (ISP) 393.1 [(M+H)$^+$]; mp 266° C.

EXAMPLE 8.12

2-(4-Dichloro-phenyl)-8-pyridin-4-yl-4-trifluoromethyl-imidazo[1,5-a]pyrimidine

Reaction of 1-(3,4-dichloro-phenyl)-4,4,4-trifluoro-butane-1,3-dione (143 mg, 0.5 mmol), prepared from commercially available 3,4-dichloro-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (95 mg, 46%). MS (ISP) 409.3 [(M+H)$^+$]; mp 262° C.

EXAMPLE 8.13

8-Pyridin-4-yl-4-trifluoromethyl-2-(3-trifluoromethyl-phenyl)-imidazo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (100 mg, 49%). MS (ISP) 409.4 [(M+H)$^+$]; mp 258° C.

EXAMPLE 8.14

8-Pyridin-4-yl-4-trifluoromethyl-2-(4-trifluoromethyl-phenyl)-imidazo[1,5-a]pyrimidine Reaction of 1-(4-trifluoromethyl-phenyl)-4,4,4-trifluoro-butane-1,3-dione (142 mg, 0.5 mmol), prepared from commercially available 4-trifluoromethyl-acetophenone according to general procedure A, and 2-amino-3-(4-pyridinyl)-1H- imidazole [synthesis: see part amino-imidazole derivatives] (80 mg, 0.5 mmol) according to general procedure B yielded the title compound as an orange solid (88 mg, 43%). MS (ISP) 409.4 [(M+H)+]; mp 240° C.

EXAMPLE 8.15

2-(3-Fluoro-4-trifluoromethyl-phenyl)-8-pyridin-4-yl-4-trifluoromethyl-imidazo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (116 mg, 54%). MS (ISP) 427.4.0 [(M+H)+]; mp 267° C.

EXAMPLE 8.16

2-(4-Methyl-3-trifluoromethyl-phenyl)-8-pyridin-4-yl-4-trifluoromethyl-imidazo[1,5-a]pyrimidine Reaction of 1-(4-methyl-3-trifluoromethyl-phenyl)-4,4,4-trifluoro-butane-1,3-dione (149 mg, 0.5 mmol), prepared from 4-methyl-3-trifluoromethyl-acetophenone (synthesis: see part acetophenone derivatives) according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (101 mg, 48%). MS (ISP) 423.3 [(M+H)+]; mp 222° C.

EXAMPLE 8.17

2-(4-Ethoxy-3-trifluoromethyl-phenyl)-8-pyridin-4-yl-4-trifluoromethyl-imidazo[1,5-a]pyrimidine Reaction of 1-(4-ethoxy-3-trifluoromethyl-phenyl)-4,4,4-trifluoro-butane-1,3-dione (164 mg, 0.5 mmol), prepared from 4-ethoxy-3-trifluoromethyl-acetophenone (synthesis: see part acetophenone derivatives) according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (98 mg, 43%). MS (ISP) 453.5.0 [(M+H)+]; mp 244° C.

EXAMPLE 8.18

8-Pyridin-4-yl-2-[4-(2,2,2-trifluoro-ethoxy)-3-trifluoromethyl-phenyl]-4-trifluoromethyl-imidazo[1,5-a]pyrimidine Reaction of 1-[4-(2,2,2-trifluoro-ethoxy)-3-trifluoromethyl-phenyl]-4,4,4-trifluoro-butane-1,3-dione (191 mg, 0.5 mmol), prepared from 4-(2,2,2-trifluoro-ethoxy)-3-trifluoromethyl-acetophenone (synthesis: see part acetophenone derivatives) according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (111 mg, 44%). MS (ISP) 507.5 [(M+H)+]; mp 269° C.

EXAMPLE 8.19

2-(3-Methyl-4-trifluoromethyl-phenyl)-8-pyridin-4-yl-4-trifluoromethyl-imidazo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (93 mg, 44%). MS (ISP) 422.1 [(M+H)+]; mp 225° C.

EXAMPLE 8.20

2-(4-Chloro-phenyl)-8-(2-methyl-pyridin-4-yl)-4-trifluoromethyl-imidazo[1,5-a]pyrimidine Reaction of 1-(4-chloro-phenyl)-4,4,4-trifluoro-butane-1,3-dione (125 mg, 0.5 mmol), prepared from commercially available 4-chloro-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (46 mg, 24%). MS (ISP) 389.2 [(M+H)+]; mp 232° C.

EXAMPLE 8.21

2-(4-Chloro-3-methyl-phenyl)-8-(2-methyl-pyridin-4-yl)-4-trifluoromethyl-imidazo[1,5-a]pyrimidine Reaction of 1-(4-chloro-3-methyl-phenyl)-4,4,4-trifluoro-butane-1,3-dione (132 mg, 0.5 mmol), prepared from commercially available 4-chloro-3-methyl-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (49 mg, 24%). MS (ISP) 403.4 [(M+H)+]; mp 246° C.

EXAMPLE 8.22

2-(3-Chloro-4-fluoro-phenyl)-8-(2-methyl-pyridin-4-yl)-4-trifluoromethyl-imidazo[1,5-a]pyrimidine Reaction of 1-(3-chloro-4-fluoro-phenyl)-4,4,4-trifluoro-butane-1,3-dione (134 mg, 0.5 mmol), prepared from commercially available 3-chloro-4-fluoro-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (52 mg, 26%). MS (ISP) 407.3 [(M+H)+]; mp 255° C.

EXAMPLE 8.23

2-(4-Dichloro-phenyl)-8-(2-methyl-pyridin-4-yl)-4-trifluoromethyl-imidazo[1,5-a]pyrimidine Reaction of 1-(3,4-dichloro-phenyl)-4,4,4-trifluoro-butane-1,3-dione (143 mg, 0.5 mmol), prepared from commercially available 3,4-dichloro-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (57 mg, 27%). MS (ISP) 423.2 [(M+H)$^+$]; mp 271° C.

EXAMPLE 8.24

8-(2-Methyl-pyridin-4-yl)-4-trifluoromethyl-2-(4-trifluoromethyl-phenyl)-imidazo[1,5-a]pyrimidine Reaction of 1-(4-trifluoromethyl-phenyl)-4,4,4-trifluoro-butane-1,3-dione (142 mg, 0.5 mmol), prepared from commercially available 4-trifluoromethyl-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (46 mg, 22%). MS (ISP) 423.2 [(M+H)$^+$]; mp 257° C.

EXAMPLE 8.25

8-(2-Methyl-pyridin-4-yl)-4-trifluoromethyl-2-(3-trifluoromethyl-phenyl)-imidazo[1,5-a]pyrimidine Reaction of 1-(3-trifluoromethyl-phenyl)-4,4,4-trifluoro-butane-1,3-dione (142 mg, 0.5 mmol), prepared from commercially available 3-trifluoromethyl-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (59 mg, 28%). MS (ISP) 423.2 [(M+H)$^+$]; mp 234° C.

EXAMPLE 8.26

2-(3-Fluoro-4-trifluoromethyl-phenyl)-8-(2-methyl-pyridin-4-yl-4-trifluoromethyl-imidazo[1,5-a]pyrimidine Reaction of 1-(3-fluoro-4-trifluoromethyl-phenyl)-4,4,4-trifluoro-butane-1,3-dione (151 mg, 0.5 mmol), prepared from commercially available 3-fluoro-4-trifluoromethyl-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as a red solid (59 mg, 27%). MS (ISP) 441.2 [(M+H)$^+$]; mp 252° C.

EXAMPLE 8.27

2-(4-Ethoxy-3-trifluoromethyl-phenyl)-8-(2-methyl-pyridin-4-yl-4-trifluoromethyl-imidazo[1,5-a]pyrimidine Reaction of 1-(4-ethoxy-3-trifluoromethyl-phenyl)-4,4,4-trifluoro-butane-1,3-dione (164 mg, 0.5 mmol), prepared from 4-ethoxy-3-trifluoromethyl-acetophenone (synthesis: see part acetophenone derivatives) according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (41 mg, 18%). MS (ISP) 467.4 [(M+H)$^+$]; mp 249° C.

EXAMPLE 8.28

8-(2-Methyl-pyridin-4-yl-2-[4-(2,2,2-trifluoro-ethoxy)-3-trifluoromethyl-phenyl]-4-trifluoromethyl-imidazo[1,5-a]pyrimidine Reaction of 1-[4-(2,2,2-trifluoro-ethoxy)-3-trifluoromethyl-phenyl]-4,4,4-trifluoro-butane-1,3-dione (191 mg, 0.5 mmol), prepared from 4-(2,2,2-trifluoro-ethoxy)-3-trifluoromethyl-acetophenone (synthesis: see part acetophenone derivatives) according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (51 mg, 20%). Orange solid. MS (ISP) 521.4 [(M+H)$^+$]; mp 219° C.

EXAMPLE 8.29

2-(3-Methyl-4-trifluoromethyl-phenyl)-8-(2-methyl-pyridin-4-yl)-4-trifluoromethyl-imidazo[1,5-a]pyrimidine Reaction of 1-(3-methyl-4-trifluoromethyl-phenyl)-4,4,4-trifluoro-butane-1,3-dione (149 mg, 0.5 mmol), prepared from 3-methyl-4-trifluoromethyl-acetophenone (synthesis: see part acetophenone derivatives) according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (44 mg, 20%). Orange solid. MS (ISP) 437.4 [(M+H)$^+$]; mp 243° C.

EXAMPLE 8.30

2-(3-Ethoxy-4-trifluoromethyl-phenyl)-8-pyridin-4-yl-4-trifluoromethyl-imidazo[1,5-a]pyrimidine Reaction of 1-(3-ethoxy-4-trifluoromethyl-phenyl)-4,4,4-trifluoro-butane-1,3-dione (164 mg, 0.5 mmol), prepared from 3-ethoxy-4-trifluoromethyl-acetophenone (synthesis: see part acetophenone derivatives) according to general procedure A, and 2-amino-3-(4-pyridinyl)-1H-imidazole [synthesis: see part amino-imidazole derivatives] (80 mg, 0.5 mmol) according to general procedure B yielded the title compound as an orange solid (70 mg, 31%). MS (ISP) 453.4 [(M+H)$^+$]; mp 212° C.

EXAMPLE 8.31

2-(3-Ethoxy-4-trifluoromethyl-phenyl)-8-(2-methyl-pyridin-4-yl)-4-trifluoromethyl-imidazo[1,5-a]pyrimidine Reaction of 1-(3-ethoxy-4-trifluoromethyl-phenyl)-4,4,4-trifluoro-butane-1,3-dione (164 mg, 0.5 mmol), prepared from 3-ethoxy-4-trifluoromethyl-acetophenone (synthesis: see part acetophenone derivatives) according to general procedure A, and 2-amino-3-(4-pyridinyl)-1H-imidazole [synthesis: see part amino-imidazole derivatives] (87 mg, 0.5 mmol) according to general procedure B yielded the title compound as an orange solid (30 mg, 13%). MS (ISP) 467.2 [(M+H)$^+$]; mp 177° C.

EXAMPLE 8.32

8-Pyridin-4-yl-2-[3-(2,2,2-trifluoro-ethoxy)-4-trifluoromethyl-phenyl]-4-trifluoromethyl-imidazo[1,5-a]pyrimidine Reaction of 1-[3-(2,2,2-trifluoro-ethoxy)-4-trifluoromethyl-phenyl]-4,4,4-trifluoro-butane-1,3-dione (191 mg, 0.5 mmol), prepared from 3-(2,2,2-trifluoro-ethoxy)-4-trifluoromethyl-acetophenone (synthesis: see part acetophenone derivatives) according to general procedure A, and 2-amino-3-(4-pyridinyl)-1H-imidazole [synthesis: see part amino-imidazole derivatives] (87 mg, 0.5 mmol) according to general procedure B yielded the title compound as an orange solid (84 mg, 33%). MS (ISP) 507.4 [(M+H)$^+$]; mp 233° C.

EXAMPLE 8.33

8-(2-Methyl-pyridin-4-yl)-2-[3-(2,2,2-trifluoro-ethoxy)-4-trifluoromethyl-phenyl]-4-trifluoromethyl-imidazo[1,5-a]pyrimidine Reaction of 1-[3-(2,2,2-trifluoro-ethoxy)-4-trifluoromethyl-phenyl]-4,4,4-trifluoro-butane-1,3-dione (191 mg, 0.5 mmol), prepared from 3-(2,2,2-trifluoro-ethoxy)-4-trifluoromethyl-acetophenone (synthesis: see part acetophenone derivatives) according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (140 mg, 54%). MS (ISP) 521.3 [(M+H)$^+$]; mp 189° C.

EXAMPLE 8.34

2-(3,4-Bis-trifluoromethyl-phenyl)-8-pyridin-4-yl-4-trifluoromethyl-imidazo[1,5-a]pyrimidine Reaction of 1-(3,4-bis-trifluoromethyl-phenyl)-4,4,4-trifluoro-butane-1,3-dione (176 mg, 0.5 mmol), prepared from 3,4-bis-trifluoromethyl-acetophenone [CAS No. 129604-25-7] according to general procedure A, and 2-amino-3-(4-pyridinyl)-1H-imidazole [synthesis: see part amino-imidazole derivatives] (87 mg, 0.5 mmol) according to general procedure B yielded the title compound as an orange solid (80 mg, 34%). MS (ISP) 477.2 [(M+H)$^+$]; mp 211° C.

EXAMPLE 8.35

2-(3,4-Bis-trifluoromethyl-phenyl)-8-(2-methyl-pyridin-4-yl)-4-trifluoromethyl-imidazo[1,5-a]pyrimidine Reaction of 1-(3,4-bis-trifluoromethyl-phenyl)-4,4,4-trifluoro-butane-1,3-dione (200 mg, 0.57 mmol), prepared from 3,4-bis-trifluoromethyl-acetophenone [CAS No. 129604-25-7] according to general procedure A, and 2-amino-3-(2-methyl-4-pyridinyl)-1H-imidazole [synthesis: see part amino-imidazole derivatives] (99 mg, 0.57 mmol) according to general procedure B yielded the title compound as an orange solid (28 mg, 10%). Orange solid. MS (ISP) 491.3 [(M+H)$^+$]; mp 218° C.

EXAMPLE 8.36

2-(4-Bromo-phenyl)-8-(2-methyl-pyridin-4-yl)-4-trifluoromethyl-imidazo[1,5-a]pyrimidine Reaction of 1-(4-bromo-phenyl)-4,4,4-trifluoro-butane-1,3-dione (148 mg, 0.5 mmol), prepared from commercially available 4-bromo-acetophenone according to general procedure A, and 2-amino-3-(2-methyl-4-pyridinyl)-1H-imidazole [synthesis: see part amino-imidazole derivatives] (87 mg, 0.5 mmol) according to general procedure B yielded the title compound as an orange solid (42 mg, 19%). MS (ISP) 435.3 [(M+H)$^+$]; mp 249° C.

EXAMPLE 9

Preparation of 5-phenyl-3-pyridinyl-7-difluoromethyl-pyrazolo[1,5-a]pyrimidines

General Procedure B

A stirred mixture of a 3-amino-4-pyridinyl-pyrazole (1 eq.) and a 1-phenyl-4,4,4-difluoro-butane-1,3-dione (1 eq.), prepared according to general procedure A, in acetic acid was heated under reflux conditions for about 3.5 h. The reaction mixture was evaporated and the product was isolated by column chromatography (e.g. heptane/ethyl acetate) and further purified by crystallization. If the product precipitates during the reaction it can be isolated by filtration and further purified by crystallization.

| Ex. | dione | compound name | MS (ISP)/mp |
|---|---|---|---|
| 9.1 | S1.7 | 7-Difluoromethyl-3-pyridin-4-yl-5-(4-trifluoromethyl-phenyl)-pyrazolo[1,5-a]pyrimidine | MS (ISP) 391.2 [(M + H)$^+$] mp 222° C. |
| 9.2 | S1.7 | 7-Difluoromethyl-3-(2-methyl-pyridin-4-yl)-5-(4-trifluoromethyl-phenyl)-pyrazolo[1,5-a]pyrimidine | MS (ISP) 405.4 [(M + H)$^+$] mp 213° C. |
| 9.3 | S1.19 | 7-Difluoromethyl-5-(3-methyl-4-trifluoromethyl-phenyl)-3-pyridin-4-yl-pyrazolo[1,5-a]pyrimidine | MS (ISP) 405.4 [(M + H)$^+$] mp 236° C. |
| 9.4 | S1.19 | 7-Difluoromethyl-3-(2-methyl-pyridin-4-yl)-5-(3-methyl-4-trifluoromethyl-phenyl)-pyrazolo[1,5-a]pyrimidine | MS (ISP) 419.3 [(M + H)$^+$] mp 221° C. |
| 9.5 | S1.30 | 7-Difluoromethyl-5-(4-methoxy-phenyl)-3-pyridin-4-yl-pyrazolo[1,5-a]pyrimidine | MS (ISP) 353.2 [(M + H)$^+$] mp 206° C. |

EXAMPLE 9.1

7-Difluoromethyl-3-pyridin-4-yl-5-(4-trifluoromethyl-phenyl)-pyrazolo[1,5-a]pyrimidine Reaction of 4,4-difluoro-1-(4-trifluoromethyl-phenyl)-butane-1,3-dione (133 mg, 0.5 mmol), prepared from commercially available 4-trifluoromethyl-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (130 mg, 67%). MS (ISP) 391.2 [(M+H)$^+$]; mp 222° C.

EXAMPLE 9.2

7-Difluoromethyl-3-(2-methyl-pyridin-4-yl)-5-(4-trifluoromethyl-phenyl)-pyrazolo[1,5-a]pyrimidine Reaction of 4,4-difluoro-1-(4-trifluoromethyl-phenyl)-butane-1,3-dione (133 mg, 0.5 mmol), prepared from commercially available 4-trifluoromethyl-acetophenone according to general procedure A, and 3-amino-4-(2-methyl-4-pyridinyl)-pyrazole [prepared from 4-cyanomethyl-2-methyl-pyridine, as described in Bioorg. Med. Chem. Lett. 12 (2002) 3537-3541] (87 mg, 0.5 mmol) according to general procedure B yielded the title compound as a yellow solid (159 mg, 79%). MS (ISP) 405.4 [(M+H)$^+$]; mp 213° C.

EXAMPLE 9.3

7-Difluoromethyl-5-(3-methyl-4-trifluoromethyl-phenyl)-3-pyridin-4-yl-pyrazolo[1,5-a]pyrimidine Reaction of 4,4-difluoro-1-(3-methyl-4-trifluoromethyl-phenyl)-butane-1,3-dione (140 mg, 0.5 mmol), prepared from 3-methyl-4-trifluoromethyl-acetophenone (synthesis: see part acetophenone derivatives) according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (140 mg, 69%). MS (ISP) 405.4 [(M+H)$^+$]; mp 236° C.

EXAMPLE 9.4

7-Difluoromethyl-3-(2-methyl-pyridin-4-yl)-5-(3-methyl-4-trifluoromethyl-phenyl)-pyrazolo[1,5-a]pyrimidine Reaction of 4,4-difluoro-1-(3-methyl-4-trifluoromethyl-phenyl)-butane-1,3-dione (140 mg, 0.5 mmol), prepared from 3-methyl-4-trifluoromethyl-acetophenone (synthesis: see part acetophenone derivatives) according to general procedure A, and 3-amino-4-(2-methyl-4-pyridinyl)-pyrazole [prepared from 4-cyanomethyl-2-methyl-pyridine, CAS No. 130138-46-4, as described in Bioorg. Med. Chem. Lett. 12 (2002) 3537-3541] (87 mg, 0.5 mmol) according to general procedure B yielded the title compound as a yellow solid (164 mg, 78%). MS (ISP) 419.3 [(M+H)$^+$]; mp 221° C.

EXAMPLE 9.5

7-Difluoromethyl-5-(4-methoxy-phenyl)-3-pyridin-4-yl-pyrazolo[1,5-a]pyrimidine

Reaction of 4,4-difluoro-1-(4-methoxy-phenyl)-butane-1,3-dione (114 mg, 0.5 mmol), prepared from commercially available 4-methoxy-acetophenone according to general procedure A, and 3-amino-4-(4-pyridinyl)-pyrazole [CAS No. 216661-87-9; prepared from 4-cyanomethyl-pyridine as described in Bioorg. Med. Chem. Lett. 12 (2002) 3537-3541] (80 mg, 0.5 mmol) according to general procedure B yielded the title compound as a yellow solid (120 mg, 68%). MS (ISP) 353.2 [(M+H)$^+$]; mp 206° C.

Compounds of formula I and their pharmaceutically acceptable salts (hereinafter: Pharmaceutical Compound) have pharmacological activity and are useful as pharmaceuticals. In particular, Pharmaceutical Compounds exhibit metabotropic glutamate receptor antagonist activity. In particular, Pharmaceutical Compounds are active at the mGluR2 receptor.

The mGluR interaction of the Pharmaceutical Compounds may be demonstrated, e.g. in an in vitro binding assay, e.g. as follows:

[$^3$H]-LY354740 Binding on mGlu2 Transfected CHO Cell Membranes

Transfection and cell culture: cDNA encoding the rat mGlu2 receptor protein in pBluescript II was subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialyzed foetal calf serum from Gibco BRL (Basel, Switzerland). Selection was made in the presence of G-418 (1000 µg/ml final). Clones were identified by reverse transcription of 5 µg total RNA, follow by PCR using mGlu2 receptor specific primers 5'-atcactgcttgggtttctg-gcactg-3' (SEQ ID NO: 1) and 5'-agcatcactgtgggtggcatag-gagc-3' (SEQ ID NO:2) in 60 mM Tris HCl (pH 10), 15 mM (NH4)$_2$SO$_4$, 2 mM MgCl$_2$, 25 units/ml Taq Polymerase with 30 cycles annealing at 60° C. for 1 min., extension at 72° C. for 30 s, and 1 min. 95° C. denaturation.

Membrane preparation: Cells, cultured as above, were harvested and washed three times with cold PBS and frozen at −80° C. The pellet was resuspended in cold 20 mM HEPES-NaOH buffer containing 10 mM EDTA (pH 7.4), and homogenized with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[$^3$H]-LY354740 binding: After thawing, the membranes were resuspended in cold 50 mM Tris-HCl buffer containing 2 mM MgCl$_2$ and 2 mM CaCl$_2$, (pH 7) (binding buffer). The final concentration of the membranes in the assays was 25 µg protein/ml. Inhibition experiments were performed with membranes incubated with 10 nM [$^3$H]-LY354740 at room temperature, for 1 hour, in the presence of various concentrations of the compound to be tested. Following the incubations, membranes were filtered onto Whatmann GF/C glass fiber filters and washed 5 times with cold binding buffer. Non specific binding was measured in the presence of 10 µM DCG IV. After transfer of the filters into plastic vials containing 10 ml of Ultima-gold scintillation fluid (Packard, Zürich, Switzerland), the radioactivity was measured by liquid scintillation in a Tri-Carb 2500 TR counter (Packard, Zürich, Switzerland).

Data analysis: The inhibition curves were fitted with a four parameter logistic equation giving IC$_{50}$ values, and Hill coefficients.

The compounds show activities, as measured in the above assay, of 5 µM or less, typically 0.5 µM or less, and ideally of 0.1 µM or less. The below table shows exemplary $K_i$ values:

| Compound no. | mGluR2 $K_i$ [µM] | Example | mGluR2 $K_i$ [µM] |
| --- | --- | --- | --- |
| 1.13 | 0.043 | 4.35 | 0.045 |
| 1.19 | 0.032 | 4.43 | 0.048 |
| 2.2 | 0.072 | 4.9 | 0.047 |
| 3.2 | 0.076 | 5.20 | 0.043 |
| 4.24 | 0.043 | 7.1 | 0.0439 |

Activity specifically as medicament in Alzheimer's disease may be demonstrated in accordance with standard test methods, e.g. an asymptotic performance in an operant delayed match to position (DMTP) task, modified from the procedure originally published by Dunnett, Psychopharmacology (Berl) 87:357-63 (1985) [Higgins et al., Europ. J. Neuroscience 15:1827-1840 (2002); Higgins et al., Europ. J. Neuroscience 15:911-922 (2002); Higgins et al., Neuropharmacology 44:324-241 (2003)].

Pharmaceutical Compounds and prodrugs thereof, e.g. esters, N-oxides, phosphate esters, glycoamide esters and glyceride conjugates, are accordingly useful as mGluR antagonists, e.g. in the treatment or prevention of diseases and conditions in which activation of mGluR plays a role or is implicated. Such conditions include in particular acute and/or chronic neurological disorders.

At present, eight different members of these mGluRs are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders.

Acute and/or chronic neurological disorders include psychosis, schizophrenia, Alzheimer's disease, cognitive disorders and memory deficits like mild cognitive impairment, age-related cognitive decline, vascular dementia, Parkinsons's disease, memory impairment associated with depression or anxiety, Down's syndrome, stroke, traumatic brain injury, and attention deficit disorder. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychotic episodes, opiate addiction, anxiety, vomiting, dyskinesia and depression.

In one embodiment, the acute and/or chronic neurological disorder is Alzheimer's disease. In another embodiment, the acute and/or chronic neurological disorder is mild cognitive impairment.

As used herein, a mammal in need of treatment of an acute and/or chronic neurological disorder means a mammal, e.g. a human that is suffering from, or is at risk of suffering from, an acute and/or chronic neurological disorder.

As used herein, the terms "treat", treating "and treatment", and the like, as applied to an acute and/or chronic neurological disorder, refer to methods that slow, ameliorate, reduce or reverse such a disorder or any symptoms associated with said disorder, as currently afflicting the subject, as well as methods that prevent such a disorder or any symptoms thereof, from occurring.

Pharmaceutical Compounds can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

Pharmaceutical Compounds can be processed with pharmaceutically inert, inorganic or organic carriers for the production of pharmaceutical compositions. Lactose, corn starch or derivatives thereof, talc, stearic acid or its salts and the like can be used, e.g., as such carriers for tablets, coated tablets, dragées and hard gelatine capsules. Suitable carriers for soft gelatine capsules are, e.g., vegetable oils, waxes, fats, semi-solid and liquid polyols and the like; depending on the nature of the active substance no carriers are, however, usually required in the case of soft gelatine capsules. Suitable carriers for the production of solutions and syrups are, e.g., water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, e.g., natural or hardened oils, waxes, fats, semi-liquid or liquid polyols and the like.

In addition, the pharmaceutical compositions may contain preservatives, solubilizers, stabilizers, wetting agents, emulsifiers, sweeteners, colorants, flavorants, salts for varying the osmotic pressure, buffers, masking agents or antioxidants. They may also contain still other therapeutically valuable substances.

As mentioned earlier, medicaments containing Pharmaceutical Compound and a therapeutically inert excipient are also an object of the present invention, as is a process for the production of such medicaments which comprises bringing one or more Pharmaceutical Compound and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

In accordance with the foregoing the present invention also provides:

(a) A pharmaceutical compound for use as a metabotropic glutamate receptor antagonist, for example for use in any of the particular indications as hereinbefore set forth;

(b) A pharmaceutical composition comprising a pharmaceutical compound as under (a) as active ingredient together with a pharmaceutically acceptable diluent or carrier therefor;

(c) A pharmaceutical composition for the treatment or prevention of a disease or condition in which metabotropic glutamate receptor activation plays a role or is implicated comprising a pharmaceutical compound as under (a) and a carrier;

(d) Use of a pharmaceutical compound as under (a) for the manufacture of a medicament for the treatment or prevention of a disease or condition in which metabotropic glutamate receptor activation plays a role or is implicated;

(e) A process for the preparation of a compound as under (a).

The invention claimed is:

1. A compound of formula I

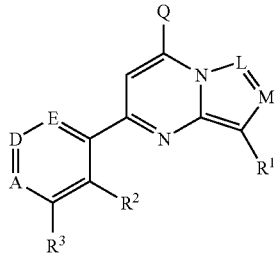

wherein
A is =C($R^4$)—,
D is =C($R^5$)—,
E is =C($R^6$)—,
or one of A, D and E is =N—,
L is =C(H)—,
M is =N—
Q is $CF_3$ of $CHF_2$,
$R^1$ is selected from —CN, unsubstituted pyridinyl, pyridinyl substituted by ($C_1$-$C_4$)-alkyl, pyridinyl substituted by ($C_1$-$C_4$)-alkanol, and corresponding pyridine-N-oxide of unsubstituted pyridinyl, pyridinyl substituted by ($C_1$-$C_4$)-alkyl, pyridinyl substituted by ($C_1$-$C_4$)-alkanol,
$R^2$ is selected from hydrogen, halogen, ($C_1$-$C_4$)-alkyl and ($C_3$-$C_6$)-cycloalkyl,
$R^3$ is selected from hydrogen, halogen, ($C_1$-$C_4$)-alkyl and ($C_3$-$C_6$)-cycloalkyl,
$R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine, $R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine, and
$R^6$ is hydrogen or halogen
or a pharmaceutically acceptable salt thereof.

2. The compound according to claim 1 wherein:
A is =C($R^4$)—,
D is =C($R^5$)—,
E is =C($R^6$)—,
or one of A, D and E is =N—,
L is =C(H)—,
M is =N—
Q is $CF_3$,
$R^1$ is selected from —CN, unsubstituted pyridinyl, pyridinyl substituted by ($C_1$-$C_4$)-alkyl and corresponding pyridine-N-oxide of pyridinyl substituted by ($C_1$-$C_4$)-alkyl,
$R^2$ is selected from hydrogen, halogen, ($C_1$-$C_4$)-alkyl and ($C_3$-$C_6$)-cycloalkyl,
$R^3$ is selected from hydrogen, halogen, ($C_1$-$C_4$)-alkyl and ($C_3$-$C_6$)-cycloalkyl,
$R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy substituted by fluorine, unsubstituted ($C_3$-$C_6$)-cycloalkyl and ($C_3$-$C_6$)-cycloalkyl substituted by fluorine,
$R^5$ is selected from hydrogen, halogen, unsubstituted ($C_1$-$C_4$)-alkyl, ($C_1$-$C_4$)-alkyl substituted by fluorine, unsubstituted ($C_3$-$C_6$)-cycloalkyl and ($C_3$-$C_6$)-cycloalkyl substituted by fluorine, and
$R^6$ is hydrogen or halogen
or a pharmaceutically acceptable salt thereof.

3. The compound according to claim 1 wherein A is =C($R^4$)—, wherein $R^4$ is selected from hydrogen, halogen, unsubstituted ($C_1$-$C_4$)-alkyl, ($C_1$-$C_4$)-alkyl substituted by fluorine, unsubstituted ($C_1$-$C_4$)-alkoxy, ($C_1$-$C_4$)-alkoxy sub-

4. The compound according to claim 3 wherein $R^4$ is halogen.

5. The compound according to claim 1 wherein D is $=C(R^5)-$, wherein $R^5$ is selected from hydrogen, halogen, unsubstituted $(C_1-C_4)$-alkyl, $(C_1-C_4)$-alkyl substituted by fluorine, unsubstituted $(C_3-C_6)$-cycloalkyl and $(C_3-C_6)$-cycloalkyl substituted by fluorine.

6. The compound according to claim 5 wherein $R^5$ is $CF_3$.

7. The compound according to claim 1 wherein E is $=C(R^6)-$, wherein $R^6$ is hydrogen or halogen.

8. The compound according to claim 1 wherein $R^1$ is —CN.

9. The compound according to claim 1 wherein $R^1$ is selected from unsubstituted pyridinyl, pyridinyl substituted by $(C_1-C_4)$-alkyl and corresponding pyridine-N-oxide of pyridinyl substituted by $(C_1-C_4)$-alkyl.

10. The compound according to claim 9 wherein $R^1$ is pyridinyl.

11. The compound according to claim 9 wherein $R^1$ is pyridinyl substituted by $(C_1-C_4)$-alkyl.

12. The compound according to claim 9 wherein $R^1$ is pyridinyl substituted by methyl.

13. The compound according to claim 9 wherein $R^1$ is 2-methyl-pyridin-4-yl.

14. The compound according to claim 1 wherein
- A is $=C(R^4)-$, wherein $R^4$ is selected from hydrogen, halogen, unsubstituted $(C_1-C_4)$-alkyl or $(C_1-C_4)$-alkyl substituted by fluorine, unsubstituted $(C_1-C_4)$-alkoxy, $(C_1-C_4)$-alkoxy substituted by fluorine, unsubstituted $(C_3-C_6)$-cycloalkyl and $(C_3-C_6)$-cycloalkyl substituted by fluorine,
- D is $=C(R^5)-$, wherein $R^5$ is selected from hydrogen, halogen, unsubstituted $(C_1-C_4)$-alkyl, $(C_1-C_4)$-alkyl substituted by fluorine, unsubstituted $(C_3-C_6)$-cycloalkyl and $(C_3-C_6)$-cycloalkyl substituted by fluorine,
- E is $=C(R^6)-$, wherein $R^6$ is hydrogen or halogen,
- L is $=C(H)-$,
- M is $=N-$,
- $R^1$ is selected from —CN, unsubstituted pyridinyl, pyridinyl substituted by $(C_1-C_4)$-alkyl, and corresponding pyridine-N-oxide of pyridinyl substituted by $(C_1-C_4)$-alkyl,
- $R^2$ is selected from hydrogen, halogen, $(C_1-C_4)$-alkyl and $(C_3-C_6)$-cycloalkyl,
- $R^3$ is selected from hydrogen, halogen, $(C_1-C_4)$-alkyl and $(C_3-C_6)$-cycloalkyl.

15. The compound according to claim 1 wherein
- A is $=C(R^4)-$, wherein $R^4$ is selected from hydrogen, halogen, unsubstituted $(C_1-C_4)$-alkyl, $(C_1-C_4)$-alkyl substituted by fluorine, unsubstituted $(C_1-C_4)$-alkoxy and $(C_1-C_4)$-alkoxy substituted by fluorine,
- D is $=C(R^5)-$, wherein $R^5$ is selected from hydrogen, halogen, unsubstituted $(C_1-C_4)$-alkyl and $(C_1-C_4)$-alkyl substituted by fluorine,
- E is $=C(R^6)-$, wherein $R^6$ is hydrogen or halogen,
- L is $=C(H)-$,
- M is $=N-$,
- $R^1$ is selected from —CN, unsubstituted pyridinyl, pyridinyl substituted by $(C_1-C_4)$-alkyl and corresponding pyridine-N-oxide of pyridinyl substituted by $(C_1-C_4)$-alkyl,
- $R^2$ is selected from hydrogen, halogen and $(C_1-C_4)$-alkyl, and
- $R^3$ is selected from hydrogen, halogen and $(C_1-C_4)$-alkyl.

16. A pharmaceutical composition comprising a compound of formula I

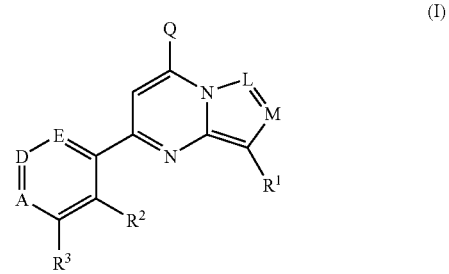

(I)

wherein
- A is $=C(R^4)-$,
- D is $=C(R^5)-$,
- E is $=C(R^6)-$,
- or one of A, D and E is $=N-$,
- L is $=C(H)-$,
- M is $=N-$,
- Q is $CF_3$ of $CHF_2$,
- $R^1$ is selected from —CN, unsubstituted pyridinyl, pyridinyl substituted by $(C_1-C_4)$-alkyl, pyridinyl substituted by $(C_1-C_4)$-alkanol, and corresponding pyridine-N-oxide of unsubstituted pyridinyl, pyridinyl substituted by $(C_1-C_4)$-alkyl, pyridinyl substituted by $(C_1-C_4)$-alkanol,
- $R^2$ is selected from hydrogen, halogen, $(C_1-C_4)$-alkyl and $(C_3-C_6)$-cycloalkyl,
- $R^3$ is selected from hydrogen, halogen, $(C_1-C_4)$-alkyl and $(C_3-C_6)$-cycloalkyl,
- $R^4$ is selected from hydrogen, halogen, unsubstituted $(C_1-C_4)$-alkyl, $(C_1-C_4)$-alkyl substituted by fluorine, unsubstituted $(C_1-C_4)$-alkoxy, $(C_1-C_4)$-alkoxy substituted by fluorine, unsubstituted $(C_3-C_6)$-cycloalkyl and $(C_3-C_6)$-cycloalkyl substituted by fluorine,
- $R^5$ is selected from hydrogen, halogen, unsubstituted $(C_1-C_4)$-alkyl, $(C_1-C_4)$-alkyl substituted by fluorine, unsubstituted $(C_3-C_6)$-cycloalkyl and $(C_3-C_6)$-cycloalkyl substituted by fluorine, and
- $R^6$ is hydrogen or halogen,
- or a pharmaceutically acceptable salt thereof, and a pharmaceutically acceptable excipient thereof.

\* \* \* \* \*

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atcactgctt gggtttctgg cactg                                          25

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agcatcactg tgggtggcat aggagc                                         26
```